(12) United States Patent
Nishida et al.

(10) Patent No.: US 11,718,846 B2
(45) Date of Patent: Aug. 8, 2023

(54) GENOMIC SEQUENCE MODIFICATION METHOD FOR SPECIFICALLY CONVERTING NUCLEIC ACID BASES OF TARGETED DNA SEQUENCE, AND MOLECULAR COMPLEX FOR USE IN SAME

(71) Applicant: NATIONAL UNIVERSITY CORPORATION KOBE UNIVERSITY, Kobe (JP)

(72) Inventors: Keiji Nishida, Kobe (JP); Akihiko Kondo, Kobe (JP); Satomi Kojima, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 0 days.

(21) Appl. No.: 16/791,968

(22) Filed: Feb. 14, 2020

(65) Prior Publication Data
US 2020/0208138 A1  Jul. 2, 2020

Related U.S. Application Data

(62) Division of application No. 15/124,021, filed as application No. PCT/JP2015/056436 on Mar. 4, 2015, now Pat. No. 10,655,123.

(30) Foreign Application Priority Data

Mar. 5, 2014 (JP) ................. 2014-043348
Sep. 30, 2014 (JP) ................. 2014-201859

(51) Int. Cl.
C12N 15/10 (2006.01)
C12N 9/22 (2006.01)
C12N 9/78 (2006.01)
C12N 15/11 (2006.01)

(52) U.S. Cl.
CPC ........... *C12N 15/1024* (2013.01); *C12N 9/22* (2013.01); *C12N 9/78* (2013.01); *C12N 15/102* (2013.01); *C12N 15/11* (2013.01); *C12Y 305/04005* (2013.01); *C07K 2319/00* (2013.01); *C07K 2319/81* (2013.01); *C12N 2310/3513* (2013.01)

(58) Field of Classification Search
CPC .................................................. C12N 2310/20
See application file for complete search history.

(56) References Cited

U.S. PATENT DOCUMENTS

| | | | |
|---|---|---|---|
| 6,117,680 A * | 9/2000 | Natesan | C07K 14/005 435/235.1 |
| 8,697,359 B1 | 4/2014 | Zhang | |
| 8,772,008 B2 | 7/2014 | Doyon | |
| 10,655,123 B2 | 5/2020 | Nishida et al. | |
| 2005/0208489 A1 | 9/2005 | Carroll et al. | |
| 2011/0002889 A1 | 1/2011 | Barrangou et al. | |
| 2011/0104787 A1 | 5/2011 | Church et al. | |
| 2011/0145940 A1 | 6/2011 | Voytas et al. | |
| 2014/0068797 A1 | 3/2014 | Doudna et al. | |
| 2014/0294773 A1 | 10/2014 | Brouns et al. | |
| 2014/0304853 A1 | 10/2014 | Ainley et al. | |
| 2014/0335521 A1 | 11/2014 | Nakamura et al. | |
| 2014/0356867 A1 | 12/2014 | Peter et al. | |
| 2015/0031134 A1 | 1/2015 | Zhang et al. | |
| 2015/0044772 A1 * | 2/2015 | Zhao | C12N 9/22 435/351 |
| 2015/0165054 A1 | 6/2015 | Liu et al. | |
| 2015/0166980 A1 * | 6/2015 | Liu | A61K 38/465 435/227 |
| 2015/0166981 A1 | 6/2015 | Liu et al. | |
| 2015/0166982 A1 | 6/2015 | Liu et al. | |
| 2015/0166983 A1 | 6/2015 | Liu et al. | |
| 2015/0166984 A1 | 6/2015 | Liu et al. | |
| 2015/0166985 A1 | 6/2015 | Liu et al. | |
| 2015/0232882 A1 | 8/2015 | Zhang et al. | |
| 2015/0315576 A1 | 11/2015 | Caliando et al. | |
| 2016/0200779 A1 | 7/2016 | Liu et al. | |
| 2017/0073670 A1 | 3/2017 | Nishida et al. | |

(Continued)

FOREIGN PATENT DOCUMENTS

CA    2933625 A1    6/2015
CN    105934516 A    9/2016
(Continued)

OTHER PUBLICATIONS

Sinkunas et al. (2011) Cas3 is a single-stranded DNA nuclease and ATP-dependent helicase in the CRISPR/Cas immune system. The EMBO Journal, 30:1335-1342 (Year: 2011).*
Makarova (2011) Evolution and classification of the CRISPR-Cas systems. Nature Reviews Microbiology, 9(6):467-477 (Year: 2011).*

(Continued)

*Primary Examiner* — Scarlett Y Goon
*Assistant Examiner* — Tiffany Nicole Grooms
(74) *Attorney, Agent, or Firm* — Seed IP Law Group LLP

(57) ABSTRACT

The invention provides a method of modifying a targeted site of a double stranded DNA, including a step of contacting a complex wherein a nucleic acid sequence-recognizing module that specifically binds to a target nucleotide sequence in a selected double stranded DNA and a nucleic acid base converting enzyme are linked, with the double stranded DNA, to convert one or more nucleotides in the targeted site to other one or more nucleotides or delete one or more nucleotides, or insert one or more nucleotides into the targeted site, without cleaving at least one strand of the double stranded DNA in the targeted site.

4 Claims, 16 Drawing Sheets
Specification includes a Sequence Listing.

(56) References Cited

U.S. PATENT DOCUMENTS

| | | | |
|---|---|---|---|
| 2017/0121693 | A1 | 5/2017 | Liu et al. |
| 2017/0321210 | A1 | 11/2017 | Nishida et al. |
| 2019/0024098 | A1 | 1/2019 | Nishida et al. |
| 2019/0085342 | A1 | 3/2019 | Nishida et al. |
| 2020/0248174 | A1 | 8/2020 | Nishida et al. |

FOREIGN PATENT DOCUMENTS

| | | |
|---|---|---|
| EP | 3115457 A1 | 1/2017 |
| EP | 3 241 902 B1 | 2/2018 |
| JP | 2010-519929 A | 6/2010 |
| JP | 4968498 B2 | 7/2012 |
| JP | 2013-513389 A | 4/2013 |
| JP | 2013-128413 A | 7/2013 |
| JP | 2015-503535 A | 2/2015 |
| WO | 2010/132092 A2 | 11/2010 |
| WO | 2011/072246 A2 | 6/2011 |
| WO | 2013/058404 A1 | 4/2013 |
| WO | 2013/098244 A1 | 7/2013 |
| WO | 2013/140250 A1 | 9/2013 |
| WO | 2013/169802 A1 | 11/2013 |
| WO | 2013/176772 A1 | 11/2013 |
| WO | 2014/071235 A1 | 5/2014 |
| WO | 2014/093595 A1 | 6/2014 |
| WO | 2014/093712 A1 | 6/2014 |
| WO | 2014/186686 A2 | 11/2014 |
| WO | 2015/035136 A2 | 3/2015 |
| WO | 2016/072399 A1 | 5/2015 |
| WO | 2015/089406 A1 | 6/2015 |
| WO | 2015/133554 A1 | 9/2015 |
| WO | 2016/069283 A1 | 5/2016 |
| WO | 2017/070632 A2 | 4/2017 |
| WO | 2017/090761 A1 | 6/2017 |

OTHER PUBLICATIONS

Zetsche et al. (2015) Cpf1 is a Single RNA-Guided Endonuclease of a Class 2 CRISPR-Cas System. Cell, 163:759-771 (Year: 2015).*
Shmakov et al. (2015) Discovery and Functional Characterization of Diverse Class 2 CRISPR-Cas Systems. Cell, 60:385-397 (Year: 2015).*
Jinek et al. (2014) Structures of Cas9 Endonucleases Reveal RNA-Mediated Conformational Activation. Science, 343:1247997, pp. 1-11 and supplementary materials (Year: 2014).*
Lada et al. (2013) Genome-Wide Mutation Avalanches Induced in Diploid Yeast Cells by a Base Analog or an APOBEC Deaminase. PLOS Genetics, 9(9):e1003736, pp. 1-17 (Year: 2013).*
Lada et al., "Mutator Effects and Mutation Signatures of Editing Deaminases Produced in Bacteria and Yeast," *Biochemistry (Moscow)* 76(1):131-146, 2011.
Freitas et al., "Mechanisms and Signals for the Nuclear Import of Proteins," *Current Genomics* 10:550-557, 2009.
Harris et al., "RNA Editing Enzyme APOBEC1 and Some of Its Homologs Can Act as DNA Mutators," *Molecular Cell* 10:1247-1253, 2002.
Wolf et al., "tadA, an essential tRNA-specific adenosine deaminase from *Escherichia coli*," *The EMBO Journal* 21(14):3841-3851, 2002.
EP Communication dated Apr. 14, 2021 for corresponding EP Application No. 16844517.9, 7 pages.
EP Summons to Attend Oral Proceedings dated May 27, 2021 for corresponding EP Application No. 16868704.4, 6 pages.
U.S. Non-Final Office Action for corresponding U.S. Appl. No. 15/757,646, dated Jun. 4, 2021, 64 pages.
U.S. Non-Final Office Action for corresponding U.S. Appl. No. 15/779,120, dated Apr. 19, 2021, 14 pages.
Office Action for CN Application No. 201680079887.5 dated May 18, 2021, 7 pages.
Restriction Requirement for U.S. Appl. No. 16/094,587, dated Jun. 28, 2021, 8 pages.
Arazoe et al., "Targeted Nucleotide Editing Technologies for Microbial Metabolic Engineering," *Biotechnol. J.* 13:1700596, 2018. (12 pages).

Bogdanove et al., "TAL Effectors: Customizable Proteins for DNA Targeting," *Science*, 333(6051): 1843-1846 (2011).
Bortesi et al., "The CRISPR/Cas9 system for plant genome editing and beyond," *Biotechnol. Adv.*, 33(1): 41-52 (2015).
Canadian Intellectual Property Office, Examination Report in Canadian Patent Application No. 2,947,941 (dated Mar. 18, 2019).
Canadian Intellectual Property Office, Examination Report in Canadian Patent Application No. 2,947,941 (dated Jun. 22, 2018).
Canadian Intellectual Property Office, Official Action and Examination Search Report in Canadian Patent Application No. 2,947,941 (dated Dec. 15, 2017).
Cermak et al., "Efficient design and assembly of custom TALEN and other TAL effector-based constructs for DNA targeting," *Nucleic Acids Research*, 39(12): e82 (2011).
Chinese Patent Office, First Office Action in Chinese Patent Application No. 201580023875.6 (dated Sep. 3, 2018).
Chinese Patent Office, Second Office Action in Chinese Patent Application No. 201580023875.6 (dated May 7, 2019).
Cho et al., "Targeted genome engineering in human cells with the Cas9 RNA-guided endonuclease," *Nat. Biotechnol.*, 31(3): 230-232 (2013).
Cong et al., "Multiplex Genome Engineering Using CRISPR/Cas Systems," *Science*, 339(6121): 819-823 (2013).
Conticello et al., "Evolution of the AID/APOBEC Family of Polynucleotide (Deoxy)cytidine Deaminases," *Mol. Biol. Evol.*, 22(2): 367-377 (2005).
Dicarlo et al., "Genome engineering in *Saccharomyces cerevisiae* using CRISPR-Cas systems," *Nucleic Acids Res.*, 339339 41(7): 4336-4343 (2013).
Esvelt et al., "Genome-scale engineering for systems and synthetic biology," *Molecular Systems Biology*, 9: 641 (2013).
European Patent Office, Communication Pursuant to Article 94(3) EPC in European Patent Application No. 15758734.6 (dated May 4, 2018).
European Patent Office, Communication Pursuant to Article 94(3) EPC in European Patent Application No. 15758734.6 (dated Apr. 4, 2019).
Fang et al., "New Method of Genome Editing Derived From CRISPR/Cas9," *Prog. Biochem. Biophys.* 40(8): 691-702 (2013).
Finney-Manchester et al., "Harnessing mutagenic homologous recombination for targeted mutagenesis in vivo by TaGTEAM," *Nucleic Acids Res.*, 41(9): e99 (2013).
Gilbert et al., "CRISPR-Mediated Modular RNA-Guided Regulation of Transcription in Eukaryotes," *Cell*, 154(2): 442-451 (2013).
Horvath et al., "CRISPR/Cas, the Immune System of Bacteria and Archaea," *Science*, 327: 167-170 (2010).
Japanese Patent Office, International Preliminary Report on Patentability in International Patent Application No. PCT/JP2015/056436 (dated May 10, 2016).
Japanese Patent Office, International Search Report in International Patent Application No. PCT/JP2015/056436 (dated Jun. 9, 2015).
Japanese Patent Office, International Search Report in International Patent Application No. PCT/JP2016/085075 (dated Feb. 21, 2017).
Japanese Patent Office, International Search Report in International Patent Application No. PCT/JP2016/076711 (dated Nov. 29, 2016).
Japanese Patent Office, International Search Report in International Patent Application No. PCT/JP2016/076448 (dated Dec. 6, 2016).
Japanese Patent Office, International Search Report in International Patent Application No. PCT/JP2017/016105 (dated Jul. 25, 2017).
Japanese Patent Office, Official Action in Japanese Patent Application No. 2017-164703 (dated May 16, 2018).
Jiang et al., "RNA-guided editing of bacterial genomes using CRISPR-Cas systems," *Nat. Biotechnol.*, 31(3): 233-239 and online methods [2 pages] (2013).
Jinek et al., "A Programmable Dual-RNA-Guided DNA Endonuclease in Adaptive Bacterial Immunity," *Science*, 337(6096): 816-821 (2012).
Jinek et al., "RNA-programmed genome editing in human cells," *eLIFE*, 2: e00471 (2013).
Kim et al., "Genome-wide target specificities of CRISPR RNA-guided programmable deaminases," *Nat. Biotechnol.*, 35(5): 475-480 (2017).

(56) References Cited

OTHER PUBLICATIONS

Kitamura et al., "Uracil DNA Glycosylase Counteracts APOBEC3G-Induced Hypermutation of Hepatitis B Viral Genomes: Excision Repair of Covalently Closed Circular DNA," *PLoS Pathog.*, 9(5): e1003361 (2013).
Komor et al., "Programmable editing of a target base in genomic DNA without double-stranded DNA cleavage," *Nature*, 533(7603): 420-424 (2016).
Krokan et al., "Base Excision Repair," *Cold Spring Harb. Perspect. Biol.*, 5(4): a012583 (2013).
Lada et al., "AID/APOBEC cytosine deaminase induces genome-wide kataegis," *Biol. Direct*, 7: 47 (2012).
Lada et al., "Genome-Wide Mutation Avalanches Induced in Diploid Yeast Cells by a Base Analog or an APOBEC Deaminase," *PLoS Genet.*, 9(9): e1003736 (2013).
Makarova et al., "Evolution and classification of the CRISPR-Cas systems," *Nat Rev Microbiol.* 9(6):467-477, 2011.
Mali et al., "Cas9 as a versatile tool for engineering biology," *Nat. Methods*, 10(10): 957-963 (2013).
Mali et al., "CAS9 transcriptional activators for target specificity screening and paired nickases for cooperative genome engineering," *Nature Biotechnology* 31(9):833-838, 2013.
Mali et al., "RNA-Guided Human Genome Engineering via Cas9," *Science*, 339(6121): 823-826(2013).
Mitsunobu et al., "Beyond Native Cas9: Manipulating Genomic Information and Function," *Trends in Biotechnology* 35(10):983-996, 2017.
Mussolino et al., "TALE nucleases: tailored genome engineering made easy," *Current Opinion in Biotechnology*, 23(5): 644-650 (2012).
Nishida et al., "Targeted nucleotide editing using hybrid prokaryotic and vertebrate adaptive immune systems," *Science*, 353(6305): aaf8729 (2016).
Non-Final Office Action dated Mar. 3, 2020 for U.S. Appl. No. 15/779,120, 6 pages.
O'Connell et al., "Programmable RNA recognition and cleavage by CRISPR/Cas9," *Nature*, 516(7530): 263-266 and Supplementary Materials—Methods, Extended Data Figures 1-8, and Extended Data Tables 1-2 (2014).
Osakabe et al., "Genome Editing with Engineered Nucleases in Plants," *Plant Cell Physiol.*, 56(3): 389-400 (2015).
Perez-Pinera et al., "RNA-guided gene activation by CRISPR-Cas9-based transcription factors," *Nat. Methods*, 10(10): 973-976 (2013).
Pingoud et al., "Type II restriction endonucleases—a historical perspective and more," *Nucleic Acids Research* 42(12):7489-7527, 2014.
Plosky, "CRISPR-Mediated Base Editing without DNA Double-Strand Breaks," *Mol. Cell.*, 62(4): 477-478 (2016).
Ran et al., "Double Nicking by RNA-Guided CRISPR Cas9 for Enhanced Genome Editing Specificity," *Cell* 154:1380-1389, 2013.
Ran et al., "Genome engineering using the CRISPR-Cas9 system," *Nat. Protoc.*, 8(11): 2281-2308 (2013).
Rittiéet al., "Enzymes used in molecular biology: a useful guide," *J. Cell Commun.* 2:25-45, 2008.
Rogozin et al., "Evolution and diversification of lamprey antigen receptors: evidence for involvement of an AID-APOBEC family cytosine deaminase," *Nat. Immunol.*, 8(6): 647-656 and Supplementary Table 1 (2007).
Shalem et al., "Genome-Scale CRISPR-Cas9 Knockout Screening in Human Cells," *Science* 343:84-87 2013, 83 pages.
Shimatani et al., "Targeted base editing in rice and tomato using a CRISPR-Cas9 cytidine deaminase fusion," *Nat. Biotechnol.*, 35(5): 441-443, Online Methods, and Corrigendum (2017).
Shmakov et al., "Discovery and Functional Characterization of Diverse Class 2 CRISPR-Cas Systems," *Molecular Cell* 60:385-397, 2015.
Szyf et al., "Maternal care, the epigenome and phenotypic differences in behavior," *Reprod. Toxicol.*, 24(1): 9-19 (2007).

Xu et al., "Efficient Genome Editing in *Clostridium cellulolyticum* via CRISPR-Cas9 Nickase," *Appl. Environ. Microbiol.*, 81(13): 4423-4431 and Supplementary Data (2015).
Zeng et al., "Highly efficient editing of the actinorhodin polyketide chain length factor gene in *Streptomyces coelicolor* M145 using CRISPR/Cas9-CodA(sm) combined system," *Appl. Microbiol. Biotechnol.*, 99(24): 10575-10585 (2015).
Zetsche et al., "Cpf1 Is a Single RNA-Guided Endonuclease of a Class 2 CRISPR-Cas System," *Cell*, 163(3): 759-771 (2015).
Al-Fageeh et al., "The Cold-Shock Response in Cultured Mammalian Cells: Harnessing the Response for the Improvement of Recombinant Protein Production," *Biotechnology and Bioengineering* 93(5):829-835, Apr. 2006.
Kim et al., "Highly efficient RNA-guided genome editing in human cells via delivery of purified Cas9 ribonucleoproteins," *Genome Research* 24:1012-1019, Apr. 2014, URL: http://www.genome.org/cgi/doi/10.1101/sr.171322.113, 16 pages.
Lada et al., "Mechanisms of regulation of AID/APOBEC deaminases activity and protection of the genome from promiscuous deamination," A Dissertation, University of Nebraska Medical Center, Omaha, Nebraska, Jun. 2014, 169 pages.
Makarova et al., "An updated evolutionary classification of CRISPR-Cas systems," *Nature Reviews* 13:722-736, Nov. 2015.
Ramakrishna et al., "Gene disruption by cell-penetrating peptide-mediated delivery of Cas9 protein and guide RNA," *Genome Research* 24:1020-1027, Apr. 2014, URL: http://www.genome.org/cgi/doi/10.1101/gr. 171264.113, 31 pages.
Remy et al., "Efficient gene targeting by homology-directed repair in rat zygotes using TALE nucleases," *Genome Research* 24:1371-1383, Jul. 2014, URL: http://www.genome.org/cgi/doi/10.1101/gr. 171538.113, 27 pages.
U.S. Non-Final Office Action for corresponding U.S. Appl. No. 16/094,587, dated Oct. 27, 2021, 148 pages.
Canadian Office Action dated Aug. 4, 2022, for corresponding Canadian Application No. 2,998,087, 6 pages.
Japanese Office Action dated Jul. 12, 2022, for corresponding Japanese Application No. 2020-073425, 3 pages.
Non-Final Office Action dated Aug. 16, 2022, for co-pending U.S. Appl. No. 15/757,646, 20 pages.
Advisory Action dated Aug. 30, 2022, for co-pending U.S. Appl. No. 16/094,587, 11 pages.
Brazilian Office Action dated Sep. 16, 2022 for corresponding Brazilian Application No. BR112018071376-7, with English translation, 7 pages.
Chinese Office Action dated Sep. 5, 2022 for corresponding Chinese Application No. 201780038364.0, with English translation, 10 pages.
Kuscu et al., "CRISPR-Cas9-AID base editor is a powerful gain-of-function screening tool," *Nature Methods* 13(12):983-984, Dec. 2016.
Ma et al., "Targeted AID-mediated mutagenesis (TAM) enables efficient genomic diversification in mammalian cells," *Nature Methods*, Advance Online Publication, 9 pages, Oct. 2016.
Communication pursuant to Article 94(3) EPC for EP Application No. 19 196 085.5, 4 pages, dated May 31, 2022.
U.S. Final Office Action for corresponding U.S. Appl. No. 16/094,587, dated Apr. 20, 2022, 55 pages.
Brief Communication, dated Mar. 4, 2022, from related European Patent Application No. 15758734.6, 17 pages.
Decision of Final Rejection, dated Apr. 25, 2022, for Chinese Patent Application No. 201680065298.1, 13 pages (w/ English Translation).
Fonfara et al., "Phylogeny of Cas9 determines functional exchangeability of dual-RNA and Cas9 among orthologous type II CRISPR-Cas systems," *Nucleic Acid Research* 42(4):2577-2590, 2014 (14 pages).
Fu et al., "Target-dependent nickase activities of CRISPR-Cas nucleases Cpf1 and Cas9," *Nat. Microbiol.* 4(5):888-897, May 2019 (22 pages).
Hsu et al., "Development and Applications of CRISPR-Cas9 for Genome Engineering," *Cell* 157:1262-1278, Jun. 2014 (17 pages).

(56) References Cited

OTHER PUBLICATIONS

Koonin et al., "Evolution of an RNA-based adaptive immunity system in prokaryotes," *RNA Biology* 10(5):679-686, May 2013 (8 pages).

Makarova et al., "Classification and Nomenclature of CRISPR-Cas Systems: Where from Here?" *The CRISPR Journal* 1(5):325-336, 2018 (12 pages).

Makarova et al., "Evolutionary classification of CRISPR-Cas systems: a burst of class 2 and derived variants," *Microbiology* 18:67-83, Feb. 2020 (17 pages).

Multiple alignment of S.*pyogenes* Cas9 amino acid sequences (the accession numbers listed correspond to the GenBank database).

Office Communication, dated Mar. 4, 2022, from United States Patent and Trademark Office for U.S. Appl. No. 15/757,646, 5 pages.

Stafforst et al., "An RNA-Deaminase Conjugate Selectively Repairs Point Mutations," *Angew. Chem. Int. Ed.* 57:11166-11169, 2012 (4 pages).

Yan et al., "Functionally diverse type V CRISPR-Cas systems," *Science* 363:88-91, Jan. 2019 (5 pages).

Mateus et al., "Lampreys of the Iberian Peninsula: distribution, population status and conservation," *Endangered Species Research* 16:183-198, Feb. 2012.

Nelson et al., "Survival of synchronized mammalian cells following exposure to cold," *Experimental Cell Research* 70:417-422, 1972.

Rieder et al., "Cold-Shock and the Mammalian Cell Cycle," *Cell Cycle* 1(3): 169-175, 2002.

Non-Final Office Action dated Dec. 7, 2022, for co-pending U.S. Appl. No. 16/094,587, 28 pages.

Chinese Office Action dated Jan. 20, 2023 for co-pending Chinese Application No. 20178003864.0 w/English Translation, 6 pages.

Chinese Office Action dated Feb. 20, 2023 for co-pending Chinese Application No. 202010159183.7 w/English Translation, 20 pages.

Guo et al., "Dual nature of the adaptive immune system in lampreys," *Nature* 459:796-801, 2009.

Final Office Action dated May 3, 2023, for co-pending U.S. Appl. No. 15/757,646, 34 pages.

European Communication dated Jun. 21, 2023, for corresponding European Application No. 19196085.5, 4 pages.

Makarova et al., "Evolution and classification of the CRISPR-Cas system," *Nature Reviews* 9:467-477, Jun. 2011.

Non-Final Office Action dated May 24, 2023, for co-pending U.S. Appl. No. 16/838,960, 44 pages.

* cited by examiner

Fig. 10
Fig. 10A
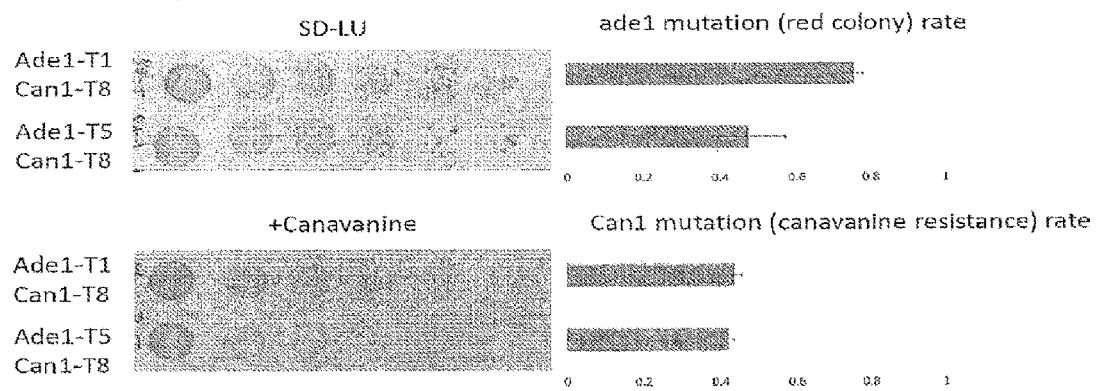
Fig. 10B
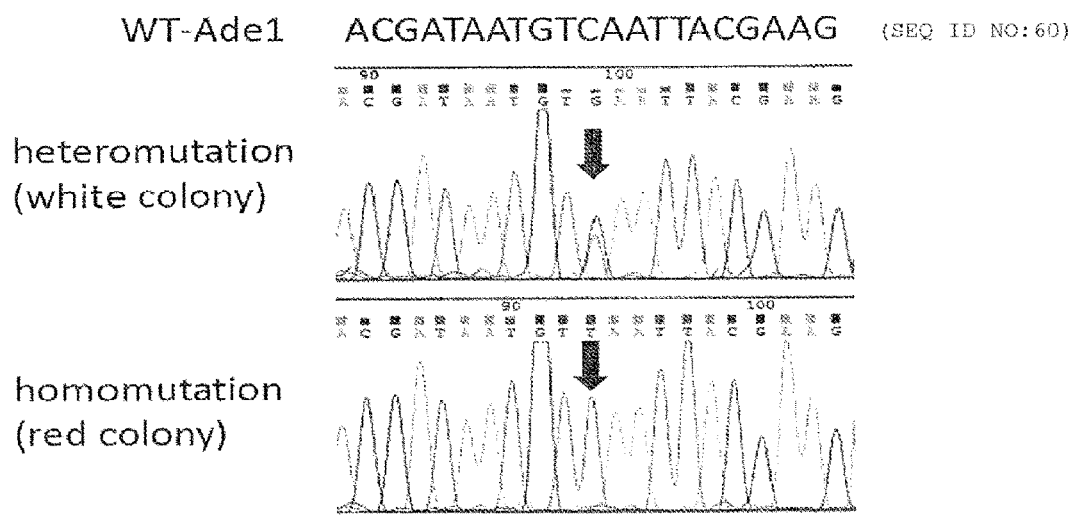

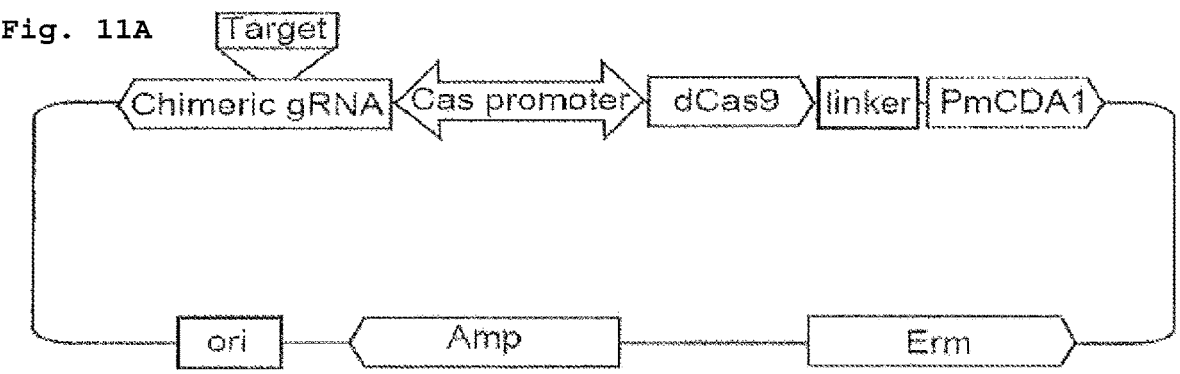

Fig. 11B

```
galK  TCAATGGGCTAACTACGTTC-3'    (SEQ ID NO:61)
   1  TCAATGGGCTAACTACGTTC       (SEQ ID NO:61)
   2  TTAATGGGCTAACTACGTTC       (SEQ ID NO:62)
   3  TTAATGGGCTAACTACGTTC       (SEQ ID NO:62)
```

Fig. 11C

```
rpoB  GCTGTCTCAGTTTATGGACC-3'    (SEQ ID NO:63)
     [CGACAGAGTCAAATACCTGG-5']   (SEQ ID NO:64)

none  1  GCTGTCTCAGTTTATGGACC    (SEQ ID NO:63)
      2  GCTGTCTCAGTTTATGGACC    (SEQ ID NO:63)
Rif25 1  GCTGTCTCAGTTTATGAACC    (SEQ ID NO:66)
      2  GCTGTCTCAGTTTATGAACC    (SEQ ID NO:66)
Rif50 1  GCTGTCTCAGTTTATAAACC    (SEQ ID NO:67)
      2  GCTGTCTCAGTTTATGAACC    (SEQ ID NO:66)
     [CGACAGAGTCAAATACTTGG-5']   (SEQ ID NO:68)
```

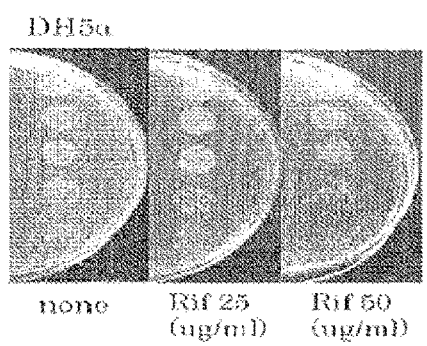

DH5α none | Rif 25 (ug/ml) | Rif 50 (ug/ml)

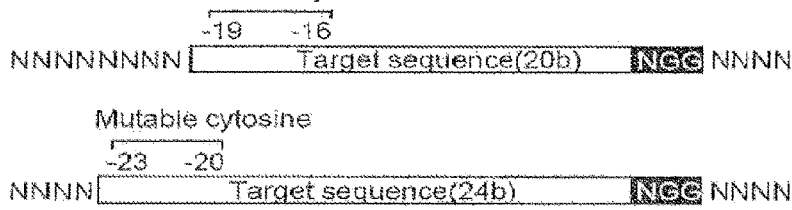

Fig. 12B

```
         TCGCTTGAACATCCAGCGAAACAGGCCCCCCCATCGAGCAGAAAACGGTGGTGGATGGC (SEQ ID NO:69)
target 24bp
         TCGCTTGAACATCCAGCGAAACAGGcCCCCCCATCGAGCAGAAAACGGTGGTGGATGGC (SEQ ID NO:70)
         TCGCTTGAACATCCAGCGAAACAGGCcCCCCCATCGAGCAGAAAACGGTGGTGGATGGC (SEQ ID NO:71)
         TCGCTTGAACATCCAGCGAAACAGGcCCCCCCATCGAGCAGAAAACGGTGGTGGATGGC (SEQ ID NO:72)
         TCGCTTGAACATCCAGCGAAACAGGcCcCCCCATCGAGCAGAAAACGGTGGTGGATGGC (SEQ ID NO:73)
         TCGCTTGAACATCCAGCGAAACAGGcCcCCCCATCGAGCAGAAAACGGTGGTGGATGGC (SEQ ID NO:74)
target 22bp
         TCGCTTGAACATCCAGCGAAACAGGcccCCCCATCGAGCAGAAAACGGTGGTGGATGGC (SEQ ID NO:75)
         TCGCTTGAACATCCAGCGAAACAGGcccCCCCATCGAGCAGAAAACGGTGGTGGATGGC (SEQ ID NO:76)
         TCGCTTGAACATCCAGCGAAACAGGcCcCCCCATCGAGCAGAAAACGGTGGTGGATGGC (SEQ ID NO:77)
         TCGCTTGAACATCCAGCGAAACAGGcC cCCCCATCGAGCAGAAAACGGTGGTGGATGGC (SEQ ID NO:78)
         TCGCTTGAACATCCAGCGAAACAGGCC CCCCATCGAGCAGAAAACGGTGGTGGATGGC (SEQ ID NO:79)
target 20bp
         TCGCTTGAACATCCAGCGAAACAGGCG CCCCATCGAGCAGAAAACGGTGGTGGATGGC (SEQ ID NO:80)
         TCGCTTGAACATCCAGCGAAACAGGCC CCCCATCGAGCAGAAAACGGTGGTGGATGGC (SEQ ID NO:81)
         TCGCTTGAACATCCAGCGAAACAGGCC CCCCATCGAGCAGAAAACGGTGGTGGATGGC (SEQ ID NO:82)
         TCGCTTGAACATCCAGCGAAACAGGCCcccCCCCATCGAGCAGAAAACGGTGGTGGATGGC (SEQ ID NO:83)
target 18bp
         TCGCTTGAACATCCAGCGAAACAGGCC  CCCATCGAGCAGAAAACGGTGGTGGATGGC (SEQ ID NO:84)
         TCGCTTGAACATCCAGCGAAACAGGCCC CCCATCGAGCAGAAAACGGTGGTGGATGGC (SEQ ID NO:85)
         TCGCTTGAACATCCAGCGAAACAGGCCCC CCATCGAGCAGAAAACGGTGGTGGATGGC (SEQ ID NO:86)
         TCGCTTGAACATCCAGCGAAACAGGCCCC CCATCGAGCAGAAAACGGTGGTGGATGGC (SEQ ID NO:87)
         TCGCTTGAACATCCAGCGAAACAGGCCCC CCATCGAGCAGAAAACGGTGGTGGATGGC (SEQ ID NO:88)
         TCGCTTGAACATCCAGCGAAACAGGCCCCcCCCATCGAGCAGAAAACGGTGGTGGATGGC (SEQ ID NO:89)
```

Fig. 16
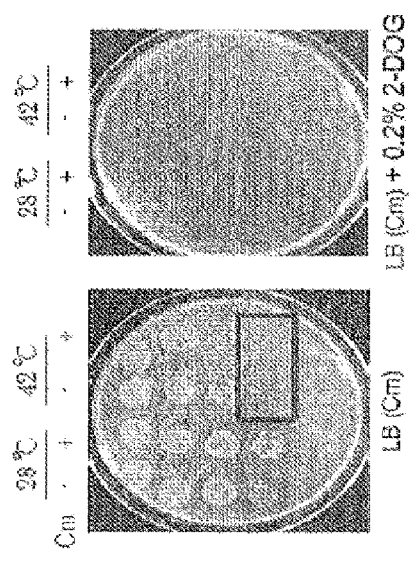
*galK* (target 8)
*galK 8* ACTCACACCATTCAGGCGCC -3' (SEQ ID NO:92)
colony1 ACTTACACCATTCAGGCGCC (SEQ ID NO:93)
colony2 ACTTACACCATTCAGGCGCC (c→t)(SEQ ID NO:93)
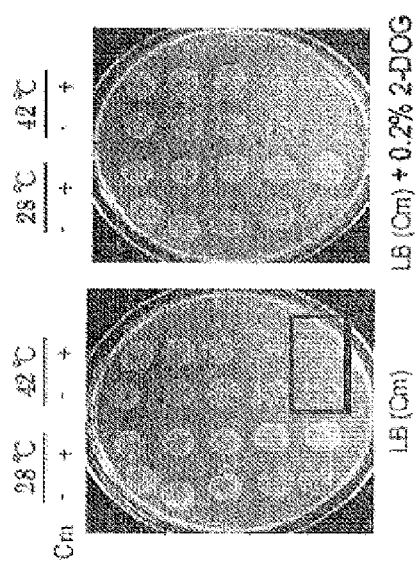
*galK* (target 12)
*galK 12* TCAATGGGCTAACTACGTTCG -3' (SEQ ID NO:94)
colony1 TTAATGGGCTAACTACGTTCG (SEQ ID NO:95)
colony2 TTAATGGGCTAACTACGTTCG (c→t)(SEQ ID NO:95)

SEQUENCE LISTING

<160> NUMBER OF SEQ ID NOS: 95

<210> SEQ ID NO 1
<211> LENGTH: 624
<212> TYPE: DNA
<213> ORGANISM: Petromyzon marinus
<220> FEATURE:
<221> NAME/KEY: CDS
<222> LOCATION: (1)..(624)

<400> SEQUENCE: 1

```
atg acc gac gct gag tac gtg aga atc cat gag aag ttg gac atc tac      48
Met Thr Asp Ala Glu Tyr Val Arg Ile His Glu Lys Leu Asp Ile Tyr
1               5                   10                  15 acg ttt aag aaa cag ttt ttc aac aac aaa aaa tcc gtg tcg cat aga      96
Thr Phe Lys Lys Gln Phe Phe Asn Asn Lys Lys Ser Val Ser His Arg
                20                  25                  30 tgc tac gtt ctc ttt gaa tta aaa cga cgg ggt gaa cgt aga gcg tgt     144
Cys Tyr Val Leu Phe Glu Leu Lys Arg Arg Gly Glu Arg Arg Ala Cys
            35                  40                  45 ttt tgg ggc tat gct gtg aat aaa cca cag agc ggg aca gaa cgt ggc     192
Phe Trp Gly Tyr Ala Val Asn Lys Pro Gln Ser Gly Thr Glu Arg Gly
        50                  55                  60 att cac gcc gaa atc ttt agc att aga aaa gtc gaa gaa tac ctg cgc     240
Ile His Ala Glu Ile Phe Ser Ile Arg Lys Val Glu Glu Tyr Leu Arg
65                  70                  75                  80 gac aac ccc gga caa ttc acg ata aat tgg tac tca tcc tgg agt cct     288
Asp Asn Pro Gly Gln Phe Thr Ile Asn Trp Tyr Ser Ser Trp Ser Pro
                85                  90                  95 tgt gca gat tgc gct gaa aag atc tta gaa tgg tat aac cag gag ctg     336
Cys Ala Asp Cys Ala Glu Lys Ile Leu Glu Trp Tyr Asn Gln Glu Leu
                100                 105                 110 cgg ggg aac ggc cac act ttg aaa atc tgg gct tgc aaa ctc tat tac     384
Arg Gly Asn Gly His Thr Leu Lys Ile Trp Ala Cys Lys Leu Tyr Tyr
            115                 120                 125 gag aaa aat gcg agg aat caa att ggg ctg tgg aac ctc aga gat aac     432
Glu Lys Asn Ala Arg Asn Gln Ile Gly Leu Trp Asn Leu Arg Asp Asn
        130                 135                 140 ggg gtt ggg ttg aat gta atg gta agt gaa cac tac caa tgt tgc agg     480
Gly Val Gly Leu Asn Val Met Val Ser Glu His Tyr Gln Cys Cys Arg
145                 150                 155                 160 aaa ata ttc atc caa tcg tcg cac aat caa ttg aat gag aat aga tgg     528
Lys Ile Phe Ile Gln Ser Ser His Asn Gln Leu Asn Glu Asn Arg Trp
                165                 170                 175 ctt gag aag act ttg aag cga gct gaa aaa cga cgg agc gag ttg tcc     576
Leu Glu Lys Thr Leu Lys Arg Ala Glu Lys Arg Arg Ser Glu Leu Ser
                180                 185                 190 att atg att cag gta aaa ata ctc cac acc act aag agt cct gct gtt     624
```

```
Ile Met Ile Gln Val Lys Ile Leu His Thr Thr Lys Ser Pro Ala Val
        195                 200                 205
```

<210> SEQ ID NO 2
<211> LENGTH: 208
<212> TYPE: PRT
<213> ORGANISM: Petromyzon marinus

<400> SEQUENCE: 2

```
Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205
```

<210> SEQ ID NO 3
<211> LENGTH: 600
<212> TYPE: DNA
<213> ORGANISM: Homo sapiens
<220> FEATURE:
<221> NAME/KEY: CDS
<222> LOCATION: (1)..(600)

<400> SEQUENCE: 3

```
atg gac agc ctc ttg atg aac cgg agg aag ttt ctt tac caa ttc aaa    48
Met Asp Ser Leu Leu Met Asn Arg Arg Lys Phe Leu Tyr Gln Phe Lys
1               5                   10                  15 aat gtc cgc tgg gct aag ggt cgg cgt gag acc tac ctg tgc tac gta    96
Asn Val Arg Trp Ala Lys Gly Arg Arg Glu Thr Tyr Leu Cys Tyr Val
            20                  25                  30 gtg aag agg cgt gac agt gct aca tcc ttt tca ctg gac ttt ggt tat   144
Val Lys Arg Arg Asp Ser Ala Thr Ser Phe Ser Leu Asp Phe Gly Tyr
        35                  40                  45 ctt cgc aat aag aac ggc tgc cac gtg gaa ttg ctc ttc ctc cgc tac   192
Leu Arg Asn Lys Asn Gly Cys His Val Glu Leu Leu Phe Leu Arg Tyr
    50                  55                  60 atc tcg gac tgg gac cta gac cct ggc cgc tgc tac cgc gtc acc tgg   240
Ile Ser Asp Trp Asp Leu Asp Pro Gly Arg Cys Tyr Arg Val Thr Trp
```

```
            65                  70                  75                  80
ttc acc tcc tgg agc ccc tgc tac gac tgt gcc cga cat gtg gcc gac         288
Phe Thr Ser Trp Ser Pro Cys Tyr Asp Cys Ala Arg His Val Ala Asp
                    85                  90                  95 ttt ctg cga ggg aac ccc tac ctc agt ctg agg atc ttc acc gcg cgc         336
Phe Leu Arg Gly Asn Pro Tyr Leu Ser Leu Arg Ile Phe Thr Ala Arg
                100                 105                 110 ctc tac ttc tgt gag gac cgc aag gct gag ccc gag ggg ctg cgg cgg         384
Leu Tyr Phe Cys Glu Asp Arg Lys Ala Glu Pro Glu Gly Leu Arg Arg
            115                 120                 125 ctg cac cgc gcc ggg gtg caa ata gcc atc atg acc ttc aaa gat tat         432
Leu His Arg Ala Gly Val Gln Ile Ala Ile Met Thr Phe Lys Asp Tyr
        130                 135                 140 ttt tac tgc tgg aat act ttt gta gaa aac cat gaa aga act ttc aaa         480
Phe Tyr Cys Trp Asn Thr Phe Val Glu Asn His Glu Arg Thr Phe Lys
145                 150                 155                 160 gcc tgg gaa ggg ctg cat gaa aat tca gtt cgt ctc tcc aga cag ctt         528
Ala Trp Glu Gly Leu His Glu Asn Ser Val Arg Leu Ser Arg Gln Leu
                165                 170                 175 cgg cgc atc ctt ttg ccc ctg tat gag gtt gat gac tta cga gac gca         576
Arg Arg Ile Leu Leu Pro Leu Tyr Glu Val Asp Asp Leu Arg Asp Ala
            180                 185                 190 ttt cgt act ttg gga ctt ctc gac                                          600
Phe Arg Thr Leu Gly Leu Leu Asp
        195                 200

<210> SEQ ID NO 4
<211> LENGTH: 200
<212> TYPE: PRT
<213> ORGANISM: Homo sapiens

<400> SEQUENCE: 4

Met Asp Ser Leu Leu Met Asn Arg Arg Lys Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Tyr Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu Leu Asp
```

-continued

<210> SEQ ID NO 5
<211> LENGTH: 4116
<212> TYPE: DNA
<213> ORGANISM: Artificial Sequence
<220> FEATURE:
<223> OTHER INFORMATION: Streptococcus pyogenes-derived Cas9 CDS
      optimized for eucaryotic expression.
<220> FEATURE:
<221> NAME/KEY: CDS
<222> LOCATION: (1)..(4116)

<400> SEQUENCE: 5

```
atg gac aag aag tac tcc att ggg ctc gat atc ggc aca aac agc gtc      48
Met Asp Lys Lys Tyr Ser Ile Gly Leu Asp Ile Gly Thr Asn Ser Val
1               5                   10                  15 ggt tgg gcc gtc att acg gac gag tac aag gtg ccg agc aaa aaa ttc      96
Gly Trp Ala Val Ile Thr Asp Glu Tyr Lys Val Pro Ser Lys Lys Phe
                20                  25                  30 aaa gtt ctg ggc aat acc gat cgc cac agc ata aag aag aac ctc att     144
Lys Val Leu Gly Asn Thr Asp Arg His Ser Ile Lys Lys Asn Leu Ile
        35                  40                  45 ggc gcc ctc ctg ttc gac tcc ggg gag acg gcc gaa gcc acg cgg ctc     192
Gly Ala Leu Leu Phe Asp Ser Gly Glu Thr Ala Glu Ala Thr Arg Leu
    50                  55                  60 aaa aga aca gca cgg cgc aga tat acc cgc aga aag aat cgg atc tgc     240
Lys Arg Thr Ala Arg Arg Arg Tyr Thr Arg Arg Lys Asn Arg Ile Cys
65                  70                  75                  80 tac ctg cag gag atc ttt agt aat gag atg gct aag gtg gat gac tct     288
Tyr Leu Gln Glu Ile Phe Ser Asn Glu Met Ala Lys Val Asp Asp Ser
                85                  90                  95 ttc ttc cat agg ctg gag gag tcc ttt ttg gtg gag gag gat aaa aag     336
Phe Phe His Arg Leu Glu Glu Ser Phe Leu Val Glu Glu Asp Lys Lys
                100                 105                 110 cac gag cgc cac cca atc ttt ggc aat atc gtg gac gag gtg gcg tac     384
His Glu Arg His Pro Ile Phe Gly Asn Ile Val Asp Glu Val Ala Tyr
        115                 120                 125 cat gaa aag tac cca acc ata tat cat ctg agg aag aag ctt gta gac     432
His Glu Lys Tyr Pro Thr Ile Tyr His Leu Arg Lys Lys Leu Val Asp
    130                 135                 140 agt act gat aag gct gac ttg cgg ttg atc tat ctc gcg ctg gcg cat     480
Ser Thr Asp Lys Ala Asp Leu Arg Leu Ile Tyr Leu Ala Leu Ala His
145                 150                 155                 160 atg atc aaa ttt cgg gga cac ttc ctc atc gag ggg gac ctg aac cca     528
Met Ile Lys Phe Arg Gly His Phe Leu Ile Glu Gly Asp Leu Asn Pro
                165                 170                 175 gac aac agc gat gtc gac aaa ctc ttt atc caa ctg gtt cag act tac     576
Asp Asn Ser Asp Val Asp Lys Leu Phe Ile Gln Leu Val Gln Thr Tyr
                180                 185                 190 aat cag ctt ttc gaa gag aac ccg atc aac gca tcc gga gtt gac gcc     624
Asn Gln Leu Phe Glu Glu Asn Pro Ile Asn Ala Ser Gly Val Asp Ala
        195                 200                 205 aaa gca atc ctg agc gct agg ctg tcc aaa tcc cgg cgg ctc gaa aac     672
Lys Ala Ile Leu Ser Ala Arg Leu Ser Lys Ser Arg Arg Leu Glu Asn
    210                 215                 220 ctc atc gca cag ctc cct ggg gag aag aag aac ggc ctg ttt ggt aat     720
Leu Ile Ala Gln Leu Pro Gly Glu Lys Lys Asn Gly Leu Phe Gly Asn
225                 230                 235                 240 ctt atc gcc ctg tca ctc ggg ctg acc ccc aac ttt aaa tct aac ttc     768
Leu Ile Ala Leu Ser Leu Gly Leu Thr Pro Asn Phe Lys Ser Asn Phe
                245                 250                 255
```

```
gac ctg gcc gaa gat gcc aag ctt caa ctg agc aaa gac acc tac gat    816
Asp Leu Ala Glu Asp Ala Lys Leu Gln Leu Ser Lys Asp Thr Tyr Asp
            260                 265                 270 gat gat ctc gac aat ctg ctg gcc cag atc ggc gac cag tac gca gac    864
Asp Asp Leu Asp Asn Leu Leu Ala Gln Ile Gly Asp Gln Tyr Ala Asp
            275                 280                 285 ctt ttt ttg gcg gca aag aac ctg tca gac gcc att ctg ctg agt gat    912
Leu Phe Leu Ala Ala Lys Asn Leu Ser Asp Ala Ile Leu Leu Ser Asp
            290                 295                 300 att ctg cga gtg aac acg gag atc acc aaa gct ccg ctg agc gct agt    960
Ile Leu Arg Val Asn Thr Glu Ile Thr Lys Ala Pro Leu Ser Ala Ser
305                 310                 315                 320 atg atc aag cgc tat gat gag cac cac caa gac ttg act ttg ctg aag   1008
Met Ile Lys Arg Tyr Asp Glu His His Gln Asp Leu Thr Leu Leu Lys
            325                 330                 335 gcc ctt gtc aga cag caa ctg cct gag aag tac aag gaa att ttc ttc   1056
Ala Leu Val Arg Gln Gln Leu Pro Glu Lys Tyr Lys Glu Ile Phe Phe
            340                 345                 350 gat cag tct aaa aat ggc tac gcc gga tac att gac ggc gga gca agc   1104
Asp Gln Ser Lys Asn Gly Tyr Ala Gly Tyr Ile Asp Gly Gly Ala Ser
            355                 360                 365 cag gag gaa ttt tac aaa ttt att aag ccc atc ttg gaa aaa atg gac   1152
Gln Glu Glu Phe Tyr Lys Phe Ile Lys Pro Ile Leu Glu Lys Met Asp
            370                 375                 380 ggc acc gag gag ctg ctg gta aag ctt aac aga gaa gat ctg ttg cgc   1200
Gly Thr Glu Glu Leu Leu Val Lys Leu Asn Arg Glu Asp Leu Leu Arg
385                 390                 395                 400 aaa cag cgc act ttc gac aat gga agc atc ccc cac cag att cac ctg   1248
Lys Gln Arg Thr Phe Asp Asn Gly Ser Ile Pro His Gln Ile His Leu
            405                 410                 415 ggc gaa ctg cac gct atc ctc agg cgg caa gag gat ttc tac ccc ttt   1296
Gly Glu Leu His Ala Ile Leu Arg Arg Gln Glu Asp Phe Tyr Pro Phe
            420                 425                 430 ttg aaa gat aac agg gaa aag att gag aaa atc ctc aca ttt cgg ata   1344
Leu Lys Asp Asn Arg Glu Lys Ile Glu Lys Ile Leu Thr Phe Arg Ile
            435                 440                 445 ccc tac tat gta ggc ccc ctc gcc cgg gga aat tcc aga ttc gcg tgg   1392
Pro Tyr Tyr Val Gly Pro Leu Ala Arg Gly Asn Ser Arg Phe Ala Trp
450                 455                 460 atg act cgc aaa tca gaa gag acc atc act ccc tgg aac ttc gag gaa   1440
Met Thr Arg Lys Ser Glu Glu Thr Ile Thr Pro Trp Asn Phe Glu Glu
465                 470                 475                 480 gtc gtg gat aag ggg gcc tct gcc cag tcc ttc atc gaa agg atg act   1488
Val Val Asp Lys Gly Ala Ser Ala Gln Ser Phe Ile Glu Arg Met Thr
            485                 490                 495 aac ttt gat aaa aat ctg cct aac gaa aag gtg ctt cct aaa cac tct   1536
Asn Phe Asp Lys Asn Leu Pro Asn Glu Lys Val Leu Pro Lys His Ser
            500                 505                 510 ctg ctg tac gag tac ttc aca gtt tat aac gag ctc acc aag gtc aaa   1584
Leu Leu Tyr Glu Tyr Phe Thr Val Tyr Asn Glu Leu Thr Lys Val Lys
            515                 520                 525 tac gtc aca gaa ggg atg aga aag cca gca ttc ctg tct gga gag cag   1632
Tyr Val Thr Glu Gly Met Arg Lys Pro Ala Phe Leu Ser Gly Glu Gln
            530                 535                 540 aag aaa gct atc gtg gac ctc ctc ttc aag acg aac cgg aaa gtt acc   1680
Lys Lys Ala Ile Val Asp Leu Leu Phe Lys Thr Asn Arg Lys Val Thr
545                 550                 555                 560 gtg aaa cag ctc aaa gaa gac tat ttc aaa aag att gaa tgt ttc gac   1728
Val Lys Gln Leu Lys Glu Asp Tyr Phe Lys Lys Ile Glu Cys Phe Asp
```

|   |   |   |   |   |   |   |   |   |   |   |   |   |   |   |   |
|---|---|---|---|---|---|---|---|---|---|---|---|---|---|---|---|
|   |   |   | 565 |   |   |   |   | 570 |   |   |   |   | 575 |   |   |
| tct | gtt | gaa | atc | agc | gga | gtg | gag | gat | cgc | ttc | aac | gca | tcc | ctg | gga |
| Ser | Val | Glu | Ile | Ser | Gly | Val | Glu | Asp | Arg | Phe | Asn | Ala | Ser | Leu | Gly |
|   |   |   | 580 |   |   |   |   | 585 |   |   |   |   | 590 |   |   |

1776 acg tat cac gat ctc ctg aaa atc att aaa gac aag gac ttc ctg gac    1824
Thr Tyr His Asp Leu Leu Lys Ile Ile Lys Asp Lys Asp Phe Leu Asp
            595                 600                 605 aat gag gag aac gag gac att ctt gag gac att gtc ctc acc ctt acg    1872
Asn Glu Glu Asn Glu Asp Ile Leu Glu Asp Ile Val Leu Thr Leu Thr
        610                 615                 620 ttg ttt gaa gat agg gag atg att gaa gaa cgc ttg aaa act tac gct    1920
Leu Phe Glu Asp Arg Glu Met Ile Glu Glu Arg Leu Lys Thr Tyr Ala
625                 630                 635                 640 cat ctc ttc gac gac aaa gtc atg aaa cag ctc aag agg cgc cga tat    1968
His Leu Phe Asp Asp Lys Val Met Lys Gln Leu Lys Arg Arg Arg Tyr
                645                 650                 655 aca gga tgg ggg cgg ctg tca aga aaa ctg atc aat ggg atc cga gac    2016
Thr Gly Trp Gly Arg Leu Ser Arg Lys Leu Ile Asn Gly Ile Arg Asp
            660                 665                 670 aag cag agt gga aag aca atc ctg gat ttt ctt aag tcc gat gga ttt    2064
Lys Gln Ser Gly Lys Thr Ile Leu Asp Phe Leu Lys Ser Asp Gly Phe
        675                 680                 685 gcc aac cgg aac ttc atg cag ttg atc cat gat gac tct ctc acc ttt    2112
Ala Asn Arg Asn Phe Met Gln Leu Ile His Asp Asp Ser Leu Thr Phe
690                 695                 700 aag gag gac atc cag aaa gca caa gtt tct ggc cag ggg gac agt ctt    2160
Lys Glu Asp Ile Gln Lys Ala Gln Val Ser Gly Gln Gly Asp Ser Leu
705                 710                 715                 720 cac gag cac atc gct aat ctt gca ggt agc cca gct atc aaa aag gga    2208
His Glu His Ile Ala Asn Leu Ala Gly Ser Pro Ala Ile Lys Lys Gly
                725                 730                 735 ata ctg cag acc gtt aag gtc gtg gat gaa ctc gtc aaa gta atg gga    2256
Ile Leu Gln Thr Val Lys Val Val Asp Glu Leu Val Lys Val Met Gly
            740                 745                 750 agg cat aag ccc gag aat atc gtt atc gag atg gcc cga gag aac caa    2304
Arg His Lys Pro Glu Asn Ile Val Ile Glu Met Ala Arg Glu Asn Gln
        755                 760                 765 act acc cag aag gga cag aag aac agt agg gaa agg atg aag agg att    2352
Thr Thr Gln Lys Gly Gln Lys Asn Ser Arg Glu Arg Met Lys Arg Ile
770                 775                 780 gaa gag ggt ata aaa gaa ctg ggg tcc caa atc ctt aag gaa cac cca    2400
Glu Glu Gly Ile Lys Glu Leu Gly Ser Gln Ile Leu Lys Glu His Pro
785                 790                 795                 800 gtt gaa aac acc cag ctt cag aat gag aag ctc tac ctg tac tac ctg    2448
Val Glu Asn Thr Gln Leu Gln Asn Glu Lys Leu Tyr Leu Tyr Tyr Leu
                805                 810                 815 cag aac ggc agg gac atg tac gtg gat cag gaa ctg gac atc aat cgg    2496
Gln Asn Gly Arg Asp Met Tyr Val Asp Gln Glu Leu Asp Ile Asn Arg
            820                 825                 830 ctc tcc gac tac gac gtg gat cat atc gtg ccc cag tct ttt ctc aaa    2544
Leu Ser Asp Tyr Asp Val Asp His Ile Val Pro Gln Ser Phe Leu Lys
        835                 840                 845 gat gat tct att gat aat aaa gtg ttg aca aga tcc gat aaa aat aga    2592
Asp Asp Ser Ile Asp Asn Lys Val Leu Thr Arg Ser Asp Lys Asn Arg
850                 855                 860 ggg aag agt gat aac gtc ccc tca gaa gaa gtt gtc aag aaa atg aaa    2640
Gly Lys Ser Asp Asn Val Pro Ser Glu Glu Val Val Lys Lys Met Lys
865                 870                 875                 880 aat tat tgg cgg cag ctg ctg aac gcc aaa ctg atc aca caa cgg aag    2688

```
                Asn Tyr Trp Arg Gln Leu Leu Asn Ala Lys Leu Ile Thr Gln Arg Lys
                                885                 890                 895 ttc gat aat ctg act aag gct gaa cga ggt ggc ctg tct gag ttg gat            2736
Phe Asp Asn Leu Thr Lys Ala Glu Arg Gly Gly Leu Ser Glu Leu Asp
            900                 905                 910 aaa gcc ggc ttc atc aaa agg cag ctt gtt gag aca cgc cag atc acc            2784
Lys Ala Gly Phe Ile Lys Arg Gln Leu Val Glu Thr Arg Gln Ile Thr
            915                 920                 925 aag cac gtg gcc caa att ctc gat tca cgc atg aac acc aag tac gat            2832
Lys His Val Ala Gln Ile Leu Asp Ser Arg Met Asn Thr Lys Tyr Asp
            930                 935                 940 gaa aat gac aaa ctg att cga gag gtg aaa gtt att act ctg aag tct            2880
Glu Asn Asp Lys Leu Ile Arg Glu Val Lys Val Ile Thr Leu Lys Ser
945                 950                 955                 960 aag ctg gtc tca gat ttc aga aag gac ttt cag ttt tat aag gtg aga            2928
Lys Leu Val Ser Asp Phe Arg Lys Asp Phe Gln Phe Tyr Lys Val Arg
            965                 970                 975 gag atc aac aat tac cac cat gcg cat gat gcc tac ctg aat gca gtg            2976
Glu Ile Asn Asn Tyr His His Ala His Asp Ala Tyr Leu Asn Ala Val
            980                 985                 990 gta ggc act gca ctt atc aaa aaa tat ccc aag ctt gaa tct gaa ttt            3024
Val Gly Thr Ala Leu Ile Lys Lys Tyr Pro Lys Leu Glu Ser Glu Phe
            995                 1000                1005 gtt tac gga gac tat aaa gtg tac gat gtt agg aaa atg atc gca            3069
Val Tyr Gly Asp Tyr Lys Val Tyr Asp Val Arg Lys Met Ile Ala
            1010                1015                1020 aag tct gag cag gaa ata ggc aag gcc acc gct aag tac ttc ttt            3114
Lys Ser Glu Gln Glu Ile Gly Lys Ala Thr Ala Lys Tyr Phe Phe
            1025                1030                1035 tac agc aat att atg aat ttt ttc aag acc gag att aca ctg gcc            3159
Tyr Ser Asn Ile Met Asn Phe Phe Lys Thr Glu Ile Thr Leu Ala
            1040                1045                1050 aat gga gag att cgg aag cga cca ctt atc gaa aca aac gga gaa            3204
Asn Gly Glu Ile Arg Lys Arg Pro Leu Ile Glu Thr Asn Gly Glu
            1055                1060                1065 aca gga gaa atc gtg tgg gac aag ggt agg gat ttc gcg aca gtc            3249
Thr Gly Glu Ile Val Trp Asp Lys Gly Arg Asp Phe Ala Thr Val
            1070                1075                1080 cgg aag gtc ctg tcc atg ccg cag gtg aac atc gtt aaa aag acc            3294
Arg Lys Val Leu Ser Met Pro Gln Val Asn Ile Val Lys Lys Thr
            1085                1090                1095 gaa gta cag acc gga ggc ttc tcc aag gaa agt atc ctc ccg aaa            3339
Glu Val Gln Thr Gly Gly Phe Ser Lys Glu Ser Ile Leu Pro Lys
            1100                1105                1110 agg aac agc gac aag ctg atc gca cgc aaa aaa gat tgg gac ccc            3384
Arg Asn Ser Asp Lys Leu Ile Ala Arg Lys Lys Asp Trp Asp Pro
            1115                1120                1125 aag aaa tac ggc gga ttc gat tct cct aca gtc gct tac agt gta            3429
Lys Lys Tyr Gly Gly Phe Asp Ser Pro Thr Val Ala Tyr Ser Val
            1130                1135                1140 ctg gtt gtg gcc aaa gtg gag aaa ggg aag tct aaa aaa ctc aaa            3474
Leu Val Val Ala Lys Val Glu Lys Gly Lys Ser Lys Lys Leu Lys
            1145                1150                1155 agc gtc aag gaa ctg ctg ggc atc aca atc atg gag cga tca agc            3519
Ser Val Lys Glu Leu Leu Gly Ile Thr Ile Met Glu Arg Ser Ser
            1160                1165                1170 ttc gaa aaa aac ccc atc gac ttt ctc gag gcg aaa gga tat aaa            3564
Phe Glu Lys Asn Pro Ile Asp Phe Leu Glu Ala Lys Gly Tyr Lys
            1175                1180                1185
```

```
gag gtc aaa aaa gac ctc atc att aag ctt ccc aag tac tct ctc      3609
Glu Val Lys Lys Asp Leu Ile Ile Lys Leu Pro Lys Tyr Ser Leu
1190                1195                1200 ttt gag ctt gaa aac ggc cgg aaa cga atg ctc gct agt gcg ggc      3654
Phe Glu Leu Glu Asn Gly Arg Lys Arg Met Leu Ala Ser Ala Gly
1205                1210                1215 gag ctg cag aaa ggt aac gag ctg gca ctg ccc tct aaa tac gtt      3699
Glu Leu Gln Lys Gly Asn Glu Leu Ala Leu Pro Ser Lys Tyr Val
1220                1225                1230 aat ttc ttg tat ctg gcc agc cac tat gaa aag ctc aaa ggg tct      3744
Asn Phe Leu Tyr Leu Ala Ser His Tyr Glu Lys Leu Lys Gly Ser
1235                1240                1245 ccc gaa gat aat gag cag aag cag ctg ttc gtg gaa caa cac aaa      3789
Pro Glu Asp Asn Glu Gln Lys Gln Leu Phe Val Glu Gln His Lys
1250                1255                1260 cac tac ctt gat gag atc atc gag caa ata agc gaa ttc tcc aaa      3834
His Tyr Leu Asp Glu Ile Ile Glu Gln Ile Ser Glu Phe Ser Lys
1265                1270                1275 aga gtg atc ctc gcc gac gct aac ctc gat aag gtg ctt tct gct      3879
Arg Val Ile Leu Ala Asp Ala Asn Leu Asp Lys Val Leu Ser Ala
1280                1285                1290 tac aat aag cac agg gat aag ccc atc agg gag cag gca gaa aac      3924
Tyr Asn Lys His Arg Asp Lys Pro Ile Arg Glu Gln Ala Glu Asn
1295                1300                1305 att atc cac ttg ttt act ctg acc aac ttg ggc gcg cct gca gcc      3969
Ile Ile His Leu Phe Thr Leu Thr Asn Leu Gly Ala Pro Ala Ala
1310                1315                1320 ttc aag tac ttc gac acc acc ata gac aga aag cgg tac acc tct      4014
Phe Lys Tyr Phe Asp Thr Thr Ile Asp Arg Lys Arg Tyr Thr Ser
1325                1330                1335 aca aag gag gtc ctg gac gcc aca ctg att cat cag tca att acg      4059
Thr Lys Glu Val Leu Asp Ala Thr Leu Ile His Gln Ser Ile Thr
1340                1345                1350 ggg ctc tat gaa aca aga atc gac ctc tct cag ctc ggt gga gac      4104
Gly Leu Tyr Glu Thr Arg Ile Asp Leu Ser Gln Leu Gly Gly Asp
1355                1360                1365 agc agg gct gac                                                  4116
Ser Arg Ala Asp
1370

<210> SEQ ID NO 6
<211> LENGTH: 1372
<212> TYPE: PRT
<213> ORGANISM: Artificial Sequence
<220> FEATURE:
<223> OTHER INFORMATION: Synthetic Construct

<400> SEQUENCE: 6

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

```
Phe Phe His Arg Leu Glu Glu Ser Phe Leu Val Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510
```

-continued

Leu Leu Tyr Glu Tyr Phe Thr Val Tyr Asn Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp

```
                930             935             940
Glu Asn Asp Lys Leu Ile Arg Glu Val Lys Val Ile Thr Leu Lys Ser
945                 950             955                 960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
            995             1000            1005

Val Tyr Gly Asp Tyr Lys Val Tyr Asp Val Arg Lys Met Ile Ala
        1010            1015            1020

Lys Ser Glu Gln Glu Ile Gly Lys Ala Thr Ala Lys Tyr Phe Phe
        1025            1030            1035

Tyr Ser Asn Ile Met Asn Phe Phe Lys Thr Glu Ile Thr Leu Ala
        1040            1045            1050

Asn Gly Glu Ile Arg Lys Arg Pro Leu Ile Glu Thr Asn Gly Glu
        1055            1060            1065

Thr Gly Glu Ile Val Trp Asp Lys Gly Arg Asp Phe Ala Thr Val
        1070            1075            1080

Arg Lys Val Leu Ser Met Pro Gln Val Asn Ile Val Lys Lys Thr
        1085            1090            1095

Glu Val Gln Thr Gly Gly Phe Ser Lys Glu Ser Ile Leu Pro Lys
        1100            1105            1110

Arg Asn Ser Asp Lys Leu Ile Ala Arg Lys Lys Asp Trp Asp Pro
        1115            1120            1125

Lys Lys Tyr Gly Gly Phe Asp Ser Pro Thr Val Ala Tyr Ser Val
        1130            1135            1140

Leu Val Val Ala Lys Val Glu Lys Gly Lys Ser Lys Lys Leu Lys
        1145            1150            1155

Ser Val Lys Glu Leu Leu Gly Ile Thr Ile Met Glu Arg Ser Ser
        1160            1165            1170

Phe Glu Lys Asn Pro Ile Asp Phe Leu Glu Ala Lys Gly Tyr Lys
        1175            1180            1185

Glu Val Lys Lys Asp Leu Ile Ile Lys Leu Pro Lys Tyr Ser Leu
        1190            1195            1200

Phe Glu Leu Glu Asn Gly Arg Lys Arg Met Leu Ala Ser Ala Gly
        1205            1210            1215

Glu Leu Gln Lys Gly Asn Glu Leu Ala Leu Pro Ser Lys Tyr Val
        1220            1225            1230

Asn Phe Leu Tyr Leu Ala Ser His Tyr Glu Lys Leu Lys Gly Ser
        1235            1240            1245

Pro Glu Asp Asn Glu Gln Lys Gln Leu Phe Val Glu Gln His Lys
        1250            1255            1260

His Tyr Leu Asp Glu Ile Ile Glu Gln Ile Ser Glu Phe Ser Lys
        1265            1270            1275

Arg Val Ile Leu Ala Asp Ala Asn Leu Asp Lys Val Leu Ser Ala
        1280            1285            1290

Tyr Asn Lys His Arg Asp Lys Pro Ile Arg Glu Gln Ala Glu Asn
        1295            1300            1305

Ile Ile His Leu Phe Thr Leu Thr Asn Leu Gly Ala Pro Ala Ala
        1310            1315            1320

Phe Lys Tyr Phe Asp Thr Thr Ile Asp Arg Lys Arg Tyr Thr Ser
        1325            1330            1335
```

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Arg Ala Asp
    1370

<210> SEQ ID NO 7
<211> LENGTH: 83
<212> TYPE: DNA
<213> ORGANISM: Streptococcus pyogenes

<400> SEQUENCE: 7
gttttagagc tagaaatagc aagttaaaat aaggctagtc cgttatcaac ttgaaaaagt      60
ggcaccgagt cggtggtgct ttt                                              83

<210> SEQ ID NO 8
<211> LENGTH: 665
<212> TYPE: DNA
<213> ORGANISM: Saccharomyces cerevisiae

<400> SEQUENCE: 8
tttcaaaaat tcttactttt tttttggatg gacgcaaaga agtttaataa tcatattaca      60
tggcattacc accatataca tatccatata catatccata tctaatctta cttatatgtt     120
gtggaaatgt aaagagcccc attatcttag cctaaaaaaa ccttctcttt ggaactttca     180
gtaatacgct taactgctca ttgctatatt gaagtacgga ttagaagccg ccgagcgggt     240
gacagccctc cgaaggaaga ctctcctccg tgcgtcctcg tcttcaccgg tcgcgttcct     300
gaaacgcaga tgtgcctcgc gccgcactgc tccgaacaat aaagattcta caatactagc     360
ttttatggtt atgaagagga aaaattggca gtaacctggc cccacaaacc ttcaaatgaa     420
cgaatcaaat taacaaccat aggatgataa tgcgattagt tttttagcct tatttctggg     480
gtaattaatc agcgaagcga tgatttttga tctattaaca gatatataaa tgcaaaaact     540
gcataaccac tttaactaat actttcaaca ttttcggttt gtattacttc ttattcaaat     600
gtaataaaag tatcaacaaa aaattgttaa tatacctcta cactttaacg tcaaggagaa     660
aaaac                                                                 665

<210> SEQ ID NO 9
<211> LENGTH: 21
<212> TYPE: DNA
<213> ORGANISM: Artificial Sequence
<220> FEATURE:
<223> OTHER INFORMATION: Nuclear transition signal.
<220> FEATURE:
<221> NAME/KEY: CDS
<222> LOCATION: (1)..(21)

<400> SEQUENCE: 9 ccc aag aag aag agg aag gtg                                            21
Pro Lys Lys Lys Arg Lys Val
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 10

Pro Lys Lys Lys Arg Lys Val
1               5

<210> SEQ ID NO 11
<211> LENGTH: 15
<212> TYPE: DNA
<213> ORGANISM: Artificial Sequence
<220> FEATURE:
<223> OTHER INFORMATION: GS linker
<220> FEATURE:
<221> NAME/KEY: CDS
<222> LOCATION: (1)..(15)

<400> SEQUENCE: 11 ggt gga gga ggt tct                                                 15
Gly Gly Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Gly Gly Gly Gly Ser
1               5

<210> SEQ ID NO 13
<211> LENGTH: 66
<212> TYPE: DNA
<213> ORGANISM: Artificial Sequence
<220> FEATURE:
<223> OTHER INFORMATION: Flag tag
<220> FEATURE:
<221> NAME/KEY: CDS
<222> LOCATION: (1)..(66)

<400> SEQUENCE: 13 gac tat aag gac cac gac gga gac tac aag gat cat gat att gat tac    48
Asp Tyr Lys Asp His Asp Gly Asp Tyr Lys Asp His Asp Ile Asp Tyr
1               5                   10                  15 aaa gac gat gac gat aag                                             66
Lys Asp Asp Asp Asp Lys
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic Construct

<400> SEQUENCE: 14

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 15
<211> LENGTH: 24
<212> TYPE: DNA
<213> ORGANISM: Artificial Sequence
<220> FEATURE:
<223> OTHER INFORMATION: Strep-tag
```

```
<220> FEATURE:
<221> NAME/KEY: CDS
<222> LOCATION: (1)..(24)

<400> SEQUENCE: 15 tgg agc cac ccg cag ttc gaa aaa                                    24
Trp Ser His Pro Gln Phe Glu Lys
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Trp Ser His Pro Gln Phe Glu Lys
1               5

<210> SEQ ID NO 17
<211> LENGTH: 171
<212> TYPE: DNA
<213> ORGANISM: Artificial Sequence
<220> FEATURE:
<223> OTHER INFORMATION: SH3 domain
<220> FEATURE:
<221> NAME/KEY: CDS
<222> LOCATION: (1)..(171)

<400> SEQUENCE: 17 gca gag tat gtg cgg gcc ctc ttt gac ttt aat ggg aat gat gaa gaa    48
Ala Glu Tyr Val Arg Ala Leu Phe Asp Phe Asn Gly Asn Asp Glu Glu
1               5                   10                  15 gat ctt ccc ttt aag aaa gga gac atc ctg aga atc cgg gat aag cct    96
Asp Leu Pro Phe Lys Lys Gly Asp Ile Leu Arg Ile Arg Asp Lys Pro
            20                  25                  30 gaa gag cag tgg tgg aat gca gag gac agc gaa gga aag agg ggg atg   144
Glu Glu Gln Trp Trp Asn Ala Glu Asp Ser Glu Gly Lys Arg Gly Met
        35                  40                  45 att cct gtc cct tac gtg gag aag tat                                171
Ile Pro Val Pro Tyr Val Glu Lys Tyr
    50                  55

<210> SEQ ID NO 18
<211> LENGTH: 57
<212> TYPE: PRT
<213> ORGANISM: Artificial Sequence
<220> FEATURE:
<223> OTHER INFORMATION: Synthetic Construct

<400> SEQUENCE: 18

Ala Glu Tyr Val Arg Ala Leu Phe Asp Phe Asn Gly Asn Asp Glu Glu
1               5                   10                  15

Asp Leu Pro Phe Lys Lys Gly Asp Ile Leu Arg Ile Arg Asp Lys Pro
            20                  25                  30

Glu Glu Gln Trp Trp Asn Ala Glu Asp Ser Glu Gly Lys Arg Gly Met
        35                  40                  45

Ile Pro Val Pro Tyr Val Glu Lys Tyr
    50                  55

<210> SEQ ID NO 19
<211> LENGTH: 188
<212> TYPE: DNA
<213> ORGANISM: Saccharomyces cerevisiae
```

```
<400> SEQUENCE: 19
gcgaatttct tatgatttat gatttttatt attaaataag ttataaaaaa aataagtgta      60
tacaaatttt aaagtgactc ttaggtttta aaacgaaaat tcttattctt gagtaactct     120
ttcctgtagg tcaggttgct ttctcaggta tagcatgagg tcgctcttat tgaccacacc     180
tctaccgg                                                             188

<210> SEQ ID NO 20
<211> LENGTH: 417
<212> TYPE: DNA
<213> ORGANISM: Saccharomyces cerevisiae

<400> SEQUENCE: 20
ataccaggca tggagcttat ctggtccgtt cgagttttcg acgagtttgg agacattctt      60
tatagatgtc cttttttttt aatgatattc gttaaagaac aaaaagtcaa agcagtttaa     120
cctaacacct gttgttgatg ctacttgaaa caaggcttct aggcgaatac ttaaaaaggt     180
aatttcaata gcggtttata tatctgtttg cttttcaaga tattatgtaa acgcacgatg     240
tttttcgccc aggcttttatt ttttttgttg ttgttgtctt ctcgaagaat tttctcgggc     300
agatctttgt cggaatgtaa aaaagcgcgt aattaaactt tctattatgc tgactaaaat     360
ggaagtgatc accaaaggct atttctgatt atataatcta gtcattactc gctcgag        417

<210> SEQ ID NO 21
<211> LENGTH: 33
<212> TYPE: DNA
<213> ORGANISM: Artificial Sequence
<220> FEATURE:
<223> OTHER INFORMATION: SH3-binding ligand
<220> FEATURE:
<221> NAME/KEY: CDS
<222> LOCATION: (1)..(33)

<400> SEQUENCE: 21 cct cca cct gct ctg cca cct aag aga agg aga                           33
Pro Pro Pro Ala Leu Pro Pro Lys Arg Arg Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Pro Pro Pro Ala Leu Pro Pro Lys Arg Arg Arg
1               5                   10

<210> SEQ ID NO 23
<211> LENGTH: 269
<212> TYPE: DNA
<213> ORGANISM: Saccharomyces cerevisiae

<400> SEQUENCE: 23
tctttgaaaa dataatgtat gattatgctt tcactcatat ttatacagaa acttgatgtt      60
ttctttcgag tatatacaag gtgattacat gtacgtttga agtacaactc tagattttgt     120
agtgccctct tgggctagcg gtaaaggtgc gcattttttc acaccctaca atgttctgtt     180
caaaagattt tggtcaaacg ctgtagaagt gaaagttggt gcgcatgttt cggcgttcga     240
```

```
aacttctccg cagtgaaaga taaatgatc                                      269

<210> SEQ ID NO 24
<211> LENGTH: 14
<212> TYPE: DNA
<213> ORGANISM: Saccharomyces cerevisiae

<400> SEQUENCE: 24 tgtttttttat gtct                                                      14

<210> SEQ ID NO 25
<211> LENGTH: 20
<212> TYPE: DNA
<213> ORGANISM: Saccharomyces cerevisiae

<400> SEQUENCE: 25
gatacgttct ctatggagga                                                 20

<210> SEQ ID NO 26
<211> LENGTH: 20
<212> TYPE: DNA
<213> ORGANISM: Saccharomyces cerevisiae

<400> SEQUENCE: 26
ttggagaaac ccaggtgcct                                                 20

<210> SEQ ID NO 27
<211> LENGTH: 20
<212> TYPE: DNA
<213> ORGANISM: Saccharomyces cerevisiae

<400> SEQUENCE: 27
aacccaggtg cctggggtcc                                                 20

<210> SEQ ID NO 28
<211> LENGTH: 20
<212> TYPE: DNA
<213> ORGANISM: Saccharomyces cerevisiae

<400> SEQUENCE: 28
ttggccaagt cattcaattt                                                 20

<210> SEQ ID NO 29
<211> LENGTH: 20
<212> TYPE: DNA
<213> ORGANISM: Saccharomyces cerevisiae

<400> SEQUENCE: 29
ataacggaat ccaactgggc                                                 20

<210> SEQ ID NO 30
<211> LENGTH: 20
<212> TYPE: DNA
<213> ORGANISM: Saccharomyces cerevisiae

<400> SEQUENCE: 30
gtcaattacg aagactgaac                                                 20

<210> SEQ ID NO 31
<211> LENGTH: 19
<212> TYPE: DNA
<213> ORGANISM: Saccharomyces cerevisiae

<400> SEQUENCE: 31
```
gtcaatagga tcccctttt                                            19

<210> SEQ ID NO 32
<211> LENGTH: 10126
<212> TYPE: DNA
<213> ORGANISM: Artificial Sequence
<220> FEATURE:
<223> OTHER INFORMATION: Plasmid carrying dCas9-PmCDA1 fusion protein
      and chimeric RNA targeting galK gene of E.coli
<220> FEATURE:
<221> NAME/KEY: misc_feature
<222> LOCATION: (5561)..(5580)
<223> OTHER INFORMATION: n is a, c, g, or t

<400> SEQUENCE: 32

| | | |
|---|---|---|
| atcgccattc gccattcagg ctgcgcaact gttgggaagg gcgatcggtg cgggcctctt | 60 |
| cgctattacg ccagctggcg aaaggggat gtgctgcaag gcgattaagt tgggtaacgc | 120 |
| cagggttttc ccagtcacga cgttgtaaaa cgacggccag tgaattcgag ctcggtaccc | 180 |
| ggccgcaaac aacagataaa acgaaaggcc cagtctttcg actgagcctt tcgtttttatt | 240 |
| tgatgcctgt caagtaacag caggactctt agtggtgtgg agtattttta cctgaatcat | 300 |
| aatggacaac tcgctccgtc gttttttcagc tcgcttcaaa gtcttctcaa gccatctatt | 360 |
| ctcattcaat tgattgtgcg acgattggat gaatattttc ctgcaacatt ggtagtgttc | 420 |
| acttaccatt acattcaacc caaccccgtt atctctgagg ttccacagcc caatttgatt | 480 |
| cctcgcattt ttctcgtaat agagtttgca gcccagatt tcaaagtgt ggccgttccc | 540 |
| ccgcagctcc tggttatacc attctaagat cttttcagcg caatctgcac aaggactcca | 600 |
| ggatgagtac caatttatcg tgaattgtcc ggggttgtcg cgcaggtatt cttcgacttt | 660 |
| tctaatgcta aagatttcgg cgtgaatgcc acgttctgtc ccgctctgtg gtttattcac | 720 |
| agcatagccc caaaaacacg ctctacgttc accccgtcgt tttaattcaa agagaacgta | 780 |
| gcatctatgc gacacggatt ttttgttgtt gaaaaactgt tcttaaacg tgtagatgtc | 840 |
| caacttctca tggattctca cgtactcagc gtcggtcatc ctagacttat cgtcatcgtc | 900 |
| tttgtaatca atatcatgat ccttgtagtc tccgtcgtgg tccttatagt ctccggactc | 960 |
| gagcctagac ttatcgtcat cgtctttgta atcaatatca tgatccttgt agtctccgtc | 1020 |
| gtggtcctta tagtctccgg aatacttctc cacgtaaggg acaggaatca tcccctcttt | 1080 |
| tccttcgctg tcctctgcat tccaccactg ctcctcaggc ttatcccgga ttctcaggat | 1140 |
| gtctcctttc ttaaagggaa gatcctcttc atcattccca ttaaagtcaa agagggctcg | 1200 |
| cacatactca gcagaacctc cacctccaga acctcctcca ccgtcacctc ctagctgact | 1260 |
| caaatcaatg cgtgtttcat aaagaccagt gatggattga tggataagag tggcatctaa | 1320 |
| aacttctttt gtagacgtat atcgtttacg atcaattgtt gtatcaaaat atttaaaagc | 1380 |
| agcgggagct ccaagattcg tcaacgtaaa taaatgaata atattttctg cttgttcacg | 1440 |
| tattggtttg tctctatgtt tgttatatgc actaagaact ttatctaaat tggcatctgc | 1500 |
| taaaataaca cgcttagaaa attcactgat ttgctcaata atctcatcta ataatgctt | 1560 |
| atgctgctcc acaaacaatt gttttgttc gttatcttct ggactaccct tcaacttttc | 1620 |
| ataatgacta gctaaatata aaaaattcac atatttgctt ggcagagcca gctcatttcc | 1680 |
| tttttgtaat tctccggcac tagccagcat ccgttacga ccgttttcta actcaaaaag | 1740 |
| actatattta ggtagtttaa tgattaagtc ttttttaact tccttatatc ctttagcttc | 1800 |
| taaaaagtca atcggatttt tttcaaagga acttcttcc ataattgtga tccctagtaa | 1860 |

```
ctctttaacg gatttaact tcttcgattt ccctttttcc accttagcaa ccactaggac    1920
tgaataagct accgttggac tatcaaaacc accatatttt tttggatccc agtcttttt    1980 acgagcaata agcttgtccg aatttctttt tggtaaaatt gactccttgg agaatccgcc    2040
tgtctgtact tctgttttct tgacaatatt gacttggggc atggacaata ctttgcgcac    2100
tgtggcaaaa tctcgccctt tatcccagac aatttctcca gtttcccat tagtttcgat    2160 tagagggcgt ttgcgaatct ctccatttgc aagtgtaatt tctgttttga agaagttcat    2220
gatattagag taaagaaat attttgcggt tgctttgcct atttcttgct cagacttagc    2280 aatcattta cgaacatcat aaactttata atcaccatag acaaactccg attcaagttt    2340
tggatatttc ttaatcaaag cagttccaac gacggcattt agatacgcat catgggcatg    2400
atggtaattg ttaatctcac gtactttata gaattggaaa tcttttcgga agtcagaaac    2460
taatttagat tttaaggtaa tcactttaac ctctcgaata agtttatcat tttcatcgta    2520
tttagtattc atgcgactat ccaaaatttg tgccacatgc ttagtgattt ggcgagtttc    2580
aaccaattgg cgtttgataa aaccagcttt atcaagttca ctcaaacctc cacgttcagc    2640
tttcgttaaa ttatcaaact tacgttgagt gattaacttg gcgtttagaa gttgtctcca    2700 atagttttc atcttttga ctacttcttc acttggaacg ttatccgatt taccacgatt    2760
tttatcagaa cgcgttaaga ccttattgtc tattgaatcg tctttaagga aactttgtgg    2820
aacaatggca tcgacatcat aatcacttaa acgattaata tctaattctt ggtccacata    2880
catgtctctt ccatttgga gataatagag atagagcttt tcattttgca attgagtatt    2940
ttcaacagga tgctctttaa gaatctgact tcctaattct ttgatacctt cttcgattcg    3000
tttcatacgc tctcgcgaat ttttctggcc cttttgagtt gtctgatttt cacgtgccat    3060
ttcaataacg atattttctg gcttatgccg ccccattact ttgaccaatt catcaacaac    3120
ttttacagtc tgtaaaatac ctttttttaat agcagggcta ccagctaaat ttgcaatatg    3180
ttcatgtaaa ctatcgcctt gtccagacac ttgtgctttt tgaatgtctt cttaaatgt    3240 caaactatca tcatggatca gctgcataaa attgcgattg gcaaaaccat ctgatttcaa    3300
aaaatctaat attgttttgc cagattgctt atccctaata ccattaatca attttcgaga    3360
caaacgtccc caaccagtat aacggcgacg tttaagctgt ttcatcacct tatcatcaaa    3420
gaggtgagca tatgttttaa gtcttccctc aatcatctcc ctatcttcaa ataaggtcaa    3480
tgttaaaaca atatcctcta agatatcttc attttcttca ttatccaaaa aatctttatc    3540
tttaataatt tttagcaaat catggtaggt acctaatgaa gcattaaatc tatccttcaac    3600 tcctgaaatt tcaacactat caaaacattc tatttttttg aaataatctt cttttaattg    3660
cttaacggtt acttttcgat ttgttttgaa gagtaaatca acaatggctt tcttctgttc    3720
acctgaaaga aatgctggtt ttcgcattcc ttcagtaaca tatttgacct tgtcaattc    3780 gttataaacc gtaaaatact cataaagcaa actatgtttt ggtagtactt tttcatttgg    3840 aagatttta tcaaagtttg tcatgcgttc aataaatgat tgagctgaag cacctttatc    3900
gacaacttct tcaaaattcc atggggtaat tgtttcttca gacttccgag tcatccatgc    3960
aaaacgacta ttgccacgcg ccaatggacc aacataataa ggaattcgaa aagtcaagat    4020 ttttcaatc ttctcacgat tgtctttaa aaatggataa aagtcttctt gtcttctcaa    4080
aatagcatgc agctcaccca agtgaatttg atggggaata gagccgttgt caaaggtccg    4140
ttgcttgcgc agcaaatctt cacgatttag tttcaccaat aattcctcag taccatccat    4200
```

-continued

```
ttttttctaaa attggtttga taaatttata aaattcttct tggctagctc ccccatcaat    4260
ataacctgca tatccgtttt ttgattgatc aaaaaagatt tctttatact tttctggaag    4320
ttgttgtcga actaaagctt ttaaaagagt caagtcttga tgatgttcat cgtagcgttt    4380
aatcattgaa gctgataggg gagccttagt tatttcagta tttactctta ggatatctga    4440
aagtaaaata gcatctgata aattcttagc tgccaaaaac aaatcagcat attgatctcc    4500
aatttgcgcc aataaattat ctaaatcatc atcgtaagta tcttttgaaa gctgtaattt    4560
agcatcttct gccaaatcaa aatttgattt aaaattaggg gtcaaaccca atgacaaagc    4620
aatgagattc ccaaataagc cattttttctt ctcaccgggg agctgagcaa tgagattttc    4680
taatcgtctt gatttactca atcgtgcaga aagaatcgct ttagcatcta ctccacttgc    4740
gttaataggg ttttcttcaa ataattgatt gtaggtttgt accaactgga taaatagttt    4800
gtccacatca ctattatcag gatttaaatc tccctcaatc aaaaaatgac cacgaaactt    4860
aatcatatgc gctaaggcca aatagattaa gcgcaaatcc gctttatcag tagaatctac    4920
caattttttt cgcagatgat agatagttgg atatttctca tgataagcaa cttcatctac    4980
tatatttcca aaaataggat gacgttcatg cttcttgtct tcttccacca aaaaagactc    5040
ttcaagtcga tgaaagaaac tatcatctac tttcgccatc tcatttgaaa aaatctcctg    5100
tagataacaa atacgattct tccgacgtgt ataccttcta cgagctgtcc gtttgagacg    5160
agtcgcttcc gctgtctctc cactgtcaaa taaaagagcc cctataagat tttttttgat    5220
actgtggcgg tctgtatttc ccagaacctt gaactttta gacggaacct tatattcatc    5280
agtgatcacc gcccatccga cgctatttgt gccgatagct aagcctattg agtatttctt    5340
atccattttt gcctcctaaa atgggccctt taaattaaat ccataatgag tttgatgatt    5400
tcaataaatag ttttaatgac ctccgaaatt agtttaatat gctttaattt ttcttttttca    5460
aaatatctct tcaaaaaata ttacccaata cttaataata aatagattat aacacaaaat    5520
tcttttgaca agtagtttat tttgttataa ttctatagta nnnnnnnnnn nnnnnnnnnn    5580
gttttagagc tagaaatagc aagttaaaat aaggctagtc cgttatcaac ttgaaaaagt    5640
ggcaccgagt cggtgctttt tttgatactt ctattctact ctgactgcaa accaaaaaaa    5700
caagcgcttt caaaacgctt gttttatcat ttttagggaa attaatctct taatcctttt    5760
atcattctac atttaggcgc tgccatcttg ctaaacctac taagctccac aggatgattt    5820
cgtaatcccg caagaggccc ggcagtaccg gcataaccaa gcctatgcct acagcatcca    5880
gggtgacggt gccgaggatg acgatgagcg cattgttaga tttcatacac ggtgcctgac    5940
tgcgttagca atttaactgt gataaactac cgcattaaag cttatcgatg ataagctgtc    6000
aaacatgaga attacaactt atatcgtatg gggctgactt caggtgctac atttgaagag    6060
ataaattgca ctgaaatcta gtcggatcct cgctcactga ctcgctgcgc tcggtcgttc    6120
ggctgcggcg agcggtatca gctcactcaa aggcggtaat acggttatcc acagaatcag    6180
gggataacgc aggaaagaac atgtgagcaa aaggccagca aaaggccagg aaccgtaaaa    6240
aggccgcgtt gctggcgttt ttccataggc tccgccccc tgacgagcat cacaaaaatc    6300
gacgctcaag tcagaggtgg cgaaacccga caggactata aagataccag gcgtttcccc    6360
ctggaagctc cctcgtgcgc tctcctgttc cgaccctgcc gcttaccgga tacctgtccg    6420
cctttctccc ttcgggaagc gtggcgcttt ctcatagctc acgctgtagg tatctcagtt    6480
cggtgtaggt cgttcgctcc aagctgggct gtgtgcacga accccccgtt cagcccgacc    6540
gctgcgcctt atccggtaac tatcgtcttg agtccaaccc ggtaagacac gacttatcgc    6600
```

```
cactggcagc agccactggt aacaggatta gcagagcgag gtatgtaggc ggtgctacag      6660
agttcttgaa gtggtggcct aactacggct acactagaag gacagtattt ggtatctgcg      6720
ctctgctgaa gccagttacc ttcggaaaaa gagttggtag ctcttgatcc ggcaaacaaa      6780
ccaccgctgg tagcggtggt ttttttgttt gcaagcagca gattacgcgc agaaaaaaag      6840
gatctcaaga agatcctttg atcttttcta cggggtctga cgctcagtgg aacgaaaact      6900
cacgttaagg gattttggtc atgagattat caaaaaggat cttcacctag atccttttaa      6960
attaaaaatg aagttttaaa tcaatctaaa gtatatatga gtaaacttgg tctgacagtt      7020
accaatgctt aatcagtgag gcacctatct cagcgatctg tctatttcgt tcatccatag      7080
ttgcctgact ccccgtcgtg tagataacta cgatacggga gggcttacca tctggcccca      7140
gtgctgcaat gataccgcga gaaccacgct caccggctcc agatttatca gcaataaacc      7200
agccagccgg aagggccgag cgcagaagtg gtcctgcaac tttatccgcc tccatccagt      7260
ctattaattg ttgccgggaa gctagagtaa gtagttcgcc agttaatagt ttgcgcaacg      7320
ttgttgccat tgctgcaggc atcgtggtgt cacgctcgtc gtttggtatg gcttcattca      7380
gctccggttc ccaacgatca aggcgagtta catgatcccc catgttgtgc aaaaaagcgg      7440
ttagctcctt cggtcctccg atcgttgtca gaagtaagtt ggccgcagtg ttatcactca      7500
tggttatggc agcactgcat aattctctta ctgtcatgcc atccgtaaga tgcttttctg      7560
tgactggtga gtactcaacc aagtcattct gagaatagtg tatgcggcga ccgagttgct      7620
cttgcccggc gtcaacacgg gataataccg cgccacatag cagaacttta aaagtgctca      7680
tcattggaaa acgttcttcg gggcgaaaac tctcaaggat cttaccgctg ttgagatcca      7740
gttcgatgta acccactcgt gcacccaact gatcttcagc atctttttact ttcaccagcg      7800 tttctgggtg agcaaaaaca ggaaggcaaa atgccgcaaa aaagggaata agggcgacac      7860
ggaaatgttg aatactcata ctcttccttt tcaatatta ttgaagcatt tatcagggtt      7920
attgtctcat gagcggatac atatttgaat gtatttagaa aaataaacaa ataggggttc      7980
cgcgcacatt tccccgaaaa gtgccacctg acgtcaatgc cgagcgaaag cgagccgaag      8040
ggtagcattt acgttagata accccctgat atgctccgac gctttatata gaaagaagaa      8100
ttcaactagg taaaatctta atataggttg agatgataag gtttataagg aatttgtttg      8160
ttctaatttt tcactcattt tgttctaatt tcttttaaca aatgttcttt tttttttaga      8220
acagttatga tatagttaga atagtttaaa ataaggagtg agaaaaagat gaaagaaaga      8280 tatgaacag tctataaagg ctctcagagg ctcatagacg aagaaagtgg agaagtcata      8340
gaggtagaca agttataccg taaacaaacg tctggtaact tcgtaaaggc atatatagtg      8400
caattaataa gtatgttaga tatgattggc ggaaaaaaac ttaaaatcgt taactatatc      8460
ctagataatg tccacttaag taacaataca atgatagcta caacaagaga aatagcaaaa      8520
gctacaggaa caagtctaca aacagtaata acaacactta aatcttaga agaaggaaat      8580 attataaaaa gaaaaactgg agtattaatg ttaaaccctg aactactaat gagaggcgac      8640
gaccaaaaac aaaaatacct cttactcgaa tttgggaact ttgagcaaga ggcaaatgaa      8700
atagattgac ctcccaataa caccacgtag ttattgggag gtcaatctat gaaatgcgat      8760
taagcttttt ctaattcaca taagcgtgca ggtttaaagt acataaaaaa tataatgaaa      8820
aaaagcatca ttatactaac gttataccaa cattatactc tcattatact aattgcttat      8880
tccaatttcc tattggttgg aaccaacagg cgttagtgtg ttgttgagtt ggtactttca      8940
```

| | |
|---|---|
| tgggattaat cccatgaaac ccccaaccaa ctcgccaaag ctttggctaa cacacacgcc | 9000 |
| attccaacca atagttttct cggcataaag ccatgctctg acgctttaaat gcactaatgc | 9060 |
| cttaaaaaaa cattaaagtc taacacacta gacttattta cttcgtaatt aagtcgttaa | 9120 |
| accgtgtgct ctacgaccaa aagtataaaa cctttaagaa cttcttttt tcttgtaaaa | 9180 |
| aaagaaacta gataaatctc tcatatcttt tattcaataa tcgcatcaga ttgcagtata | 9240 |
| aatttaacga tcactcatca tgttcatatt tatcagagct cgtgctataa ttatactaat | 9300 |
| tttataagga ggaaaaaata aagagggtta taatgaacga gaaaaatata aaacacagtc | 9360 |
| aaaactttat tacttcaaaa cataatatag ataaaataat gacaaatata agattaaatg | 9420 |
| aacatgataa tatctttgaa atcggctcag gaaaagggca ttttacccctt gaattagtac | 9480 |
| agaggtgtaa tttcgtaact gccattgaaa tagaccataa attatgcaaa actacagaaa | 9540 |
| ataaacttgt tgatcacgat aatttccaag ttttaaacaa ggatatattg cagtttaaat | 9600 |
| ttcctaaaaa ccaatcctat aaaatatttg gtaatatacc ttataacata agtacggata | 9660 |
| taatacgcaa aattgttttt gatagtatag ctgatgagat ttatttaatc gtggaatacg | 9720 |
| ggtttgctaa aagattatta aatacaaaac gctcattggc attattttta atggcagaag | 9780 |
| ttgatatttc tatattaagt atggttccaa gagaatattt tcatcctaaa cctaaagtga | 9840 |
| atagctcact tatcagatta aatagaaaaa aatcaagaat atcacacaaa gataaacaga | 9900 |
| agtataatta tttcgttatg aaatgggtta acaaagaata caagaaaata tttacaaaaa | 9960 |
| atcaatttaa caattcctta aaacatgcag gaattgacga tttaaacaat attagctttg | 10020 |
| aacaattctt atctcttttc aatagctata aattatttaa taagtaagtt aagggatgca | 10080 |
| taaactgcat cccttaactt gttttcgtg tacctatttt ttgtga | 10126 |

<210> SEQ ID NO 33
<211> LENGTH: 20
<212> TYPE: DNA
<213> ORGANISM: Escherichia coli

<400> SEQUENCE: 33

| | |
|---|---|
| tcaatgggct aactacgttc | 20 |

<210> SEQ ID NO 34
<211> LENGTH: 20
<212> TYPE: DNA
<213> ORGANISM: Escherichia coli

<400> SEQUENCE: 34

| | |
|---|---|
| ggtccataaa ctgagacagc | 20 |

<210> SEQ ID NO 35
<211> LENGTH: 223
<212> TYPE: DNA
<213> ORGANISM: Escherichia coli

<400> SEQUENCE: 35

| | |
|---|---|
| gagttataca cagggctggg atctattctt tttatctttt tttattcttt ctttattcta | 60 |
| taaattataa ccacttgaat ataaacaaaa aaaacacaca aaggtctagc ggaatttaca | 120 |
| gagggtctag cagaatttac aagttttcca gcaaaggtct agcagaattt acagataccc | 180 |
| acaactcaaa ggaaaaggac tagtaattat cattgactag ccc | 223 |

<210> SEQ ID NO 36
<211> LENGTH: 951

<212> TYPE: DNA
<213> ORGANISM: Escherichia coli

<400> SEQUENCE: 36

```
atgtctgaat tagttgtttt caaagcaaat gaactagcga ttagtcgcta tgacttaacg      60
gagcatgaaa ccaagctaat tttatgctgt gtggcactac tcaacccccac gattgaaaac    120
cctacaatga agaacggac ggtatcgttc acttataacc aatacgttca gatgatgaac      180
atcagtaggg aaaatgctta tggtgtatta gctaaagcaa ccagagagct gatgacgaga    240
actgtggaaa tcaggaatcc tttggttaaa ggctttgaga ttttccagtg acaaactat      300
gccaagttct caagcgaaaa attagaatta gttttagtg aagagatatt gccttatctt      360
ttccagttaa aaaaattcat aaatatataat ctggaacatg ttaagtcttt tgaaaacaaa    420
tactctatga ggatttatga gtggttatta aagaactaa cacaaaagaa aactcacaag      480
gcaaatatag agattagcct tgatgaattt aagttcatgt taatgcttga aataactac      540
catgagttta aaggcttaa ccaatgggtt ttgaaaccaa taagtaaaga tttaaacact      600
tacagcaata tgaaattggt ggttgataag cgaggccgcc cgactgatac gttgattttc      660
caagttgaac tagatagaca aatggatctc gtaaccgaac ttgagaacaa ccagataaaa    720
atgaatggtg acaaaatacc aacaaccatt acatcagatt cctacctaca taacggacta    780
agaaaaacac tacacgatgc tttaactgca aaaattcagc tcaccagttt tgaggcaaaa    840
tttttgagtg acatgcaaag taagcatgat ctcaatggtt cgttctcatg gctcacgcaa      900
aaacaacgaa ccacactaga gaacatactg gctaaatacg gaaggatctg a            951
```

<210> SEQ ID NO 37
<211> LENGTH: 714
<212> TYPE: DNA
<213> ORGANISM: Bacteriophage lambda

<400> SEQUENCE: 37

```
tcagccaaac gtctcttcag gccactgact agcgataact tccccacaa cggaacaact       60
ctcattgcat gggatcattg ggtactgtgg gtttagtggt tgtaaaaaca cctgaccgct    120
atccctgatc agtttcttga aggtaaactc atcacccca agtctggcta tgcagaaatc      180
acctggctca acagcctgct cagggtcaac gagaattaac attccgtcag gaaagcttgg    240
cttggagcct gttggtgcgg tcatggaatt accttcaacc tcaagccaga atgcagaatc      300
actggctttt ttggttgtgc ttacccatct ctccgcatca cctttggtaa aggttctaag    360
cttaggtgag aacatccctg cctgaacatg agaaaaaaca gggtactcat actcacttct      420
aagtgacggc tgcatactaa ccgcttcata catctcgtag atttctctgg cgattgaagg      480
gctaaattct tcaacgctaa ctttgagaat ttttgtaagc aatgcggcgt tataagcatt    540
taatgcattg atgccattaa ataaagcacc aacgcctgac tgccccatcc ccatcttgtc      600
tgcgacagat tcctgggata agccaagttc attttttcttt ttttcataaa ttgctttaag    660
gcgacgtgcg tcctcaagct gctcttgtgt taatggtttc tttttttgtgc tcat           714
```

<210> SEQ ID NO 38
<211> LENGTH: 5097
<212> TYPE: DNA
<213> ORGANISM: Artificial Sequence
<220> FEATURE:
<223> OTHER INFORMATION: dCas9-PmCDA1

<400> SEQUENCE: 38

-continued

```
atggataaga aatactcaat aggcttagct atcggcacaa atagcgtcgg atgggcggtg      60
atcactgatg aatataaggt tccgtctaaa aagttcaagg ttctgggaaa tacagaccgc     120
cacagtatca aaaaaatct tataggggct cttttatttg acagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt cttttttggt ggaagaagac aagaagcatg aacgtcatcc tattttggga     360
aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt ttcgtggtca ttttttgatt gagggagatt taaatcctga taatagtgat     540
gtggacaaac tatttatcca gttggtacaa acctacaatc aattatttga agaaaaccct     600
attaacgcaa gtgagtaga tgctaaagcg attctttctg cacgattgag taaatcaaga     660
cgattagaaa atctcattgc tcagctcccc ggtgagaaga aaaatggctt atttgggaat     720
ctcattgctt tgtcattggg tttgacccct aattttaaat caaattttga tttggcagaa     780
gatgctaaat tacagctttc aaaagatact tacgatgatg atttagataa tttattggcg     840
caaattggag atcaatatgc tgatttgttt ttggcagcta agaatttatc agatgctatt     900
ttactttcag atatcctaag agtaaatact gaataacta aggctcccct atcagcttca     960
atgattaaac gctacgatga acatcatcaa gacttgactc ttttaaaagc tttagttcga    1020
caacaacttc cagaaaagta taagaaaatc ttttttgatc aatcaaaaaa cggatatgca    1080
ggttatattg atgggggagc tagccaagaa gaatttata aatttatcaa accaatttta    1140
gaaaaaatgg atggtactga ggaattattg gtgaaactaa atcgtgaaga tttgctgcgc    1200
aagcaacgga ccttttgacaa cggctctatt ccccatcaaa ttcacttggg tgagctgcat    1260 gctatttga gaagacaaga agactttat ccattttaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaaatgaag atatcttaga ggatattgtt    1860
ttaacattga ccttatttga agatagggag atgattgagg aaagacttaa aacatatgct    1920
cacctctttg atgataaggt gatgaaacag cttaaacgtc gccgttatac tggttgggga    1980
cgtttgtctc gaaaattgat taatggtatt agggataagc aatctggcaa aacaatatta    2040
gattttttga aatcagatgg ttttgccaat cgcaatttta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaaggtat tttacagact    2220
gtaaaagttg ttgatgaatt ggtcaaagta atgggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
```

```
gttgaaaata ctcaattgca aaatgaaaag ctctatctct attatctcca aaatggaaga    2460
gacatgtatg tggaccaaga attagatatt aatcgtttaa gtgattatga tgtcgatgcc    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat     2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaatttc taagcgtgtt    3840 attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgacggtgga ggaggttctg gaggtggagg ttctgctgag    4140
tatgtgcgag ccctctttga ctttaatggg aatgatgaag aggatcttcc ctttaagaaa    4200
ggagacatcc tgagaatccg ggataagcct gaggagcagt ggtggaatgc agaggacagc    4260
gaaggaaaga gggggatgat tcctgtccct tacgtggaga gtattccgg agactataag    4320 gaccacgacg gagactacaa ggatcatgat attgattaca aagacgatga cgataagtct    4380
aggctcgagt ccggagacta aaggaccac gacggagact acaaggatca tgatattgat    4440
tacaaagacg atgacgataa gtctaggatg accgacgctg agtacgtgag aatccatgag    4500
aagttggaca tctacacgtt taagaaacag tttttcaaca caaaaaaatc cgtgtcgcat    4560
agatgctacg ttctcttga attaaaacga cggggtgaac gtagagcgtg ttttggggc     4620 tatgctgtga ataaaccaca gagcgggaca gaacgtggca ttcacgccga aatctttagc    4680
attagaaaag tcgaagaata cctgcgcgac aaccccggac aattcacgat aaattggtac    4740
```

```
tcatcctgga gtccttgtgc agattgcgct gaaaagatct tagaatggta taaccaggag    4800
ctgcggggga acggccacac tttgaaaatc tgggcttgca aactctatta cgagaaaaat    4860
gcgaggaatc aaattgggct gtggaacctc agagataacg gggttgggtt gaatgtaatg    4920
gtaagtgaac actaccaatg ttgcaggaaa atattcatcc aatcgtcgca caatcaattg    4980
aatgagaata gatggcttga aagactttg aagcgagctg aaaaacgacg gagcgagttg     5040
tccattatga ttcaggtaaa aatactccac accactaaga gtcctgctgt tacttga       5097
```

<210> SEQ ID NO 39
<211> LENGTH: 105
<212> TYPE: DNA
<213> ORGANISM: Escherichia coli

<400> SEQUENCE: 39

```
acgttaaatc tatcaccgca agggataaat atctaacacc gtgcgtgttg actattttac     60
ctctggcggt gataatggtt gcagggccca ttttaggagg caaaa                    105
```

<210> SEQ ID NO 40
<211> LENGTH: 247
<212> TYPE: DNA
<213> ORGANISM: Artificial Sequence
<220> FEATURE:
<223> OTHER INFORMATION: gRNA

<400> SEQUENCE: 40

```
ggtttagcaa gatggcagcg cctaaatgta gaatgataaa aggattaaga gattaatttc     60
cctaaaaatg ataaaacaag cgttttgaaa gcgcttgttt ttttggtttg cagtcagagt    120
agaatagaag tatcaaaaaa agcaccgact cggtgccact ttttcaagtt gataacggac    180
tagccttatt ttaacttgct atttctagct ctaaaactga gaccatcccg ggtctctact    240
gcagaat                                                              247
```

<210> SEQ ID NO 41
<211> LENGTH: 64
<212> TYPE: DNA
<213> ORGANISM: Escherichia coli

<400> SEQUENCE: 41

```
tatcaccgcc agtggtattt atgtcaacac cgccagagat aatttatcac cgcagatggt     60
tatc                                                                 64
```

<210> SEQ ID NO 42
<211> LENGTH: 10867
<212> TYPE: DNA
<213> ORGANISM: Artificial Sequence
<220> FEATURE:
<223> OTHER INFORMATION: Plasmid

<400> SEQUENCE: 42

```
gtcggaactg actaaagtag tgagttatac acagggctgg gatctattct ttttatcttt     60
ttttattctt tctttattct ataaattata accacttgaa tataaacaaa aaaaacacac    120
aaaggtctag cggaatttac agagggtcta gcagaattta caagttttcc agcaaaggtc    180
tagcagaatt tacagatacc cacaactcaa aggaaaagga ctagtaatta tcattgacta    240
gcccatctca attggtatag tgattaaaat cacctagacc aattgagatg tatgtctgaa    300
ttagttgttt tcaaagcaaa tgaactacg attagtcgct atgacttaac ggagcatgaa    360
accaagctaa ttttatgctg tgtggcacta ctcaaccca cgattgaaaa ccctacaatg     420
```

```
aaagaacgga cggtatcgtt cacttataac caatacgttc agatgatgaa catcagtagg    480
gaaaatgctt atggtgtatt agctaaagca accagagagc tgatgacgag aactgtggaa    540
atcaggaatc ctttggttaa aggctttgag attttccagt ggacaaacta tgccaagttc    600
tcaagcgaaa aattagaatt agtttttagt gaagagatat tgccttatct tttccagtta    660
aaaaaattca taaaatataa tctggaacat gttaagtctt ttgaaaacaa atactctatg    720
aggatttatg agtggttatt aaagaactaa cacaaaaga aaactcacaa ggcaaatata    780
gagattagcc ttgatgaatt taagttcatg ttaatgcttg aaaataacta ccatgagttt    840
aaaaggctta accaatgggt tttgaaacca ataagtaaag atttaaacac ttacagcaat    900
atgaaattgg tggttgataa gcgaggccgc ccgactgata cgttgatttt ccaagttgaa    960
ctagatagac aaatggatct cgtaaccgaa cttgagaaca accagataaa aatgaatggt   1020
gacaaaatac caacaaccat tacatcagat tcctacctac ataacggact aagaaaaaca   1080
ctacacgatg ctttaactgc aaaaattcag ctcaccagtt ttgaggcaaa atttttgagt   1140
gacatgcaaa gtaagcatga tctcaatggt tcgttctcat ggctcacgca aaaacaacga   1200
accacactag agaacatact ggctaaatac ggaaggatct gaggttctta tggctcttgt   1260
atctatcagt gaagcatcaa gactaacaaa caaaagtaga acaactgttc accgttacat   1320
atcaaaggga aaactgtcca tatgcacaga gataatctca tgaccaaaac cggtagctag   1380
aggggccgca ttaggcaccc caggctttac actttatgct tccggctcgt ataatgtgtg   1440
gattttgagt taggatccgg cgagattttc aggagctaag gaagctaaaa tggagaaaaa   1500
aatcactgga tataccaccg ttgatatatc ccaatggcat cgtaaagaac attttgaggc   1560
atttcagtca gttgctcaat gtacctataa ccagaccgtt cagctggata ttacggcctt   1620
tttaaagacc gtaaagaaaa ataagcacaa gttttatccg gcctttattc acattcttgc   1680
ccgcctgatg aatgctcatc cggaattccg tatggcaatg aaagacggtg agctggtgat   1740
atgggatagt gttcacccct tgttacaccg ttttccatgag caaactgaaa cgttttcatc   1800
gctctggagt gaataccacg acgatttccg gcagtttcta cacatatatt cgcaagatgt   1860
ggcgtgttac ggtgaaaacc tggcctattt ccctaaaggg tttattgaga atatgttttt   1920
cgtctcagcc aatccctggg tgagtttcac cagttttgat ttaaacgtgg ccaatatgga   1980
caacttcttc gcccccgttt tcaccatggg caaatattat acgcaaggcg acaaggtgct   2040
gatgccgctg gcgattcagg ttcatcatgc cgtctgtgat ggcttccatg tcggcagaat   2100
gcttaatgaa ttacaacagt actgcgatga gtggcagggc ggggcgtaaa cgcgtggatc   2160
cggcttacta aaagccagat aacagtatgc gtatttgcgc gctgattttt gcggtctaga   2220
ggtttagcaa gatggcagcg cctaaatgta gaatgataaa aggattaaga gattaatttc   2280
cctaaaaatg ataaaacaag cgttttgaaa gcgcttgttt ttttggtttg cagtcagagt   2340
agaatagaag tatcaaaaaa agcaccgact cggtgccact ttttcaagtt gataacggac   2400
tagccttatt ttaacttgct atttctagct ctaaaactga gaccatcccg ggtctctact   2460
gcagaattat caccgccagt ggtatttatg tcaacaccgc cagagataat ttatcaccgc   2520
agatggttat cgatgaagat tcttgctcaa ttgttatcag ctatgcgccg accagaacac   2580
cttgccgatc agccaaacgt ctcttcaggc cactgactag cgataacttt ccccacaacg   2640
gaacaactct cattgcatgg gatcattggg tactgtgggt ttagtggttg taaaaacacc   2700
tgaccgctat ccctgatcag tttcttgaag gtaaactcat cacccccaag tctggctatg   2760
```

```
cagaaatcac ctggctcaac agcctgctca gggtcaacga gaattaacat tccgtcagga    2820
aagcttggct tggagcctgt tggtgcggtc atggaattac cttcaacctc aagccagaat    2880
gcagaatcac tggctttttt ggttgtgctt acccatctct ccgcatcacc tttggtaaag    2940
gttctaagct taggtgagaa catccctgcc tgaacatgag aaaaaacagg gtactcatac    3000
tcacttctaa gtgacggctg catactaacc gcttcataca tctcgtagat ttctctggcg    3060
attgaagggc taaattcttc aacgctaact ttgagaattt ttgtaagcaa tgcggcgtta    3120
taagcattta atgcattgat gccattaaat aaagcaccaa cgcctgactg ccccatcccc    3180
atcttgtctg cgacagattc ctgggataag ccaagttcat tttctttttt ttcataaatt    3240
gctttaaggc gacgtgcgtc ctcaagctgc tcttgtgtta atggtttctt ttttgtgctc    3300
atacgttaaa tctatcaccg caagggataa atatctaaca ccgtgcgtgt tgactatttt    3360
acctctggcg gtgataatgg ttgcagggcc cattttagga ggcaaaaatg gataagaaat    3420
actcaatagg cttagctatc ggcacaaata gcgtcggatg ggcggtgatc actgatgaat    3480
ataaggttcc gtctaaaaag ttcaaggttc tgggaaatac agaccgccac agtatcaaaa    3540
aaaatcttat aggggctctt ttatttgaca gtggagagac agcggaagcg actcgtctca    3600
aacggacagc tcgtagaagg tatacacgtc ggaagaatcg tatttgttat ctacaggaga    3660
ttttttcaaa tgagatggcg aaagtagatg atagtttctt tcatcgactt gaagagtctt    3720
ttttggtgga agaagacaag aagcatgaac gtcatcctat ttttggaaat atagtagatg    3780
aagttgctta tcatgagaaa tatccaacta tctatcatct gcgaaaaaaa ttggtagatt    3840
ctactgataa agcggatttg cgcttaatct atttggcctt agcgcatatg attaagtttc    3900
gtggtcattt tttgattgag ggagatttaa atcctgataa tagtgatgtg acaaactat    3960 ttatccagtt ggtacaaacc tacaatcaat tatttgaaga aaacccctatt aacgcaagtg    4020 gagtagatgc taaagcgatt cttctgcac gattgagtaa atcaagacga ttagaaaatc    4080
tcattgctca gctccccggt gagaagaaaa atggcttatt tgggaatctc attgctttgt    4140
cattgggttt gacccctaat tttaaatcaa attttgattt ggcagaagat gctaaattac    4200
agctttcaaa agatacttac gatgatgatt tagataattt attggcgcaa attggagatc    4260
aatatgctga tttgtttttg gcagctaaga atttatcaga tgctatttta cttttcagata    4320 tcctaagagt aaatactgaa ataactaagg ctcccctatc agcttcaatg attaaacgct    4380
acgatgaaca tcatcaagac ttgactcttt taaaagcttt agttcgacaa caacttccag    4440
aaaagtataa agaaatcttt tttgatcaat caaaaacgg atatgcaggt tatattgatg    4500
ggggagctag ccaagaagaa ttttataaat ttatcaaacc aattttagaa aaaatggatg    4560
gtactgagga attattggtg aaactaaatc gtgaagattt gctgcgcaag caacggacct    4620
ttgacaacgg ctctattccc catcaaattc acttgggtga gctgcatgct attttgagaa    4680
gacaagaaga cttttatcca tttttaaaag acaatcgtga aagattgaa aaaatcttga    4740 cttttcgaat tccttattat gttggtccat ggcgcgtgg caatagtcgt tttgcatgga    4800
tgactcggaa gtctgaagaa acaattaccc catggaattt gaagaagtt gtcgataag    4860 gtgcttcagc tcaatcattt attgaacgca tgacaaactt tgataaaaat cttccaaatg    4920
aaaaagtact accaaaacat agtttgcttt atgagtattt tacggtttat aacgaattga    4980
caaaggtcaa atatgttact gaaggaatgc gaaaaccagc atttctttca ggtgaacaga    5040
agaaagccat tgttgattta ctcttcaaaa caaatcgaaa agtaaccgtt aagcaattaa    5100
aagaagatta tttcaaaaaa atagaatgtt ttgatagtgt tgaaatttca ggagttgaag    5160
```

| | |
|---|---|
| atagatttaa tgcttcatta ggtacctacc atgatttgct aaaaattatt aaagataaag | 5220 |
| atttttggga taatgaagaa aatgaagata tcttagagga tattgtttta acattgacct | 5280 |
| tatttgaaga tagggagatg attgaggaaa gacttaaaac atatgctcac ctctttgatg | 5340 |
| ataaggtgat gaaacagctt aaacgtcgcc gttatactgg ttggggacgt ttgtctcgaa | 5400 |
| aattgattaa tggtattagg gataagcaat ctggcaaaac aatattagat tttttgaaat | 5460 |
| cagatggttt tgccaatcgc aattttatgc agctgatcca tgatgatagt ttgacattta | 5520 |
| aagaagacat tcaaaaagca caagtgtctg acaaggcga tagtttacat gaacatattg | 5580 |
| caaatttagc tggtagccct gctattaaaa aaggtatttt acagactgta aaagttgttg | 5640 |
| atgaattggt caaagtaatg gggcggcata agccagaaaa tatcgttatt gaaatggcac | 5700 |
| gtgaaaatca gacaactcaa aagggccaga aaaattcgcg agagcgtatg aaacgaatcg | 5760 |
| aagaaggtat caaagaatta ggaagtcaga ttcttaaaga gcatcctgtt gaaaatactc | 5820 |
| aattgcaaaa tgaaaagctc tatctctatt atctccaaaa tggaagagac atgtatgtgg | 5880 |
| accaagaatt agatattaat cgtttaagtg attatgatgt cgatgccatt gttccacaaa | 5940 |
| gtttccttaa agacgattca atagacaata aggtcttaac gcgttctgat aaaaatcgtg | 6000 |
| gtaaatcgga taacgttcca agtgaagaag tagtcaaaaa gatgaaaaac tattggagac | 6060 |
| aacttctaaa cgccaagtta atcactcaac gtaagtttga taatttaacg aaagctgaac | 6120 |
| gtggaggttt gagtgaactt gataaagctg gttttatcaa acgccaattg gttgaaactc | 6180 |
| gccaaatcac taagcatgtg gcacaaattt tggatagtcg catgaatact aaatacgatg | 6240 |
| aaaatgataa acttattcga gaggttaaag tgattacctt aaaatctaaa ttagtttctg | 6300 |
| acttccgaaa agatttccaa ttctataaag tacgtgagat taacaattac catcatgccc | 6360 |
| atgatgcgta tctaaatgcc gtcgttggaa ctgctttgat taagaaatat ccaaaacttg | 6420 |
| aatcggagtt tgtctatggt gattataaag tttatgatgt tcgtaaaatg attgctaagt | 6480 |
| ctgagcaaga aataggcaaa gcaaccgcaa aatatttctt ttactctaat atcatgaact | 6540 |
| tcttcaaaac agaaattaca cttgcaaatg gagagattcg caaacgccct ctaatcgaaa | 6600 |
| ctaatgggga aactggagaa attgtctggg ataaagggcg agattttgcc acagtgcgca | 6660 |
| aagtattgtc catgccccaa gtcaatattg tcaagaaaac agaagtacag acaggcggat | 6720 |
| tctccaagga gtcaattttta ccaaaaagaa attcggacaa gcttattgct cgtaaaaaag | 6780 |
| actgggatcc aaaaaaatat ggtggttttg atagtccaac ggtagcttat tcagtcctag | 6840 |
| tggttgctaa ggtggaaaaa gggaaatcga agaagttaaa atccgttaaa gagttactag | 6900 |
| ggatcacaat tatggaagga agttcctttg aaaaaaatcc gattgacttt ttagaagcta | 6960 |
| aaggatataa ggaagttaaa aaagacttaa tcattaaact acctaaatat agtcttttttg | 7020 |
| agttagaaaa cggtcgtaaa cggatgctgg ctagtgccgg agaattacaa aaaggaaatg | 7080 |
| agctggctct gccaagcaaa tatgtgaatt tttatatttt agctagtcat tatgaaaagt | 7140 |
| tgaagggtag tccagaagat aacgaacaaa aacaattgtt tgtggagcag cataagcatt | 7200 |
| atttagatga gattattgag caaatcagtg aattttctaa gcgtgttatt ttagcagatg | 7260 |
| ccaatttaga taaagttctt agtgcatata acaaacatag agacaaacca atacgtgaac | 7320 |
| aagcagaaaa tattattcat ttatttacgt tgacgaatct tggagctccc gctgctttta | 7380 |
| aatattttga tacaacaatt gatcgtaaac gatatacgtc tacaaaagaa gttttagatg | 7440 |
| ccactcttat ccatcaatcc atcactggtc tttatgaaac acgcattgat ttgagtcagc | 7500 |

```
taggaggtga cggtggagga ggttctggag gtggaggttc tgctgagtat gtgcgagccc    7560
tctttgactt taatgggaat gatgaagagg atcttccctt taagaaagga gacatcctga    7620
gaatccggga taagcctgag gagcagtggt ggaatgcaga ggacagcgaa ggaaagaggg    7680
ggatgattcc tgtcccttac gtggagaagt attccggaga ctataaggac cacgacggag    7740
actacaagga tcatgatatt gattacaaag acgatgacga taagtctagg ctcgagtccg    7800
gagactataa ggaccacgac ggagactaca aggatcatga tattgattac aaagacgatg    7860
acgataagtc taggatgacc gacgctgagt acgtgagaat ccatgagaag ttggacatct    7920
acacgtttaa gaaacagttt ttcaacaaca aaaaatccgt gtcgcataga tgctacgttc    7980
tctttgaatt aaaacgacgg ggtgaacgta gagcgtgttt ttggggctat gctgtgaata    8040
aaccacagag cgggacagaa cgtggcattc acgccgaaat ctttagcatt agaaaagtcg    8100
aagaatacct gcgcgacaac cccggacaat tcacgataaa ttggtactca tcctggagtc    8160
cttgtgcaga ttgcgctgaa aagatcttag aatggtataa ccaggagctg cgggggaacg    8220
gccacacttt gaaaatctgg gcttgcaaac tctattacga gaaaaatgcg aggaatcaaa    8280
ttgggctgtg gaacctcaga gataacgggg ttgggttgaa tgtaatggta agtgaacact    8340
accaatgttg caggaaaata ttcatccaat cgtcgcacaa tcaattgaat gagaatagat    8400
ggcttgagaa gactttgaag cgagctgaaa acgacggag cgagttgtcc attatgattc    8460
aggtaaaaat actccacacc actaagagtc ctgctgttac ttgacaggca tcaaataaaa    8520
cgaaaggctc agtcgaaaga ctgggccttt cgttttatct gttgtttgcg gccgggtacc    8580
gagctcgaat tcactggccg tcgttttaca acgtcgtgac tgggaaaacc ctggcgttac    8640
ccaacttaat cgccttgcag cacatccccc tttcgccagc tggcgtaata gcgaagaggc    8700
ccgcaccgat cgcccttccc aacagttgcg cagcctgaat ggcgaatggc gattcacaaa    8760
aaataggtac acgaaaaaca agttaaggga tgcagtttat gcatccctta acttacttat    8820
taaataattt atagctattg aaaagagata agaattgttc aaagctaata ttgtttaaat    8880
cgtcaattcc tgcatgtttt aaggaattgt taaattgatt ttttgtaaat atttttcttgt    8940 attctttgtt aacccatttc ataacgaaat aattatactt ctgttatct ttgtgtgata    9000 ttcttgattt ttttctattt aatctgataa gtgagctatt cactttaggt ttaggatgaa    9060
aatattctct tggaaccata cttaatatag aaatatcaac ttctgccatt aaaaataatg    9120
ccaatgagcg ttttgtattt aataatcttt tagcaaaccc gtattccacg attaaataaa    9180
tctcatcagc tatactatca aaaacaattt tgcgtattat atccgtactt atgttataag    9240
gtatattacc aaatatttta taggattggt ttttaggaaa tttaaactgc aatatatcct    9300
tgtttaaaac ttgaaaatta tcgtgatcaa caagtttatt ttctgtagtt ttgcataatt    9360
tatggtctat ttcaatggca gttacgaaat tacacctctg tactaattca agggtaaaat    9420 gccctttttcc tgagccgatt tcaaagatat tatcatgttc atttaatctt atatttgtca    9480
ttattttatc tatattatgt tttgaagtaa taaagttttg actgtgtttt atatttttct    9540
cgttcattat aaccctcttt atttttttcct ccttataaaa ttagtataat tatagcacga    9600
gctctgataa atatgaacat gatgagtgat cgttaaattt atactgcaat ctgatgcgat    9660
tattgaataa aagatatgag agatttatct agtttctttt tttacaagaa aaaagaaagt    9720
tcttaaaggt tttatacttt tggtcgtaga gcacacggtt taacgactta attacgaagt    9780
aaataagtct agtgtgttag actttaatgt ttttttaagg cattagtgca tttaagcgtc    9840
agagcatggc tttatgccga gaaaactatt ggttggaatg gcgtgtgtgt tagccaaagc    9900
```

```
tttggcgagt tggttggggg tttcatggga ttaatcccat gaaagtacca actcaacaac    9960
acactaacgc ctgttggttc caaccaatag gaaattggaa taagcaatta gtataatgag   10020
agtataatgt tggtataacg ttagtataat gatgcttttt ttcattatat tttttatgta   10080
ctttaaacct gcacgcttat gtgaattaga aaaagcttaa tcgcatttca tagattgacc   10140
tcccaataac tacgtggtgt tattgggagg tcaatctatt tcatttgcct cttgctcaaa   10200
gttcccaaat tcgagtaaga ggtattttg tttttggtcg tcgcctctca ttagtagttc    10260
agggtttaac attaatactc cagttttcct ttttataata tttccttctt ctaagatttt   10320
aagtgttgtt attactgttt gtagacttgt tcctgtagct tttgctattt ctcttgttgt   10380
agctatcatt gtattgttac ttaagtggac attatctagg atatagttaa cgattttaag   10440
ttttttttccg ccaatcatat ctaacatact tattaattgc actatatatg cctttacgaa  10500
gttaccagac gtttgtttac ggtataactt gtctacctct atgacttctc cactttcttc   10560
gtctatgagc ctctgagagc ctttatagac tgttccatat cttctttca tcttttttctc   10620
actccttatt ttaaactatt ctaactatat cataactgtt ctaaaaaaaa aagaacattt   10680
gttaaaagaa attagaacaa aatgagtgaa aaattagaac aaacaaattc cttataaacc   10740
ttatcatctc aacctatatt aagattttac ctagttgaat cttcttttct atataaagcg   10800
tcggagcata tcagggggtt atctaacgta aatgctaccc ttcggctcgc tttcgctcgg   10860
cattgac                                                             10867

<210> SEQ ID NO 43
<211> LENGTH: 66
<212> TYPE: DNA
<213> ORGANISM: artificial sequence
<220> FEATURE:
<223> OTHER INFORMATION: CAN1 ORF

<400> SEQUENCE: 43
ggggttaccg gcccagttgg attccgttat tggagaaacc caggtgcctg gggtccaggt    60
ataata                                                               66

<210> SEQ ID NO 44
<211> LENGTH: 66
<212> TYPE: DNA
<213> ORGANISM: artificial sequence
<220> FEATURE:
<223> OTHER INFORMATION: CAN1 ORF

<400> SEQUENCE: 44
ccccaatggc cgggtcaacc taaggcaata acctctttgg gtccacggac cccaggtcca    60
tattat                                                               66

<210> SEQ ID NO 45
<211> LENGTH: 66
<212> TYPE: DNA
<213> ORGANISM: artificial sequence
<220> FEATURE:
<223> OTHER INFORMATION: mutant sequence

<400> SEQUENCE: 45
ggggttaccg gcccagttgg attcccttat tggagaaacc caggtgcctg gggtccaggt    60
ataata                                                               66

<210> SEQ ID NO 46
```

```
<211> LENGTH: 40
<212> TYPE: DNA
<213> ORGANISM: artificial sequence
<220> FEATURE:
<223> OTHER INFORMATION: target sequence

<400> SEQUENCE: 46
aaatggcgag gatacgttct ctatggagga tggcataggt                    40

<210> SEQ ID NO 47
<211> LENGTH: 40
<212> TYPE: DNA
<213> ORGANISM: artificial sequence
<220> FEATURE:
<223> OTHER INFORMATION: target sequence

<400> SEQUENCE: 47
tttaccgctc ctatgcaaga gatacctcct accgtatcca                    40

<210> SEQ ID NO 48
<211> LENGTH: 47
<212> TYPE: DNA
<213> ORGANISM: artificial sequence
<220> FEATURE:
<223> OTHER INFORMATION: CAN1 ORF

<400> SEQUENCE: 48
gattccgtta ttggagaaac ccaggtgcct ggggtccagg tataata          47

<210> SEQ ID NO 49
<211> LENGTH: 47
<212> TYPE: DNA
<213> ORGANISM: artificial sequence
<220> FEATURE:
<223> OTHER INFORMATION: CAN1 ORF

<400> SEQUENCE: 49
ctaaggcaat aacctctttg ggtccacgga ccccaggtcc atattat           47

<210> SEQ ID NO 50
<211> LENGTH: 40
<212> TYPE: DNA
<213> ORGANISM: artificial sequence
<220> FEATURE:
<223> OTHER INFORMATION: Ade1

<400> SEQUENCE: 50
taacgataat gtcaattacg aagactgaac tggacggtat                    40

<210> SEQ ID NO 51
<211> LENGTH: 11
<212> TYPE: PRT
<213> ORGANISM: artificial sequence
<220> FEATURE:
<223> OTHER INFORMATION: Ade1

<400> SEQUENCE: 51

Met Ser Ile Thr Lys Thr Glu Leu Asp Gly Ile
1               5                   10

<210> SEQ ID NO 52
<211> LENGTH: 40
<212> TYPE: DNA
<213> ORGANISM: artificial sequence
<220> FEATURE:
<223> OTHER INFORMATION: Ade1
```

```
<400> SEQUENCE: 52
taacgataat gtgaattacg aagactgaac tggacggtat                            40

<210> SEQ ID NO 53
<211> LENGTH: 40
<212> TYPE: DNA
<213> ORGANISM: artificial sequence
<220> FEATURE:
<223> OTHER INFORMATION: Ade1

<400> SEQUENCE: 53
taacgataat gttaattacg aagactgaac tggacggtat                            40

<210> SEQ ID NO 54
<211> LENGTH: 40
<212> TYPE: DNA
<213> ORGANISM: artificial sequence
<220> FEATURE:
<223> OTHER INFORMATION: Can1

<400> SEQUENCE: 54
ggggttaccg gcccagttgg attccgttat tggagaaacc                            40

<210> SEQ ID NO 55
<211> LENGTH: 13
<212> TYPE: PRT
<213> ORGANISM: artificial sequence
<220> FEATURE:
<223> OTHER INFORMATION: Can1

<400> SEQUENCE: 55

Gly Val Thr Gly Pro Val Gly Phe Arg Tyr Trp Arg Asn
1               5                   10

<210> SEQ ID NO 56
<211> LENGTH: 40
<212> TYPE: DNA
<213> ORGANISM: artificial sequence
<220> FEATURE:
<223> OTHER INFORMATION: Can1

<400> SEQUENCE: 56
ggggttaccg gcccagttgg attcccttat tggagaaacc                            40

<210> SEQ ID NO 57
<211> LENGTH: 40
<212> TYPE: DNA
<213> ORGANISM: artificial sequence
<220> FEATURE:
<223> OTHER INFORMATION: Can1

<400> SEQUENCE: 57
ggggttaccg gcccagttgg attccattat tggagaaacc                            40

<210> SEQ ID NO 58
<211> LENGTH: 40
<212> TYPE: DNA
<213> ORGANISM: artificial sequence
<220> FEATURE:
<223> OTHER INFORMATION: Can1

<400> SEQUENCE: 58
ggggttaccg gcccagttga attcccttat tggagaaacc                            40

<210> SEQ ID NO 59
```

```
<211> LENGTH: 40
<212> TYPE: DNA
<213> ORGANISM: artificial sequence
<220> FEATURE:
<223> OTHER INFORMATION: Can1

<400> SEQUENCE: 59
ggggttaccg gcccagttgg attcctttat tggagaaacc                         40

<210> SEQ ID NO 60
<211> LENGTH: 21
<212> TYPE: DNA
<213> ORGANISM: artificial sequence
<220> FEATURE:
<223> OTHER INFORMATION: WT-Ade1

<400> SEQUENCE: 60
acgataatgt caattacgaa g                                             21

<210> SEQ ID NO 61
<211> LENGTH: 20
<212> TYPE: DNA
<213> ORGANISM: artificial sequence
<220> FEATURE:
<223> OTHER INFORMATION: galK

<400> SEQUENCE: 61
tcaatgggct aactacgttc                                               20

<210> SEQ ID NO 62
<211> LENGTH: 20
<212> TYPE: DNA
<213> ORGANISM: artificial sequence
<220> FEATURE:
<223> OTHER INFORMATION: galK

<400> SEQUENCE: 62
ttaatgggct aactacgttc                                               20

<210> SEQ ID NO 63
<211> LENGTH: 20
<212> TYPE: DNA
<213> ORGANISM: artificial sequence
<220> FEATURE:
<223> OTHER INFORMATION: rpoB

<400> SEQUENCE: 63
gctgtctcag tttatggacc                                               20

<210> SEQ ID NO 64
<211> LENGTH: 20
<212> TYPE: DNA
<213> ORGANISM: artificial sequence
<220> FEATURE:
<223> OTHER INFORMATION: rpoB

<400> SEQUENCE: 64
cgacagagtc aaatacctgg                                               20

<210> SEQ ID NO 65
<211> LENGTH: 20
<212> TYPE: DNA
<213> ORGANISM: artificial sequence
<220> FEATURE:
<223> OTHER INFORMATION: rpoB

<400> SEQUENCE: 65
```

```
gctgtctcag tttatggacc                                               20

<210> SEQ ID NO 66
<211> LENGTH: 20
<212> TYPE: DNA
<213> ORGANISM: artificial sequence
<220> FEATURE:
<223> OTHER INFORMATION: rpoB

<400> SEQUENCE: 66
gctgtctcag tttatgaacc                                               20

<210> SEQ ID NO 67
<211> LENGTH: 20
<212> TYPE: DNA
<213> ORGANISM: artificial sequence
<220> FEATURE:
<223> OTHER INFORMATION: rpoB

<400> SEQUENCE: 67
gctgtctcag tttataaacc                                               20

<210> SEQ ID NO 68
<211> LENGTH: 20
<212> TYPE: DNA
<213> ORGANISM: artificial sequence
<220> FEATURE:
<223> OTHER INFORMATION: rpoB

<400> SEQUENCE: 68
cgacagagtc aaatacttgg                                               20

<210> SEQ ID NO 69
<211> LENGTH: 60
<212> TYPE: DNA
<213> ORGANISM: artificial sequence
<220> FEATURE:
<223> OTHER INFORMATION: target

<400> SEQUENCE: 69
tcgcttgaac atccagcgaa acaggccccc cccatcgagc agaaaacggt ggtggatggc   60

<210> SEQ ID NO 70
<211> LENGTH: 60
<212> TYPE: DNA
<213> ORGANISM: artificial sequence
<220> FEATURE:
<223> OTHER INFORMATION: target

<400> SEQUENCE: 70
tcgcttgaac atccagcgaa acaggttccc cccatcgagc agaaaacggt ggtggatggc   60

<210> SEQ ID NO 71
<211> LENGTH: 60
<212> TYPE: DNA
<213> ORGANISM: artificial sequence
<220> FEATURE:
<223> OTHER INFORMATION: target

<400> SEQUENCE: 71
tcgcttgaac atccagcgaa acaggtcccc cccatcgagc agaaaacggt ggtggatggc   60

<210> SEQ ID NO 72
<211> LENGTH: 60
<212> TYPE: DNA
```

```
<213> ORGANISM: artificial sequence
<220> FEATURE:
<223> OTHER INFORMATION: target

<400> SEQUENCE: 72
tcgcttgaac atccagcgaa acaggccccc cccatcgagc agaaaacggt ggtggatggc    60

<210> SEQ ID NO 73
<211> LENGTH: 60
<212> TYPE: DNA
<213> ORGANISM: artificial sequence
<220> FEATURE:
<223> OTHER INFORMATION: target

<400> SEQUENCE: 73
tcgcttgaac atccagcgaa acaggccccc cccatcgagc agaaaacggt ggtggatggc    60

<210> SEQ ID NO 74
<211> LENGTH: 60
<212> TYPE: DNA
<213> ORGANISM: artificial sequence
<220> FEATURE:
<223> OTHER INFORMATION: target

<400> SEQUENCE: 74
tcgcttgaac atccagcgaa acaggccccc cccatcgagc agaaaacggt ggtggatggc    60

<210> SEQ ID NO 75
<211> LENGTH: 60
<212> TYPE: DNA
<213> ORGANISM: artificial sequence
<220> FEATURE:
<223> OTHER INFORMATION: target

<400> SEQUENCE: 75
tcgcttgaac atccagcgaa acaggtcccc cccatcgagc agaaaacggt ggtggatggc    60

<210> SEQ ID NO 76
<211> LENGTH: 60
<212> TYPE: DNA
<213> ORGANISM: artificial sequence
<220> FEATURE:
<223> OTHER INFORMATION: target

<400> SEQUENCE: 76
tcgcttgaac atccagcgaa acaggccccc cccatcgagc agaaaacggt ggtggatggc    60

<210> SEQ ID NO 77
<211> LENGTH: 60
<212> TYPE: DNA
<213> ORGANISM: artificial sequence
<220> FEATURE:
<223> OTHER INFORMATION: target

<400> SEQUENCE: 77
tcgcttgaac atccagcgaa acaggccccc cccatcgagc agaaaacggt ggtggatggc    60

<210> SEQ ID NO 78
<211> LENGTH: 60
<212> TYPE: DNA
<213> ORGANISM: artificial sequence
<220> FEATURE:
<223> OTHER INFORMATION: target

<400> SEQUENCE: 78
tcgcttgaac atccagcgaa acaggcctcc cccatcgagc agaaaacggt ggtggatggc    60
```

<210> SEQ ID NO 79
<211> LENGTH: 60
<212> TYPE: DNA
<213> ORGANISM: artificial sequence
<220> FEATURE:
<223> OTHER INFORMATION: target

<400> SEQUENCE: 79
tcgcttgaac atccagcgaa acaggccttc cccatcgagc agaaaacggt ggtggatggc    60

<210> SEQ ID NO 80
<211> LENGTH: 60
<212> TYPE: DNA
<213> ORGANISM: artificial sequence
<220> FEATURE:
<223> OTHER INFORMATION: target

<400> SEQUENCE: 80
tcgcttgaac atccagcgaa acaggccttc cccatcgagc agaaaacggt ggtggatggc    60

<210> SEQ ID NO 81
<211> LENGTH: 60
<212> TYPE: DNA
<213> ORGANISM: artificial sequence
<220> FEATURE:
<223> OTHER INFORMATION: target

<400> SEQUENCE: 81
tcgcttgaac atccagcgaa acaggccttc cccatcgagc agaaaacggt ggtggatggc    60

<210> SEQ ID NO 82
<211> LENGTH: 60
<212> TYPE: DNA
<213> ORGANISM: artificial sequence
<220> FEATURE:
<223> OTHER INFORMATION: target

<400> SEQUENCE: 82
tcgcttgaac atccagcgaa acaggccttc cccatcgagc agaaaacggt ggtggatggc    60

<210> SEQ ID NO 83
<211> LENGTH: 60
<212> TYPE: DNA
<213> ORGANISM: artificial sequence
<220> FEATURE:
<223> OTHER INFORMATION: target

<400> SEQUENCE: 83
tcgcttgaac atccagcgaa acaggccccc cccatcgagc agaaaacggt ggtggatggc    60

<210> SEQ ID NO 84
<211> LENGTH: 60
<212> TYPE: DNA
<213> ORGANISM: artificial sequence
<220> FEATURE:
<223> OTHER INFORMATION: target

<400> SEQUENCE: 84
tcgcttgaac atccagcgaa acaggccttt cccatcgagc agaaaacggt ggtggatggc    60

<210> SEQ ID NO 85
<211> LENGTH: 60
<212> TYPE: DNA
<213> ORGANISM: artificial sequence
<220> FEATURE:

<223> OTHER INFORMATION: target

<400> SEQUENCE: 85
tcgcttgaac atccagcgaa acaggcccct tccatcgagc agaaaacggt ggtggatggc    60

<210> SEQ ID NO 86
<211> LENGTH: 60
<212> TYPE: DNA
<213> ORGANISM: artificial sequence
<220> FEATURE:
<223> OTHER INFORMATION: target

<400> SEQUENCE: 86
tcgcttgaac atccagcgaa acaggcccct cccatcgagc agaaaacggt ggtggatggc    60

<210> SEQ ID NO 87
<211> LENGTH: 60
<212> TYPE: DNA
<213> ORGANISM: artificial sequence
<220> FEATURE:
<223> OTHER INFORMATION: target

<400> SEQUENCE: 87
tcgcttgaac atccagcgaa acaggcccca cccatcgagc agaaaacggt ggtggatggc    60

<210> SEQ ID NO 88
<211> LENGTH: 60
<212> TYPE: DNA
<213> ORGANISM: artificial sequence
<220> FEATURE:
<223> OTHER INFORMATION: target

<400> SEQUENCE: 88
tcgcttgaac atccagcgaa acaggcccct tccatcgagc agaaaacggt ggtggatggc    60

<210> SEQ ID NO 89
<211> LENGTH: 60
<212> TYPE: DNA
<213> ORGANISM: artificial sequence
<220> FEATURE:
<223> OTHER INFORMATION: target

<400> SEQUENCE: 89
tcgcttgaac atccagcgaa acaggccccc cccatcgagc agaaaacggt ggtggatggc    60

<210> SEQ ID NO 90
<211> LENGTH: 20
<212> TYPE: DNA
<213> ORGANISM: artificial sequence
<220> FEATURE:
<223> OTHER INFORMATION: rpoB1r

<400> SEQUENCE: 90
gctgtctcag tttatggacc                                                20

<210> SEQ ID NO 91
<211> LENGTH: 20
<212> TYPE: DNA
<213> ORGANISM: artificial sequence
<220> FEATURE:
<223> OTHER INFORMATION: rpoB1r

<400> SEQUENCE: 91
gctgtctcag tttatgaacc                                                20

```
<210> SEQ ID NO 92
<211> LENGTH: 20
<212> TYPE: DNA
<213> ORGANISM: artificial sequence
<220> FEATURE:
<223> OTHER INFORMATION: galK 8

<400> SEQUENCE: 92
actcacacca ttcaggcgcc                                               20

<210> SEQ ID NO 93
<211> LENGTH: 20
<212> TYPE: DNA
<213> ORGANISM: artificial sequence
<220> FEATURE:
<223> OTHER INFORMATION: galK 8

<400> SEQUENCE: 93
acttacacca ttcaggcgcc                                               20

<210> SEQ ID NO 94
<211> LENGTH: 21
<212> TYPE: DNA
<213> ORGANISM: artificial sequence
<220> FEATURE:
<223> OTHER INFORMATION: galK 12

<400> SEQUENCE: 94
tcaatgggct aactacgttc g                                             21

<210> SEQ ID NO 95
<211> LENGTH: 21
<212> TYPE: DNA
<213> ORGANISM: artificial sequence
<220> FEATURE:
<223> OTHER INFORMATION: galK 12

<400> SEQUENCE: 95
ttaatgggct aactacgttc g                                             21
```

GENOMIC SEQUENCE MODIFICATION METHOD FOR SPECIFICALLY CONVERTING NUCLEIC ACID BASES OF TARGETED DNA SEQUENCE, AND MOLECULAR COMPLEX FOR USE IN SAME

CROSS-REFERENCE TO RELATED APPLICATIONS

This patent application is a divisional of U.S. patent application Ser. No. 15/124,021, filed Nov. 9, 2016; which is the U.S. national phase of International Patent Application No. PCT/JP2015/056436, filed Mar. 4, 2015; which claims the benefit of Japanese Patent Application No. 2014-043348, filed on Mar. 5, 2014, and Japanese Patent Application No. 2014-201859, filed on Sep. 30, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 96.9 KB ASCII (Text) file named "150161_401D1_SEQ_LISTING.txt" created Feb. 12, 2020.

TECHNICAL FIELD

The present invention relates to a modification method of a genome sequence, which enables modification of a nucleic acid base in a particular region of a genome, without cleaving double-stranded DNA (with no cleavage or single strand cleavage), and without inserting a foreign DNA fragment, and a complex of a nucleic acid sequence-recognizing module and a nucleic acid base converting enzyme used therefor.

BACKGROUND ART

In recent years, genome editing is attracting attention as a technique for modifying the target gene and genome region of interest in various species. Conventionally, as a method of genome editing, a method utilizing an artificial nuclease comprising a combination of a molecule having a sequence-independent DNA cleavage ability and a molecule having a sequence recognition ability has been proposed (non-patent document 1).

For example, a method of performing recombination at a target gene locus in DNA in a plant cell or insect cell as a host, by using a zinc finger nuclease (ZFN) wherein a zinc finger DNA binding domain and a non-specific DNA cleavage domain are linked (patent document 1); a method of cleaving or modifying a target gene in a particular nucleotide sequence or a site adjacent thereto by using TALEN wherein a transcription activator-like (TAL) effector, which is a DNA binding module that the plant pathogenic bacteria *Xanthomonas* has, and a DNA endonuclease are linked (patent document 2); a method utilizing CRISPR-Cas9 system wherein DNA sequence CRISPR (Clustered Regularly interspaced short palindromic repeats), that functions in an acquired immune system possessed by eubacterium and archaebacterium, and nuclease Cas (CRISPR-associated) protein family having an important function along with CRISPR are combined (patent document 3) and the like have been reported. Furthermore, a method of cleaving a target gene in the vicinity of a particular sequence, by using artificial nuclease wherein a PPR protein configured to recognize a particular nucleotide sequence by a series of PPR motifs each consisting of 35 amino acids and recognizing one nucleic acid base, and nuclease are linked (patent document 4) has also been reported.

DOCUMENT LIST

Patent Documents patent document 1: JP-B-4968498
patent document 2: National Publication of International Patent Application No. 2013-513389
patent document 3: National Publication of International Patent Application No. 2010-519929
patent document 4: JP-A-2013-128413

Non-Patent Document non-patent document 1: Kelvin M Esvelt, Harris H Wang (2013) Genome-scale engineering for systems and synthetic biology, Molecular Systems Biology 9: 641

SUMMARY OF THE INVENTION

Problems to be Solved by the Invention

The genome editing techniques heretofore been proposed basically presuppose double-stranded DNA breaks (DSB). However, since they involve unexpected genome modifications, side effects such as strong cytotoxicity, chromosomal rearrangement and the like occur, and they have common problems of impaired reliability in gene therapy, extremely small number of surviving cells by nucleotide modification, and difficulty in genetic modification itself in primate ovum and unicellular microorganisms.

Therefore, an object of the present invention is to provide a novel method of genome editing for modifying a nucleic acid base of a particular sequence of a gene without DSB or insertion of foreign DNA fragment, i.e., by non-cleavage of a double stranded DNA or single strand cleavage, and a complex of a nucleic acid sequence-recognizing module and a nucleic acid base converting enzyme therefor.

Means of Solving the Problems

The present inventors have conducted intensive studies in an attempt to solve the above-mentioned problems and taken note of adopting base conversion by a conversion reaction of DNA base, without accompanying DSB. The base conversion reaction by a deamination reaction of DNA base is already known; however, targeting any site by recognizing a particular sequence of DNA, and specifically modifying the targeted DNA by base conversion of DNA bases has not been realized yet.

Therefore, deaminase, that catalyzes a deamination reaction, was used as an enzyme for such conversion of nucleic acid bases, and linked to a molecule having a DNA sequence recognition ability, thereby a genome sequence was modified by nucleic acid base conversion in a region containing a particular DNA sequence.

Specifically, CRISPR-Cas system (CRISPR-mutant Cas) was used. That is, a DNA encoding an RNA molecule, wherein genome specific CRISPR-RNA:crRNA (gRNA) containing a sequence complementary to a target sequence of a gene to be modified is linked to an RNA for recruiting Cas protein (trans-activating crRNA: tracrRNA) was produced. On the other hand, a DNA wherein a DNA encoding a mutant Cas protein (dCas), wherein cleavage ability of one or both strands of a double stranded DNA is inactivated and a deaminase gene are linked, was produced. These DNAs were introduced into a host yeast cell which comprises a gene to be modified. As a result, mutation could be introduced randomly within the range of several hundred nucleotides of the gene of interest including the target sequence. Compared to when a double mutant Cas protein, which do not cleave both of DNA strands in the double stranded DNA, was used, the mutation introduction efficiency increased when a mutant Cas protein which cleave of either one of the strands was used. In addition, it was clarified that the area of mutation region and variety of mutation vary depending on which of the DNA double strand is cleaved. Furthermore, mutation could be introduced extremely efficiently by targeting a plurality of regions in the target gene of interest. That is, a host cell introduced with DNA was seeded in a nonselective medium, and the sequence of the target gene of interest was examined in randomly selected colonies. As a result, introduction of mutation was confirmed in almost all colonies. It was also confirmed that genome editing can be simultaneously performed at a plurality of sites by targeting certain region in two or more target genes of interest. It was further demonstrated that the method can simultaneously introduce mutation into alleles of diploid or polyploid genomes, can introduce mutation into not only eukaryotic cells but also prokaryotic cells such as *Escherichia coli*, and is widely applicable irrespective of species. It was also found that editing of essential gene, which showed low efficiency heretofore, can be efficiently performed by transiently performing a nucleic acid base conversion reaction at a desired stage.

The present inventor have conducted further studies based on these findings and completed the present invention.

Accordingly, the present invention is as described below.

[1] A method of modifying a targeted site of a double stranded DNA, comprising a step of contacting a complex wherein a nucleic acid sequence-recognizing module that specifically binds to a target nucleotide sequence in a selected double stranded DNA and a nucleic acid base converting enzyme are linked, with said double stranded DNA, to convert one or more nucleotides in the targeted site to other one or more nucleotides or delete one or more nucleotides, or insert one or more nucleotides into said targeted site, without cleaving at least one strand of said double stranded DNA in the targeted site.

[2] The method of [1], wherein the nucleic acid sequence-recognizing module is selected from the group consisting of a CRISPR-Cas system wherein at least one DNA cleavage ability of Cas is inactivated, a zinc finger motif, a TAL effector and a PPR motif.

[3] The method of [1], wherein the nucleic acid sequence-recognizing module is a CRISPR-Cas system wherein at least one DNA cleavage ability of Cas is inactivated.

[4] The method of any of [1]-[3], which uses two or more kinds of nucleic acid sequence-recognizing modules each specifically binding to a different target nucleotide sequence.

[5] The method of [4], wherein the different target nucleotide sequence is present in a different gene.

[6] The method of any of [1]-[5], wherein the nucleic acid base converting enzyme is deaminase.

[7] The method of the above-mentioned [6], wherein the deaminase is AID (AICDA).

[8] The method of any of [1]-[7], wherein the double stranded DNA is contacted with the complex by introducing a nucleic acid encoding the complex into a cell having the double stranded DNA.

[9] The method of [8], wherein the cell is a prokaryotic cell.

[10] The method of [8], wherein the aforementioned cell is a eukaryotic cell.

[11] The method of [8], wherein the cell is a cell of a microorganism.

[12] The method of [8], wherein the cell is a plant cell.

[13] The method of [8], wherein the cell is an insect cell.

[14] The method of [8], wherein the cell is an animal cell.

[15] The method of [8], wherein the aforementioned cell is a cell of a vertebrate.

[16] The method of [8], wherein the cell is a mammalian cell.

[17] The method of any of [9]-[16], wherein the cell is a polyploid cell, and a site in any targeted allele on a homologous chromosome is modified.

[18] The method of any of [8]-[17], comprising a step of introducing an expression vector comprising a nucleic acid encoding the complex in a form permitting control of an expression period into the cell, and a step of inducing expression of the nucleic acid for a period necessary for stabilizing the modification of the targeted site in the double stranded DNA.

[19] The method of the above-mentioned [18], wherein the target nucleotide sequence in the double stranded DNA is present in a gene essential for the cell.

[20] A nucleic acid-modifying enzyme complex wherein a nucleic acid sequence-recognizing module that specifically binds to a target nucleotide sequence in a selected double stranded DNA and a nucleic acid base converting enzyme are linked, which converts one or more nucleotides in the targeted site to other one or more nucleotides or deletes one or more nucleotides, or inserts one or more nucleotides into said targeted site, without cleaving at least one strand of said double stranded DNA in the targeted site.

[21] A nucleic acid encoding the nucleic acid-modifying enzyme complex of [20].

Effect of the Invention

According to the genome editing technique of the present invention, since it is not associated with insertion of a foreign DNA or double-stranded DNA breaks, the technique is superior in safety. The technique has some possibility of providing a solution in cases where conventional methods were considered as a gene recombination, and thus biologically or legally controversial. It is also theoretically possible to set a wide range of mutation introduction from a pin point of one base to several hundred bases, and the technique can also be applied to local evolution induction by introduction of random mutation into a particular limited region, which has been almost impossible heretofore.

BRIEF DESCRIPTION OF THE DRAWINGS

FIG. 10 shows that a mutation can be simultaneously introduced into both alleles on the homologous chromosome of diploid genome by the genetic modification method of the present invention. FIG. 10A shows homologous mutation introduction efficiency of Ade1 gene (upper panel) and can1 gene respectively. FIG. 10B shows that homologous mutation was actually introduced into red colony (lower panel). Also, occurrence of heterologous mutation in white colony was shown (upper panel).

FIG. 11 shows that genome editing of *Escherichia coli*, a prokaryotic cell, is possible by the genetic modification method of the present invention. FIG. 11A is a schematic illustration showing the plasmid used. FIG. 11B shows that a mutation (CAA→TAA) could be efficiently introduced by targeting a region in the galK gene. FIG. 11C shows the results of sequence analysis of each two clones of the respective colonies in a nonselective medium (none), a medium containing 25 μg/ml rifampicin (Rif25) or a medium containing 50 μg/ml rifampicin (Rif50). Introduction of a mutation imparting rifampicin resistance was confirmed (upper panel). The appearance frequency of rifampicin resistance strain was estimated to be about 10% (lower panel).

FIG. 12 shows control of the edited base sites by the length of guide RNA. FIG. 12A is a conceptual Figure of editing base site when the length of the target nucleotide sequence is 20 bases or 24 bases. FIG. 12B shows the results of editing by targeting gsiA gene and changing the length of the target nucleotide sequence. The mutated sites are shown with bold letters, "T" and "A" show introduction of complete mutation (C→T or G→A) into the clone, "t" shows that not less than 50% of mutation (C→T) is introduced into the clone (incomplete cloning), and "c" shows that the introduction efficiency of the mutation (C→T) into the clone is less than 50%.

FIG. 16 shows the results of introduction of mutation into the galK gene in Example 11.

DESCRIPTION OF EMBODIMENTS

Figure 1:
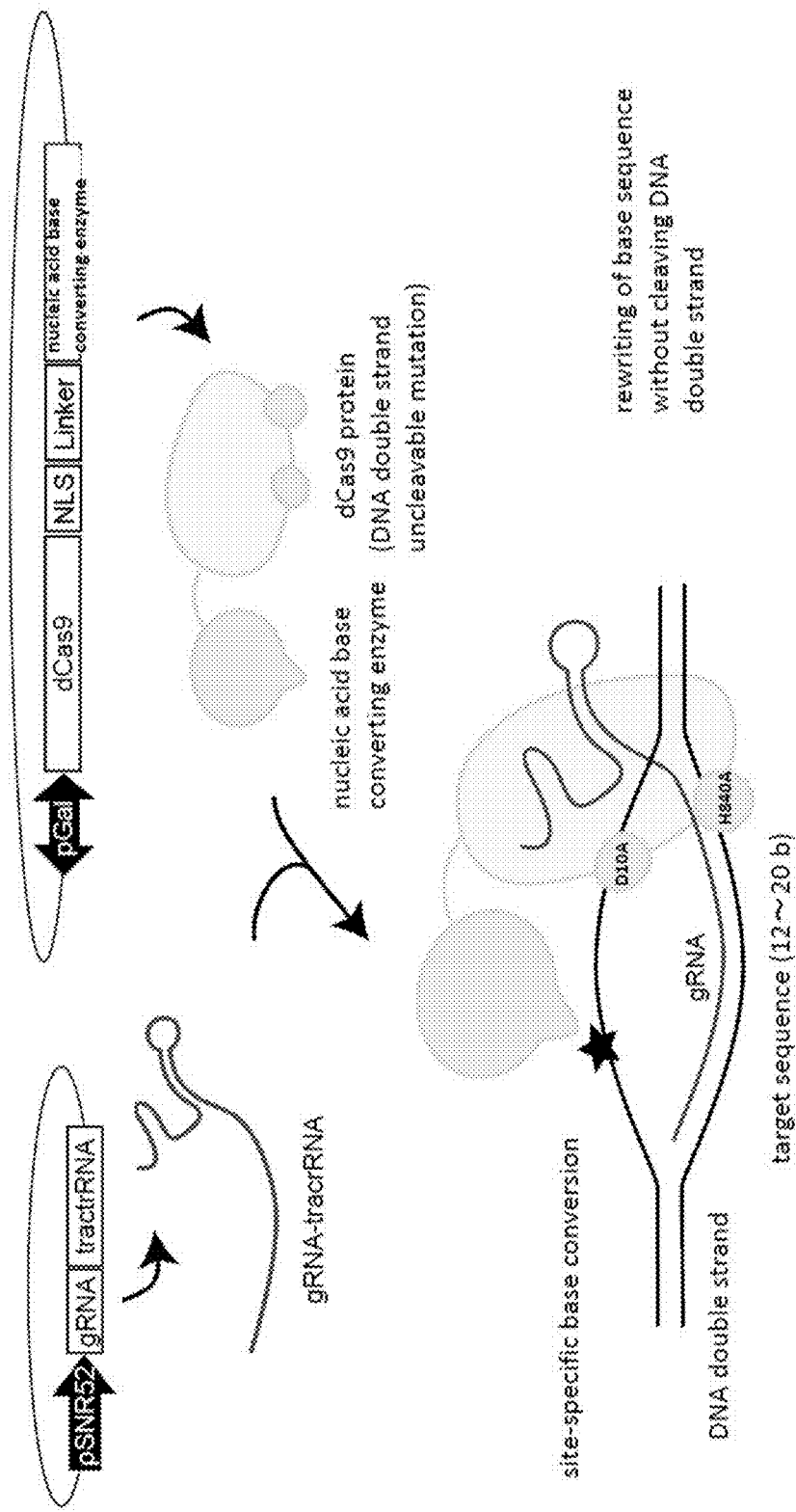
FIG. 1 is a schematic illustration showing a mechanism of the genetic modification method of the present invention using the CRISPR-Cas system.

The present invention provides a method of modifying a targeted site of a double stranded DNA by converting the target nucleotide sequence and nucleotides in the vicinity thereof in the double stranded DNA to other nucleotides, without cleaving at least one strand of the double stranded DNA to be modified. The method characteristically comprises a step of contacting a complex wherein a nucleic acid sequence-recognizing module that specifically binds to the target nucleotide sequence in the double stranded DNA and a nucleic acid base converting enzyme are linked, with the double stranded DNA to convert the targeted site, i.e., the target nucleotide sequence and nucleotides in the vicinity thereof, to other nucleotides.

In the present invention, the "modification" of a double stranded DNA means that a nucleotide (e.g., dC) on a DNA strand is converted to another nucleotide (e.g., dT, dA or dG), or deleted, or a nucleotide or a nucleotide sequence is inserted between certain nucleotides on the DNA strand. While the double stranded DNA to be modified is not particularly limited, it is preferably a genomic DNA. The "targeted site" of a double stranded DNA means the entire or partial "target nucleotide sequence", which a nucleic acid sequence-recognizing module specifically recognizes and binds to, or the vicinity of the target nucleotide sequence (one or both of 5' upstream and 3' downstream), and the length thereof can be appropriately adjusted between 1 base and several hundred bases according to the object.

In the present invention, the "nucleic acid sequence-recognizing module" means a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables a nucleic acid base converting enzyme linked to the module to specifically act on a targeted site of a double stranded DNA.

In the present invention, the "nucleic acid base converting enzyme" means an enzyme capable of converting a target nucleotide to another nucleotide by catalyzing a reaction for converting a substituent on a purine or pyrimidine ring on a DNA base to another group or atom, without cleaving the DNA strand.

In the present invention, the "nucleic acid-modifying enzyme complex" means a molecular complex comprising a complex of the above-mentioned nucleic acid sequence-recognizing module linked with a nucleic acid base converting enzyme, wherein the complex has nucleic acid base converting enzyme activity and is imparted with a particular nucleotide sequence recognition ability. The "complex" used herein encompasses not only one composed of a plurality of molecules, but also a single molecule having a nucleic acid sequence-recognizing module and a nucleic acid base converting enzyme such as a fusion protein.

The nucleic acid base converting enzyme used in the present invention is not particularly limited as long as it can catalyze the above-mentioned reaction, and examples thereof include deaminase belonging to the nucleic acid/nucleotide deaminase superfamily, which catalyzes a deamination reaction that converts an amino group to a carbonyl group. Preferable examples thereof include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is activation-induced cytidine deaminase (hereinafter also referred to as AID), which is an enzyme that introduces a mutation into an immunoglobulin gene in the acquired immunity of vertebrate or the like.

While the origin of nucleic acid base converting enzyme is not particularly limited, for example, PmCDA1 (Petromyzon marinus cytosine deaminase 1) from Petromyzon marinus, or AID (Activation-induced cytidine deaminase; AICDA) from mammal (e.g., human, swine, bovine, horse, monkey etc.) can be used. The base sequence and amino acid sequence of CDS of PmCDA1 are shown in SEQ ID NOs: 1 and 2, respectively, and the base sequence and amino acid sequence of CDS of human AID are shown in SEQ ID NOs: 3 and 4, respectively.

A target nucleotide sequence in a double stranded DNA to be recognized by the nucleic acid sequence-recognizing module in the nucleic acid-modifying enzyme complex of the present invention is not particularly limited as long as the module specifically binds to any sequence in the double stranded DNA. The length of the target nucleotide sequence only needs to be sufficient for specific binding of the nucleic acid sequence-recognizing module. For example, when mutation is introduced into a particular site in the genomic DNA of a mammal, it is not less than 12 nucleotides, preferably not less than 15 nucleotides, more preferably not less than 17 nucleotides, according to the genome size thereof. While the upper limit of the length is not particularly limited, it is preferably not more than 25 nucleotides, more preferably not more than 22 nucleotides.

As the nucleic acid sequence-recognizing module in the nucleic acid-modifying enzyme complex of the present invention, CRISPR-Cas system wherein at least one DNA cleavage ability of Cas is inactivated (CRISPR-mutant Cas), zinc finger motif, TAL effector and PPR motif and the like, as well as a fragment containing a DNA binding domain of a protein that specifically binds to DNA such as restriction enzyme, transcription factor, RNA polymerase or the like, and not having a DNA double strand cleavage ability and the like can be used, but the module is not limited thereto. Preferably, the modules include CRISPR-mutant Cas, zinc finger motif, TAL effector, PPR motif and the like.

A zinc finger motif is constructed by linking 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. The above-mentioned patent document 1 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply linking the modules. For TAL effector, production methods utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed relatively easily. The above-mentioned patent document 2 can be referred to as for the detail of the production of TAL effector.

PPR motif is constructed such that a particular nucleotide sequence is recognized by a series of PPR motifs each consisting of 35 amino acids and recognizing one nucleic acid base, and recognizes a target base only by 1, 4 and ii(-2) amino acids of each motif. Motif configuration has no dependency, and is free of interference of motifs on both sides. Therefore, similar to TAL effector, a PPR protein specific to the target nucleotide sequence can be produced by simply linking PPR motifs. The above-mentioned patent document 4 can be referred to as for the detail of the production of PPR motif.

When a fragment of a restriction enzyme, transcription factor, RNA polymerase or the like is used, since the DNA binding domains of these proteins are well known, a fragment containing said domain and not having a DNA double strand cleavage ability can be easily designed and constructed.

Any of the above-mentioned nucleic acid sequence-recognizing module can be provided as a fusion protein with the above-mentioned nucleic acid base converting enzyme, or a protein binding domain such as SH3 domain, PDZ domain, GK domain, GB domain and the like and a binding partner thereof may be fused with a nucleic acid sequence-recognizing module and a nucleic acid base converting enzyme, respectively, and provided as a protein complex via an interaction of the domain and a binding partner thereof. Alternatively, a nucleic acid sequence-recognizing module and a nucleic acid base converting enzyme may be each fused with intein, and they can be linked by ligation after protein synthesis.

The nucleic acid-modifying enzyme complex of the present invention containing a complex (including fusion protein), wherein a nucleic acid sequence-recognizing module and a nucleic acid base converting enzyme are linked, may be contacted with a double stranded DNA as an enzyme reaction in a cell-free system. In view of the main object of the present invention, it is desirable to perform the contact by introducing a nucleic acid encoding the complex into a cell having the double stranded DNA of interest (e.g., genomic DNA).

Therefore, the nucleic acid sequence-recognizing module and the nucleic acid base converting enzyme are preferably prepared as a nucleic acid encoding a fusion protein thereof, or as nucleic acids encoding each of them in a form capable of forming a complex in a host cell after translation into a protein by utilizing a binding domain, intein or the like. The nucleic acid here may be a DNA or an RNA. When it is a DNA, it is preferably a double stranded DNA, and provided in the form of an expression vector disposed under regulation of a functional promoter in a host cell. When it is an RNA, it is preferably a single stranded RNA.

Since the complex of the present invention wherein a nucleic acid sequence-recognizing module and a nucleic acid base converting enzyme are linked, is not associated with double-stranded DNA breaks (DSB), genome editing with low toxicity is possible, and the genetic modification method of the present invention can be applied to a wide range of biological materials. Therefore, the cells into which nucleic acid encoding nucleic acid sequence-recognizing module and/or nucleic acid base converting enzyme is introduced can encompass cells of any species, from cells of microorganisms, such as bacterium, such as *Escherichia coli* and the like which are prokaryotes, such as yeast and the like which are lower eukaryotes, to cells of higher eukaryotes such as insect, plant and the like, and cells of vertebrates including mammals such as human and the like.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer covering a region encoding a desired part of the protein (part containing DNA binding domain) based on the cDNA sequence information thereof, and amplifying by the RT-PCR method using, the total RNA or mRNA fraction prepared from the protein-producing cells as a template.

A DNA encoding a nucleic acid base converting enzyme can also be cloned similarly by synthesizing an oligoDNA primer based on the cDNA sequence information thereof, and amplifying by the RT-PCR method using, the total RNA or mRNA fraction prepared from the enzyme-producing cells as a template. For example, a DNA encoding PmCDA1 of Petromyzon marinus can be cloned by designing suitable primers for the upstream and downstream of CDS based on the cDNA sequence (accession No. EF094822) registered in the NCBI database, and cloning from mRNA Petromyzon marinus by the RT-PCR method. A DNA encoding human AID can be cloned by designing suitable primers for the upstream and downstream of CDS based on the cDNA sequence (accession No. AB040431) registered in the NCBI database, and cloning from, for example, mRNA from human lymph node by the RT-PCR method.

The cloned DNA may be directly, or after digestion with a restriction enzyme when desired, or after addition of a suitable linker and/or a nuclear localization signal (each organelle transfer signal when the target double stranded DNA of interest is mitochondria or chloroplast DNA), ligated with a DNA encoding a nucleic acid sequence-recognizing module to prepare a DNA encoding a fusion protein. Alternatively, a DNA encoding a nucleic acid sequence-recognizing module, and a DNA encoding a nucleic acid base converting enzyme may be each fused with a DNA encoding a binding domain or a binding partner thereof, or both DNAs may be fused with a DNA encoding a separation intein, whereby the nucleic acid sequence-recognizing conversion module and the nucleic acid base converting enzyme are translated in a host cell to form a complex. In these cases, a linker and/or a nuclear localization signal can be linked to a suitable position of one of or both DNAs when desired.

A DNA encoding a nucleic acid sequence-recognizing module and a DNA encoding a nucleic acid base converting enzyme can be obtained by chemically synthesizing the DNA strand, or by linking partly overlapping synthesized oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon used can be designed in CDS full-length according to the host into which the DNA is introduced. In the expression of a heterologous DNA, the protein expression level is expected to increase by converting the DNA sequence thereof to a codon which is highly frequently used in the host organism. As the data of codon use frequency in host used, for example, the genetic code use frequency database (www.kazusa.or.jp/codon/index.html) disclosed in the home page of Kazusa DNA Research Institute can be used, or documents showing the codon use frequency in each host may be referred to. By reference to the obtained data and the DNA sequence to be introduced, codons showing low use frequency in the host from those used for the DNA sequence may be converted to a codon coding the same amino acid and showing high use frequency.

An expression vector containing a DNA encoding a nucleic acid sequence-recognizing module and/or a nucleic acid base converting enzyme can be produced, for example, by linking the DNA to the downstream of a promoter in a suitable expression vector.

As the expression vector, plasmids from *Escherichia coli* (e.g., pBR322, pBR325, pUC12, pUC13); plasmids from *Bacillus subtilis* (e.g., pUB110, pTP5, pC194); plasmids from yeast (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λphage and the like; insect virus vectors such as baculovirus and the like (e.g., BmNPV, AcNPV); animal virus vectors such as retrovirus, vaccinia virus, adenovirus and the like, are used.

As the promoter, any promoter appropriate for a host used for gene expression can be used. In a conventional method involving DSB, since the survival rate of the host cell sometimes decreases markedly due to the toxicity, it is desirable to increase the number of cells by the start of the induction by using an inductive promoter. However, since sufficient cell proliferation can also be achieved by expressing the nucleic acid-modifying enzyme complex of the present invention, a constitutive promoter can also be used without limitation.

For example, when the host is an animal cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

When the host is *Escherichia coli*, trp promoter, lac promoter, recA promoter, λP$_L$ promoter, lpp promoter, T7 promoter and the like are preferable.

When the host is genus *Bacillus*, SPO1 promoter, SPO2 promoter, penP promoter and the like are preferable.

When the host is a yeast, Gal1/10 promoter, PHO5 promoter, PGK promoter, GAP promoter, ADH promoter and the like are preferable.

When the host is an insect cell, polyhedrin promoter, P10 promoter and the like are preferable.

When the host is a plant cell, CaMV35S promoter, CaMV19S promoter, NOS promoter and the like are preferable.

As the expression vector, besides those mentioned above, one containing enhancer, splicing signal, terminator, polyA addition signal, a selection marker such as drug resistance gene, auxotrophic complementary gene and the like, replication origin and the like on demand can be used.

An RNA encoding a nucleic acid sequence-recognizing module and/or a nucleic acid base converting enzyme can be prepared by, for example, transcription to mRNA in an in vitro transcription system known per se by using a vector encoding DNA encoding the above-mentioned nucleic acid sequence-recognizing module and/or a nucleic acid base converting enzyme as a template.

A complex of a nucleic acid sequence-recognizing module and a nucleic acid base converting enzyme can be intracellularly expressed by introducing an expression vector containing a DNA encoding a nucleic acid sequence-recognizing module and/or a nucleic acid base converting enzyme into a host cell, and culturing the host cell.

As the host, genus *Escherichia*, genus *Bacillus*, yeast, insect cell, insect, animal cell and the like are used.

As the genus *Escherichia*, *Escherichia coli* K12·DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used.

As the genus *Bacillus*, *Bacillus subtilis* MI114 [Gene, 24, 255 (1983)], *Bacillus subtilis* 207-21 [Journal of Biochemistry, 95, 87 (1984)] and the like are used.

As the yeast, *Saccharomyces cerevisiae* AH22, AH22R⁻, NA87-11A, DKD-5D, 20B-12, *Schizosaccharomyces pombe* NCYC1913, NCYC2036, *Pichia pastoris* KM71 and the like are used.

As the insect cell when the virus is AcNPV, cells of established line from cabbage armyworm larva (*Spodoptera frugiperda* cell; Sf cell), MG1 cells from the mid-intestine of *Trichoplusia ni*, High Five™ cells from an egg of *Trichoplusia ni*, cells from *Mamestra brassicae*, cells from *Estigmena acrea* and the like are used. When the virus is BmNPV, cells of established line from *Bombyx mori* (*Bombyx mori* N cell; BmN cell) and the like are used as insect cells. As the Sf cell, for example, Sf9 cell (ATCC CRL1711), Sf21 cell [all above, In Vivo, 13, 213-217 (1977)] and the like are used.

As the insect, for example, larva of *Bombyx mori*, *Drosophila*, cricket and the like are used [Nature, 315, 592 (1985)].

As the animal cell, cell lines such as monkey COS-7 cell, monkey Vero cell, Chinese hamster ovary (CHO) cell, dhfr gene-deficient CHO cell, mouse L cell, mouse AtT-20 cell, mouse myeloma cell, rat GH3 cell, human FL cell and the like, pluripotent stem cells such as iPS cell, ES cell and the like of human and other mammals, and primary cultured cells prepared from various tissues are used. Furthermore, zebrafish embryo, Xenopus oocyte and the like can also be used.

As the plant cell, suspend cultured cells, callus, protoplast, leaf segment, root segment and the like prepared from various plants (e.g., grain such as rice, wheat, corn and the like, product crops such as tomato, cucumber, egg plant and the like, garden plants such as carnation, Eustoma russellianum and the like, experiment plants such as tobacco, *Arabidopsis thaliana* and the like) are used.

All the above-mentioned host cells may be haploid (monoploid), or polyploid (e.g., diploid, triploid, tetraploid and the like). In the conventional mutation introduction methods, mutation is, in principle, introduced into only one homologous chromosome to produce a heterologous genotype. Therefore, the desired feature is not expressed unless it is a dominant mutation, and making it homologous inconveniently requires labor and time. In contrast, according to the present invention, since mutations can be introduced into all alleles on the homologous chromosome in the genome, desired feature can be expressed in a single generation even in the case of recessive mutation (FIG. 10), which is extremely useful since the problem of the conventional method can be solved.

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host.

*Escherichia coli* can be transformed according to the methods described in, for example, Proc. Natl. Acad. Sci. USA, 69, 2110 (1972), Gene, 17, 107 (1982) and the like.

A vector can be introduced into the genus *Bacillus* according to the methods described in, for example, Molecular & General Genetics, 168, 111 (1979) and the like.

A vector can be introduced into a yeast according to the methods described in, for example, Methods in Enzymology, 194, 182-187 (1991), Proc. Natl. Acad. Sci. USA, 75, 1929 (1978) and the like.

A vector can be introduced into an insect cell and an insect according to the methods described in, for example, Bio/Technology, 6, 47-55 (1988) and the like.

A vector can be introduced into an animal cell according to the methods described in, for example, Cell Engineering additional volume 8, New Cell Engineering Experiment Protocol, 263-267 (1995) (published by Shujunsha), and Virology, 52, 456 (1973).

A cell introduced with a vector can be cultured according to a known method according to the kind of the host.

For example, when *Escherichia coli* or genus *Bacillus* is cultured, a liquid medium is preferable as a medium used for the culture. The medium preferably contains a carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5-about 8.

As a medium for culturing *Escherichia coli*, for example, M9 medium containing glucose, casamino acid [Journal of Experiments in Molecular Genetics, 431-433, Cold Spring Harbor Laboratory, New York 1972] is preferable. Where necessary, for example, agents such as 3β-indolylacrylic acid may be added to the medium to ensure an efficient function of a promoter. *Escherichia coli* is cultured at generally about 15-about 43° C. Where necessary, aeration and stirring may be performed.

The genus *Bacillus* is cultured at generally about 30-about 40° C. Where necessary, aeration and stirring may be performed.

Examples of the medium for culturing yeast include Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] and the like. The pH of the medium is preferably about 5-about 8.

The culture is performed at generally about 20° C.-about 35° C. Where necessary, aeration and stirring may be performed.

As a medium for culturing an insect cell or insect, for example, Grace's Insect Medium [Nature, 195, 788 (1962)] containing an additive such as inactivated 10% bovine serum and the like as appropriate and the like are used. The pH of the medium is preferably about 6.2-about 6.4. The culture is performed at generally about 27° C. Where necessary, aeration and stirring may be performed.

As a medium for culturing an animal cell, for example, minimum essential medium (MEM) containing about 5-about 20% of fetal bovine serum [Science, 122, 501 (1952)], Dulbecco's modified Eagle medium (DMEM) [Virology, 8, 396 (1959)], RPMI 1640 medium [The Journal of the American Medical Association, 199, 519 (1967)], 199 medium [Proceeding of the Society for the Biological Medicine, 73, 1 (1950)] and the like are used. The pH of the medium is preferably about 6-about 8. The culture is performed at generally about 30° C.-about 40° C. Where necessary, aeration and stirring may be performed.

As a medium for culturing a plant cell, for example, MS medium, LS medium, B5 medium and the like are used. The pH of the medium is preferably about 5-about 8. The culture is performed at generally about 20° C.-about 30° C. Where necessary, aeration and stirring may be performed.

As mentioned above, a complex of a nucleic acid sequence-recognizing module and a nucleic acid base converting enzyme, i.e., nucleic acid-modifying enzyme complex, can be expressed intracellularly.

An RNA encoding a nucleic acid sequence-recognizing module and/or a nucleic acid base converting enzyme can be introduced into a host cell by microinjection method, lipofection method and the like. RNA introduction can be performed once or multiple times (e.g., 2-5 times) at suitable intervals.

When a complex of a nucleic acid sequence-recognizing module and a nucleic acid base converting enzyme is expressed by an expression vector or RNA molecule introduced into the cell, the nucleic acid sequence-recognizing module specifically recognizes and binds to a target nucleotide sequence in the double stranded DNA (e.g., genomic DNA) of interest and, due to the action of the nucleic acid base converting enzyme linked to the nucleic acid sequence-recognizing module, base conversion occurs in the sense strand or antisense strand of the targeted site (whole or partial target nucleotide sequence or appropriately adjusted within several hundred bases including the vicinity thereof) and a mismatch occurs in the double stranded DNA (e.g., when cytidine deaminase such as PmCDA1, AID and the like is used as a nucleic acid base converting enzyme, cytosine on the sense strand or antisense strand at the targeted site is converted to uracil to cause U:G or G:U mismatch). When the mismatch is not correctly repaired, and when repaired such that a base of the opposite strand forms a pair with a base of the converted strand (T-A or A-T in the above-mentioned example), or when another nucleotide is further substituted (e.g., U→A, G) or when one to several dozen bases are deleted or inserted during repair, various mutations are introduced.

As for zinc finger motif, production of many actually functional zinc finger motifs is not easy, since production efficiency of a zinc finger that specifically binds to a target nucleotide sequence is not high and selection of a zinc finger having high binding specificity is not easy. While TAL effector and PPR motif have a high degree of freedom of target nucleic acid sequence recognition as compared to zinc finger motif, a problem remains in the efficiency since a large protein needs to be designed and constructed every time according to the target nucleotide sequence.

In contrast, since the CRISPR-Cas system recognizes the sequence of double stranded DNA of interest by a guide RNA complementary to the target nucleotide sequence, any sequence can be targeted by simply synthesizing an oligoDNA capable of specifically forming a hybrid with the target nucleotide sequence.

Therefore, in a more preferable embodiment of the present invention, a CRISPR-Cas system wherein at least one DNA cleavage ability of Cas is inactivated (CRISPR-mutant Cas) is used as a nucleic acid sequence-recognizing module.

FIG. 1 is a schematic illustration showing the double stranded DNA modification method of the present invention using CRISPR-mutant Cas as a nucleic acid sequence-recognizing module.

The nucleic acid sequence-recognizing module of the present invention using CRISPR-mutant Cas is provided as a complex of an RNA molecule consisting of a guide RNA complementary to the target nucleotide sequence and tracrRNA necessary for recruiting mutant Cas protein, and a mutant Cas protein.

The Cas protein used in the present invention is not particularly limited as long as it belongs to the CRISPR system, and is preferably Cas9. Examples of Cas9 include, but are not limited to, Cas9 (SpCas9) from *Streptococcus pyogenes*, Cas9 (StCas9) from *Streptococcus thermophilus* and the like, preferably SpCas9. As a mutant Cas used in the present invention, either a Cas having cleavage ability of both strands of the double stranded DNA is inactivated, or a Cas having nickase activity wherein only one of the cleavage ability of only one of the strands is inactivated, can be used. For example, in the case of SpCas9, a D10A mutant wherein the 10th Asp residue is converted to an Ala residue and lacking cleavage ability of a strand opposite to the strand forming a complementary strand with a guide RNA, or H840A mutant wherein the 840th His residue is converted to an Ala residue and lacking cleavage ability of strand complementary to guide RNA, or a double mutant thereof can be used, and another mutant Cas can be used similarly.

A nucleic acid base converting enzyme is provided as a complex with mutant Cas by a method similar to the linking scheme with the above-mentioned zinc finger and the like. Alternatively, a nucleic acid base converting enzyme and mutant Cas can also be linked by utilizing RNA scaffold with RNA aptamers MS2F6, PP7 and the like and binding proteins thereto. Guide RNA forms a complementary strand with the target nucleotide sequence, mutant Cas is recruited by the attached tracrRNA and mutant Cas recognizes DNA cleavage site recognition sequence PAM (protospacer adjacent motif) (when SpCas9 is used, PAM is 3 bases of NGG (N is any base), and, theoretically, can target any position on the genome). One or both DNAs cannot be cleaved, and, due to the action of the nucleic acid base converting enzyme linked to the mutant Cas, base conversion occurs in the targeted site (appropriately adjusted within several hundred bases including whole or partial target nucleotide sequence) and a mismatch occurs in the double stranded DNA. When the mismatch is not correctly repaired, and when repaired such that a base of the opposite strand forms a pair with a base of the converted strand, or when another nucleotide is further converted or when one to several dozen bases are deleted or inserted during repair, various mutations are introduced (see, e.g., FIG. 2).

Even when CRISPR-mutant Cas is used as a nucleic acid sequence-recognizing module, a nucleic acid sequence-recognizing module and a nucleic acid base converting enzyme are introduced, desirably in the form of a nucleic acid encoding same, into a cell having a double stranded DNA of interest, similar to when zinc finger and the like are used as a nucleic acid sequence-recognizing module.

A DNA encoding Cas can be cloned by a method similar to the above-mentioned method for a DNA encoding a nucleic acid base converting enzyme, from a cell producing the enzyme. A mutant Cas can be obtained by introducing a mutation to convert an amino acid residue of the part important for the DNA cleavage activity (e.g., 10th Asp residue and 840th His residue for Cas9, though not limited thereto) to another amino acid, into a DNA encoding cloned Cas, by a site specific mutation induction method known per se.

Alternatively, a DNA encoding mutant Cas can also be constructed as a DNA having codon usage suitable for expression in a host cell to be used, by a method similar to those mentioned above for a DNA encoding a nucleic acid sequence-recognizing module and a DNA encoding a nucleic acid base converting enzyme, and in a combination with chemical synthesis or PCR method or Gibson Assembly method. For example, CDS sequence and amino acid sequence optimized for the expression of SpCas9 in eukaryotic cells are shown in SEQ ID NOs: 5 and 6. In the sequence shown in SEQ ID NO: 5, when "A" is converted to "C" in base No. 29, a DNA encoding a D10A mutant can be obtained, and when "CA" is converted to "GC" in base Nos. 2518-2519, a DNA encoding an H840A mutant can be obtained.

A DNA encoding a mutant Cas and a DNA encoding a nucleic acid base converting enzyme may be linked to allow for expression as a fusion protein, or designed to be separately expressed using a binding domain, intein or the like, and form a complex in a host cell via protein-protein interaction or protein ligation.

The obtained DNA encoding a mutant Cas and/or a nucleic acid base converting enzyme can be inserted into the downstream of a promoter of an expression vector similar to the one mentioned above, according to the host.

On the other hand, a DNA encoding guide RNA and tracrRNA can be obtained by designing an oligoDNA sequence linking guide RNA sequence complementary to the target nucleotide sequence and known tracrRNA sequence (e.g., gttttagagctagaaatagcaagt-taaaataaggctagtccgttatcaactt-gaaaaagtggcaccgagtcggtggtgctttt; SEQ ID NO: 7) and chemically synthesizing using a DNA/RNA synthesizer.

While the length of the guide RNA sequence is not particularly limited as long as it can specifically bind to a target nucleotide sequence, for example, it is 15-30 nucleotides, preferably 18-24 nucleotides.

While a DNA encoding guide RNA and tracrRNA can also be inserted into an expression vector similar to the one mentioned above, according to the host. As the promoter, pol III promoter (e.g., SNR6, SNR52, SCR1, RPR1, U6, H1 promoter etc.) and terminator (e.g., T6 sequence) are preferably used.

An RNA encoding mutant Cas and/or a nucleic acid base converting enzyme can be prepared by, for example, transcription to mRNA in an in vitro transcription system known per se by using a vector encoding the above-mentioned mutant Cas and/or DNA encoding a nucleic acid base converting enzyme as a template.

Guide RNA-tracrRNA can be obtained by designing an oligoDNA sequence in which a sequence complementary to the target nucleotide sequence and known tracrRNA sequence are linked, and chemically synthesizing using a DNA/RNA synthesizer.

A DNA or RNA encoding mutant Cas and/or a nucleic acid base converting enzyme, guide RNA-tracrRNA or a DNA encoding same can be introduced into a host cell by a method similar to the above, according to the host.

Figure 3:
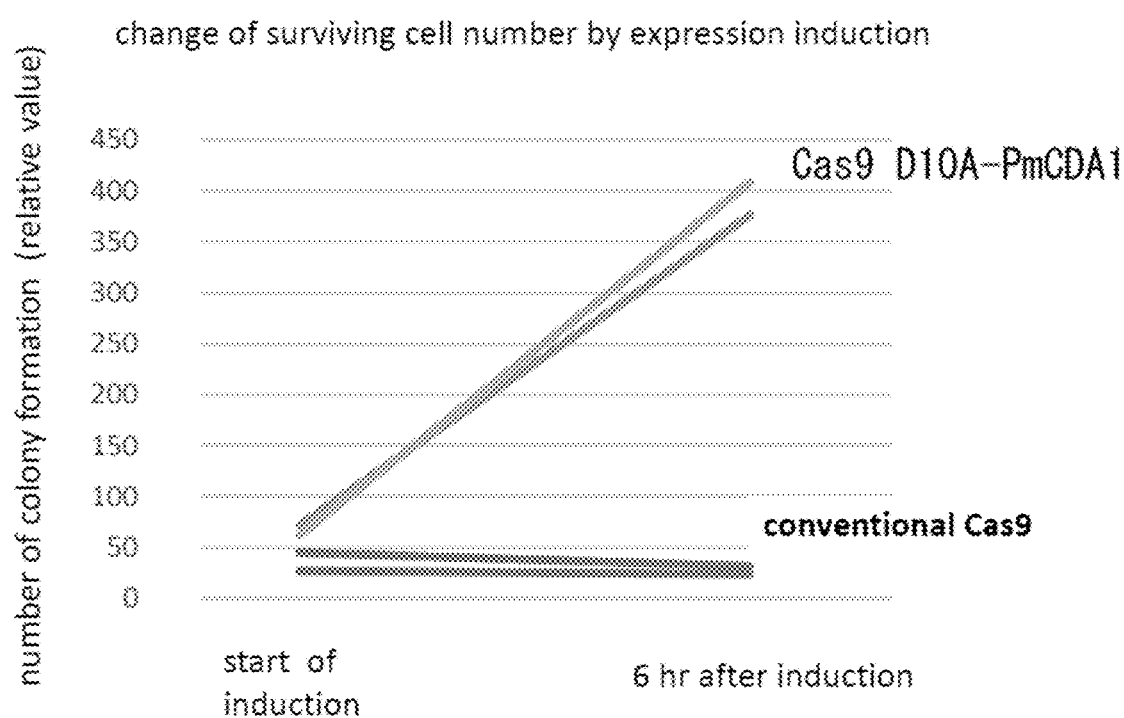
FIG. 3 shows changes in the number of surviving cells after expression induction when a CRISPR-Cas9 system using a D10A mutant of Cas9 having a nickase activity and a deaminase, PmCDA1, are used in combination (nCas9 D10A-PmCDA1), and when conventional Cas9 having a DNA double strand cleavage ability is used.

Since conventional artificial nuclease accompanies Double-stranded DNA breaks (DSB), inhibition of growth and cell death assumedly caused by disordered cleavage (off-target cleavage) of chromosome may occur by targeting a sequence in the genome. The effect thereof is particularly fatal for many microorganisms and prokaryotes, and prevents applicability. In the present invention, mutation is introduced not by DNA cleavage but by a conversion reaction of the substituent on the DNA base (particularly deamination reaction), and therefore, drastic reduction of toxicity can be realized. In fact, as shown in the comparison tests using a budding yeast as a host in the below-mentioned Examples, when Cas9 having a conventional type of DSB activity is used, the number of surviving cells decreases by induction of expression, whereas it was confirmed that the cells continued to grow and the number of surviving cells increased by the technique of the present invention using a combination of mutant Cas and a nucleic acid base converting enzyme in combination (FIG. 3).

The modification of the double stranded DNA in the present invention does not preclude occurrence of cleavage of the double stranded DNA in a site other than the targeted site (appropriately adjusted within several hundred bases including whole or partial target nucleotide sequence). However, one of the greatest advantages of the present invention is avoidance of toxicity by off-target cleavage, which is generally applicable to any species. In one preferable embodiment, therefore, the modification of the double stranded DNA in the present invention is not associated with cleavage of DNA strand not only in a targeted site of a selected double stranded DNA but in other sites.

As shown in the below-mentioned Examples, when Cas having a nickase activity capable of cleaving only one of the strands of the double stranded DNA is used as a mutant Cas (FIG. 5), the mutation introduction efficiency increases as compared to when mutant Cas which is incapable of cleaving both strands is used. Therefore, for example, besides a nucleic acid sequence-recognizing module and a nucleic acid base converting enzyme, linking a protein having a nickase activity, thereby cleaving only a DNA single strand in the vicinity of the target nucleotide sequence, the mutation introduction efficiency can be improved while avoiding the strong toxicity of DSB.

Figure 6:
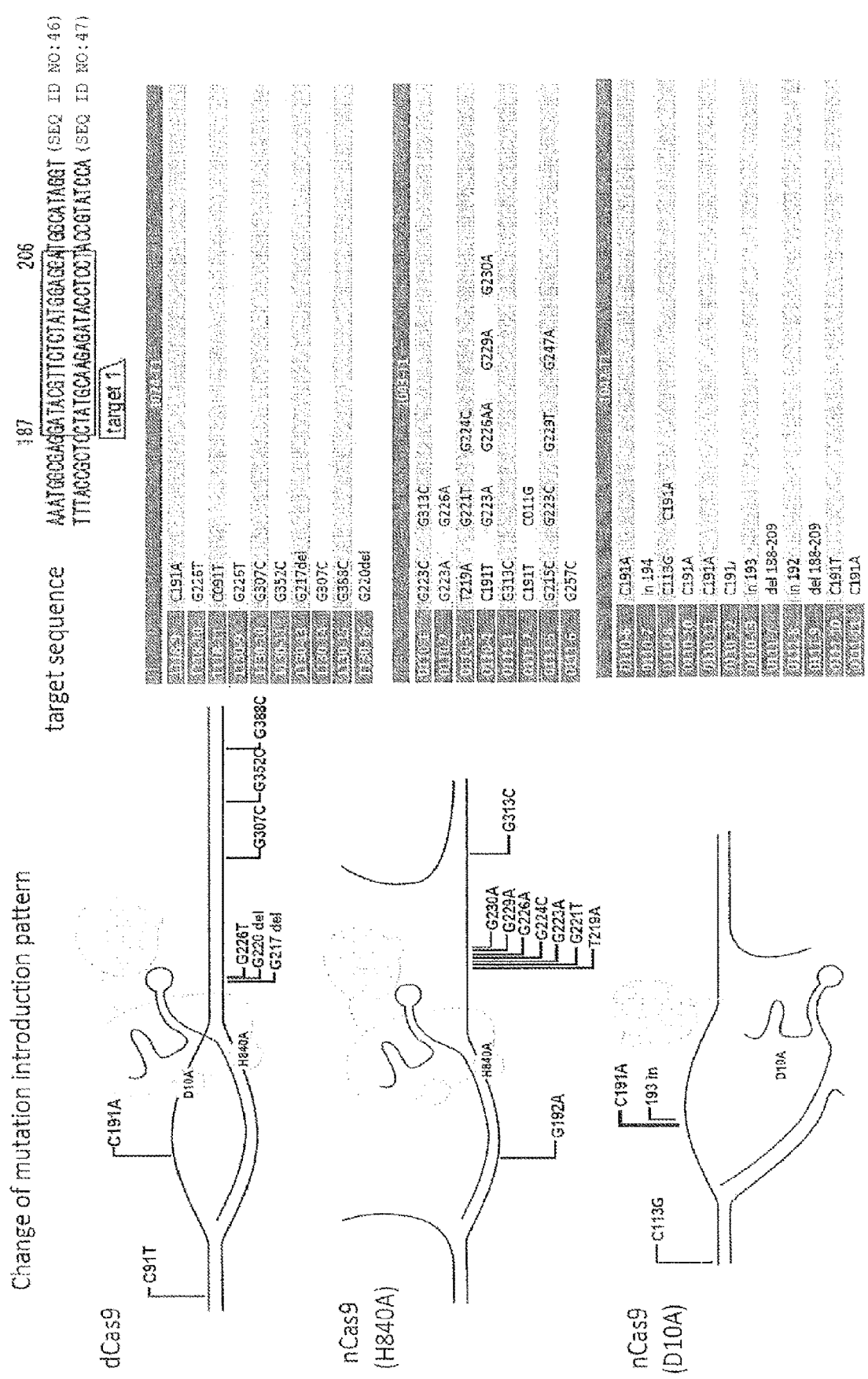
FIG. 6 shows that in the case where a double stranded DNA is not cleaved, the area of mutation introduction region and frequency thereof change depending on which one of the single strands is cleaved.

Furthermore, a comparison of the effects of mutant Cas having two kinds of nickase activity of cleaving different strand reveals that using one of the mutant Cas results in mutated sites accumulating near the center of the target nucleotide sequence, and using another mutant Cas results in various mutations which are randomly introduced into region of several hundred bases from the target nucleotide sequence (FIG. 6). Therefore, by selecting a strand to be cleaved by the nickase, a mutation can be introduced into a particular nucleotide or nucleotide region at a pinpoint, or various mutations can be randomly introduced into a comparatively wide range, which can be properly adopted according to the object. For example, when the former technique is applied to genetically diseased iPS cell, a cell transplantation therapeutic agent with a lower risk of rejection can be produced by repairing mutation of the pathogenic gene in an iPS cell produced from the patients' own cell, and differentiating the cell into the somatic cell of interest.

Example 7 and the subsequent Examples mentioned below show that a mutation can be introduced into a particular nucleotide almost at a pinpoint. For pinpoint introduction of a mutation into a desired nucleotide, the target nucleotide sequence should be set to show certain regularity of the positional relationship between a nucleotide desired to be introduced with a mutation and the target nucleotide sequence. CRISPR-Cas system is used as a nucleic acid sequence-recognizing module and AID is used as a nucleic acid base converting enzyme, the target nucleotide sequence can be designed such that C (or G in the opposite strand) into which a mutation is desired to be introduced is at 2-5 nucleotides from the 5'-end of the target nucleotide sequence. As mentioned above, the length of the guide RNA sequence can be appropriately determined to fall between 15-30 nucleotides, preferably 18-24 nucleotides. Since the guide RNA sequence is a sequence complementary to the target nucleotide sequence, the length of the target nucleotide sequence changes when the length of the guide RNA sequence is changed; however, the regularity that a mutation is likely to be introduced into C or G at 2-5 nucleotides from the 5'-end irrespective of the length of the nucleotide, is maintained (FIG. 12). Therefore, by appropriately determining the length of the target nucleotide sequence (guide RNA as a complementary strand thereof), the site of a base into which a mutation can be introduced can be shifted. As a result, restriction by DNA cleavage site recognition sequence PAM (NGG) can also be removed, and the degree of freedom of mutation introduction becomes higher.

Figure 4:
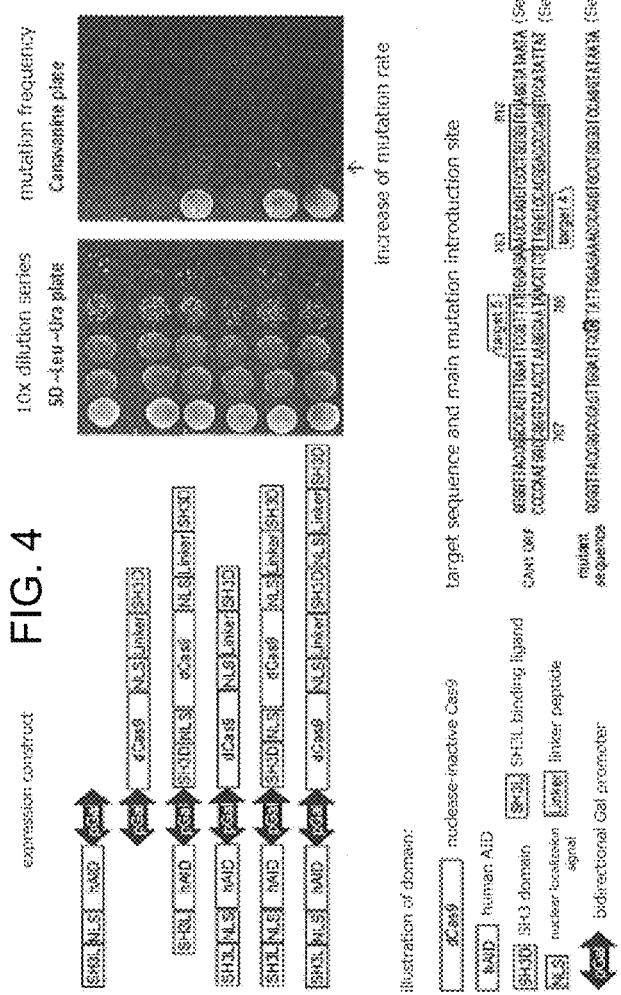
FIG. 4 shows the results when a plurality of expression constructs are constructed such that human AID deaminase and dCas9 are linked via SH3 domain and a binding ligand thereof, wherein the express constructs are introduced into a budding yeast together with two kinds of gRNA (targeting sequences of target 4 and target 5).
Figure 7:
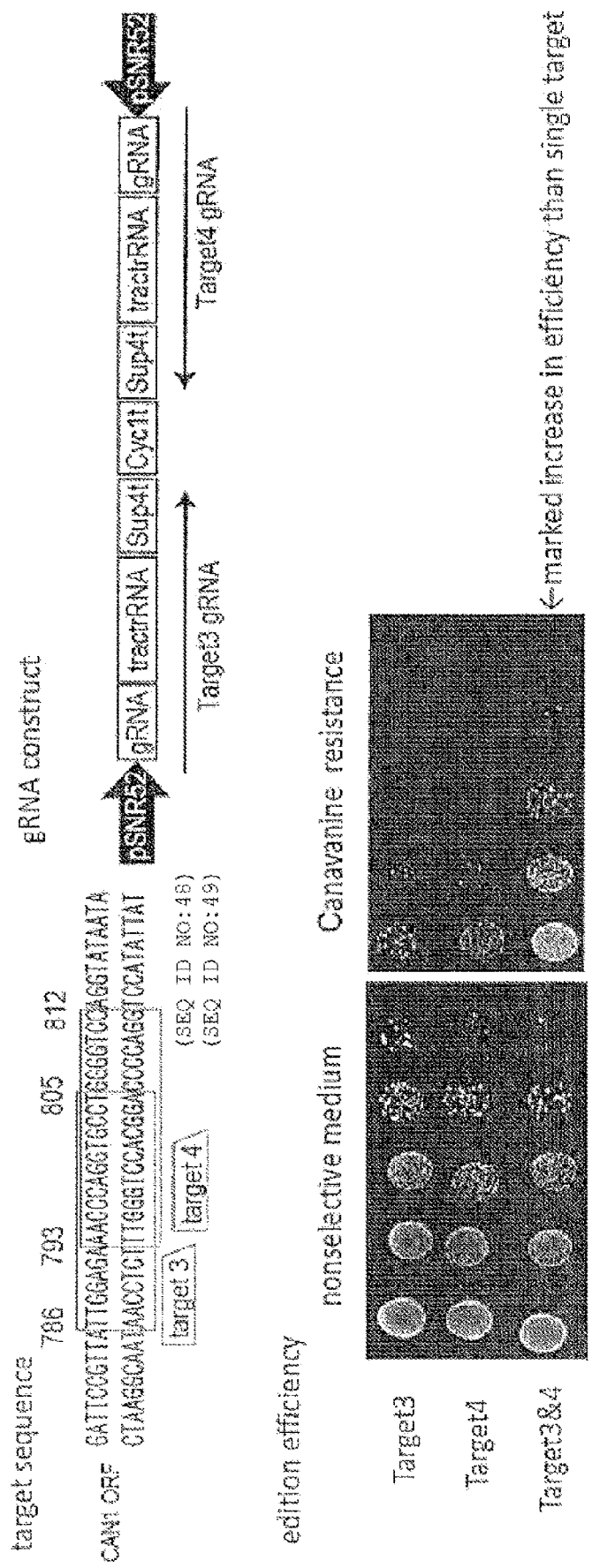
FIG. 7 shows that extremely high mutation introduction efficiency can be realized by targeting two regions in proximity.

As shown in the below-mentioned Examples, when sequence-recognizing modules are produced corresponding to a plurality of target nucleotide sequences in proximity, and simultaneously used, the mutation introduction efficiency drastically increases relative to when a single nucleotide sequence is used as a target (FIG. 7). As the effect thereof, similar mutation induction is realized even when both target nucleotide sequences partly overlap or when the both are apart by about 600 bp. It can occur when both target nucleotide sequences are in the same direction (target nucleotide sequences are present on the same strand) (FIG. 7), and when they are opposed (target nucleotide sequences are present on each strand of double stranded DNA) (FIG. 4).

Figure 8:
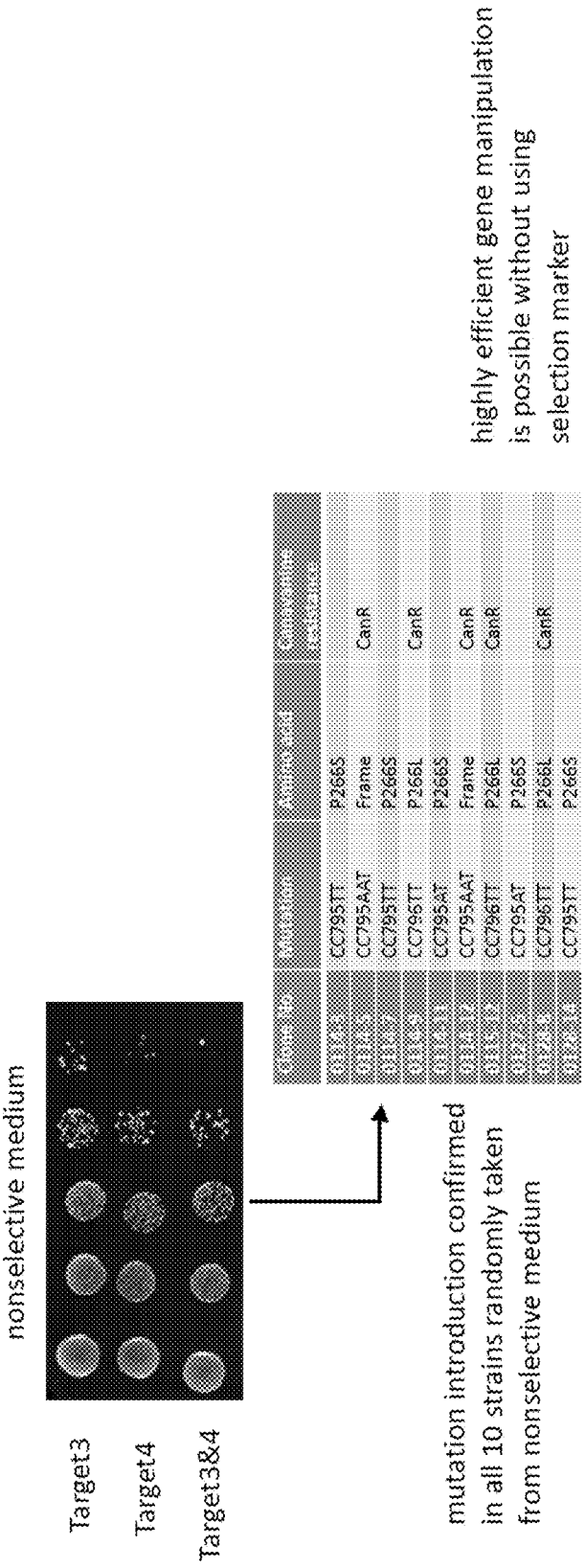
FIG. 8 shows that the genetic modification method of the present invention does not require selection by marker. It was found that mutation was introduced into all colonies sequenced.

As shown in the below-mentioned Examples, the genome sequence modification method of the present invention can introduce mutation into almost all cells in which the nucleic acid-modifying enzyme complex of the present invention has been expressed, by selecting a suitable target nucleotide sequence (FIG. 8). Thus, insertion and selection of a selection marker gene, which are essential in the conventional genome editing, are not necessary. This dramatically facilitates and simplifies gene manipulation and extends the applicability to crop breeding and the like since a recombinant organism with foreign DNA is not produced.

Figure 9:
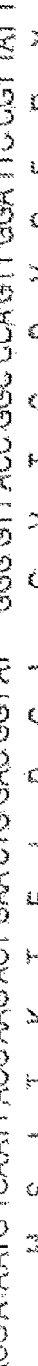
FIG. 9 shows that a plurality of sites in a genome can be simultaneously edited by the genetic modification method of the present invention. The upper panel shows the nucleotide sequence and amino acid sequence of the target site of each gene, and an arrow on the nucleotide sequence shows the target nucleotide sequence. The number at the arrow end or arrow head indicates the position of the target nucleotide sequence terminus on ORF. The lower panel shows the results of sequencing of the target site in each 5 clones of red (R) and white (W) colonies. In the sequences, the nucleotides indicated with outline characters show occurrence of base conversion. As for responsiveness to canavanine (Can$^R$), R shows resistance, and S shows sensitivity.

Since the genome sequence modification method of the present invention shows extremely high mutation introduction efficiency, and does not require selection by markers, a plurality of DNA regions at completely different positions can be modified as targets (FIG. 9). Therefore, in one preferable embodiment of the present invention, two or more kinds of nucleic acid sequence-recognizing modules that specifically bind to different target nucleotide sequences (which may be present in one target gene of interest, or two or more different target genes of interest, which may be present on the same chromosome or different chromosomes) can be used. In this case, each one of these nucleic acid sequence-recognizing modules and nucleic acid base converting enzyme form a nucleic acid-modifying enzyme complex. Here, a common nucleic acid base converting enzyme can be used. For example, when CRISPR-Cas system is used as a nucleic acid sequence-recognizing module, a common complex of a Cas protein and a nucleic acid base converting enzyme (including fusion protein) is used, and two or more kinds of chimeric RNAs of tracrRNA and each of two or more guide RNAs that respectively form a complementary strand with a different target nucleotide sequences are produced and used as guide RNA-tracrRNAs. On the other hand, when zinc finger motif, TAL effector and the like are used as nucleic acid sequence-recognizing modules, for example, a nucleic acid base converting enzyme can be fused with a nucleic acid sequence-recognizing module that specifically binds to a different target nucleotide.

To express the nucleic acid-modifying enzyme complex of the present invention in a host cell, as mentioned above, an expression vector containing a DNA encoding the nucleic acid-modifying enzyme complex, or an RNA encoding the nucleic acid-modifying enzyme complex is introduced into a host cell. For efficient introduction of mutation, it is desirable to maintain an expression of nucleic acid-modifying enzyme complex at a given level or above for not less than a given period. From such aspect, introduction of an expression vector autonomously replicatable in a host cell (plasmid etc.) is reliable. However, since the plasmid etc. are foreign DNAs, they are preferably removed rapidly after successful introduction of mutation. Therefore, although it varies depending on the kind of host cell and the like, for example, the introduced plasmid is desirably removed from the host cell after a lapse of 6 hr-2 days from the introduction of an expression vector by using various plasmid removal methods which are well known in the art.

Alternatively, as long as sufficient expression of a nucleic acid-modifying enzyme complex for the introduction of mutation is achieved, it is also preferable to introduce mutation into the target double stranded DNA of interest by transient expression by using an expression vector without autonomous replicatability in a host cell (e.g., vector lacking replication origin that functions in a host cell and/or gene encoding protein necessary for replication etc.) or RNA.

Expression of target gene is suppressed while the nucleic acid-modifying enzyme complex of the present invention is expressed in a host cell to perform a nucleic acid base conversion reaction. Therefore, it was difficult to directly edit a gene essential for the survival of the host cell as a target gene (result in side effects such as growth inhibition of host, unstable mutation introduction efficiency, mutation of site different from target and the like). In the present invention, direct editing of an essential gene has been successfully and efficiently realized by causing a nucleic acid base conversion reaction at a desired stage, and transiently expressing the nucleic acid-modifying enzyme complex of the present invention in a host cell for a period necessary for stabilizing the modification of the targeted site. While the period necessary for a nucleic acid base conversion reaction and stabilizing the modification of the targeted site varies depending on the kind of the host cell, culture conditions and the like, host cells of 2-20 generations are generally considered to be necessary. For example, when the host cell is a yeast or bacterium (e.g., *Escherichia coli*), expression of a nucleic acid-modifying enzyme complex needs to be induced for 5-10 generations. Those of ordinary skill in the art can appropriately determine a preferable expression induction period based on the doubling time of the host cell under culture conditions used. For example, when a budding yeast is subjected to liquid culture in a 0.02% galactose inducer medium, the expression induction period is, for example, 20-40 hr. The expression induction period of the nucleic acid encoding the nucleic acid-modifying enzyme complex of the present invention may be extended beyond the above-mentioned "period necessary for establishing the modification of the targeted site" to the extent not causing side effects to the host cell.

Figure 13:
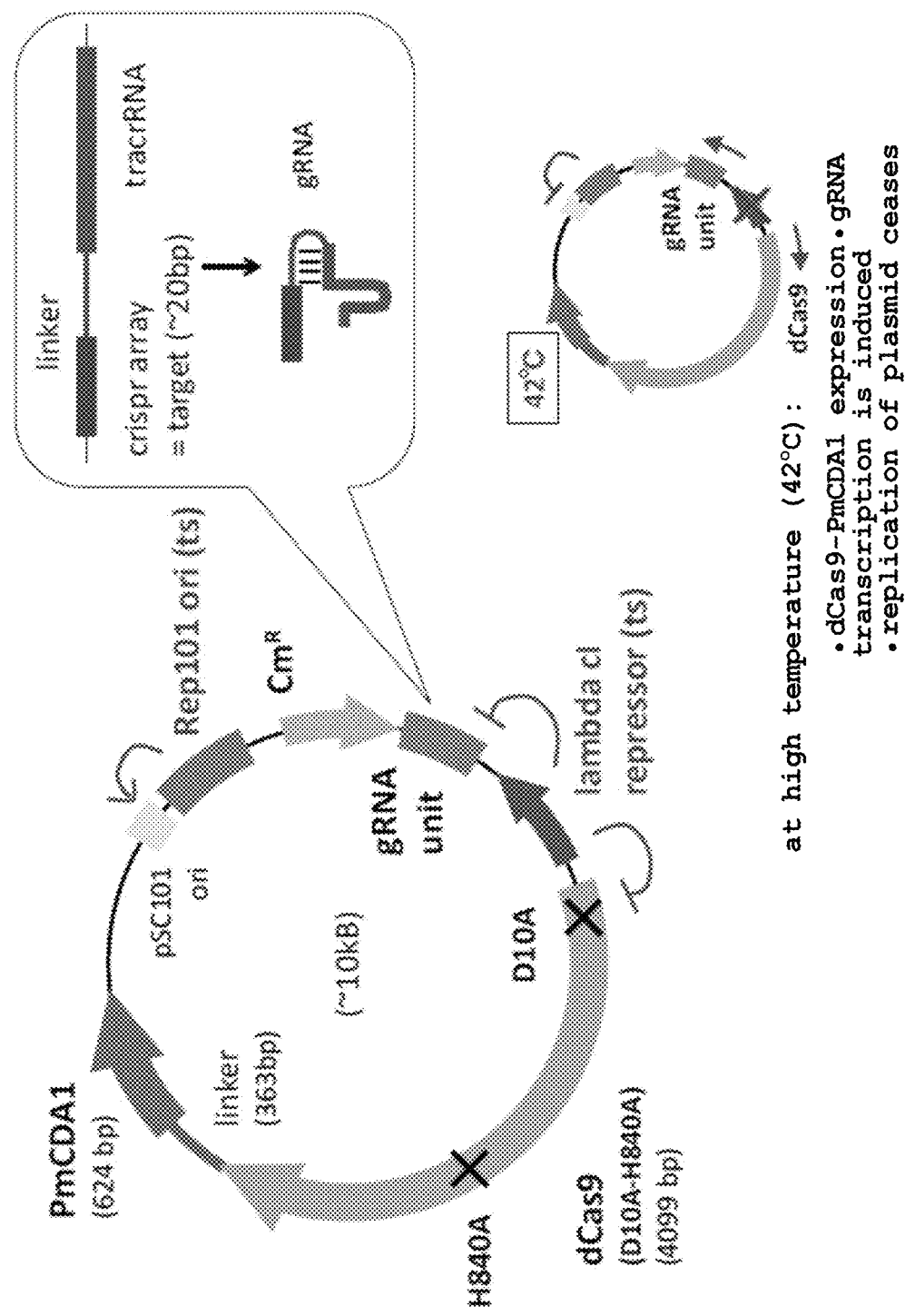
FIG. 13 is a schematic illustration showing a temperature sensitive plasmid for mutation introduction, which was used in Example 11.
Figure 14:
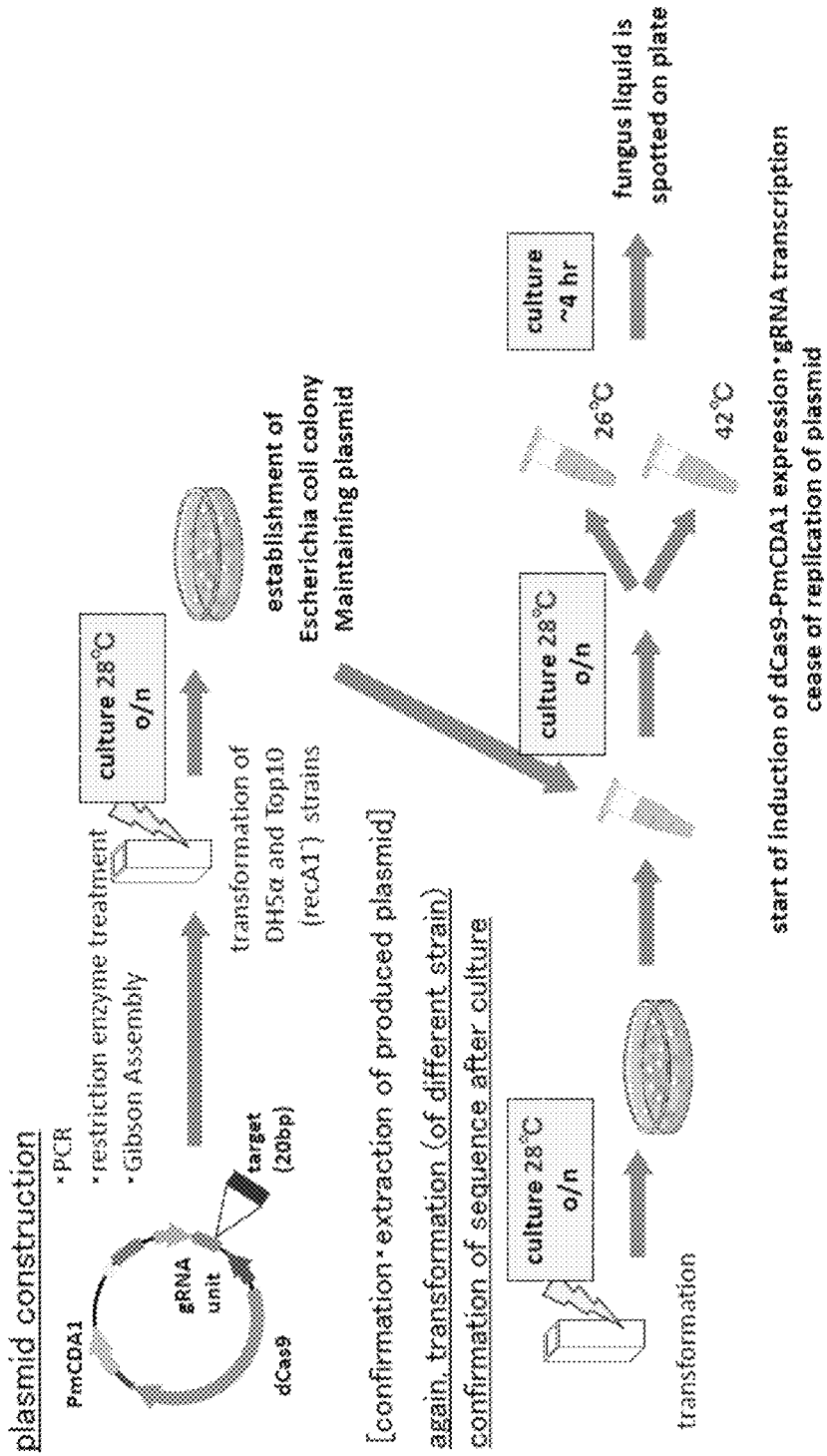
FIG. 14 shows the protocol of mutation introduction in Example 11.
Figure 15:
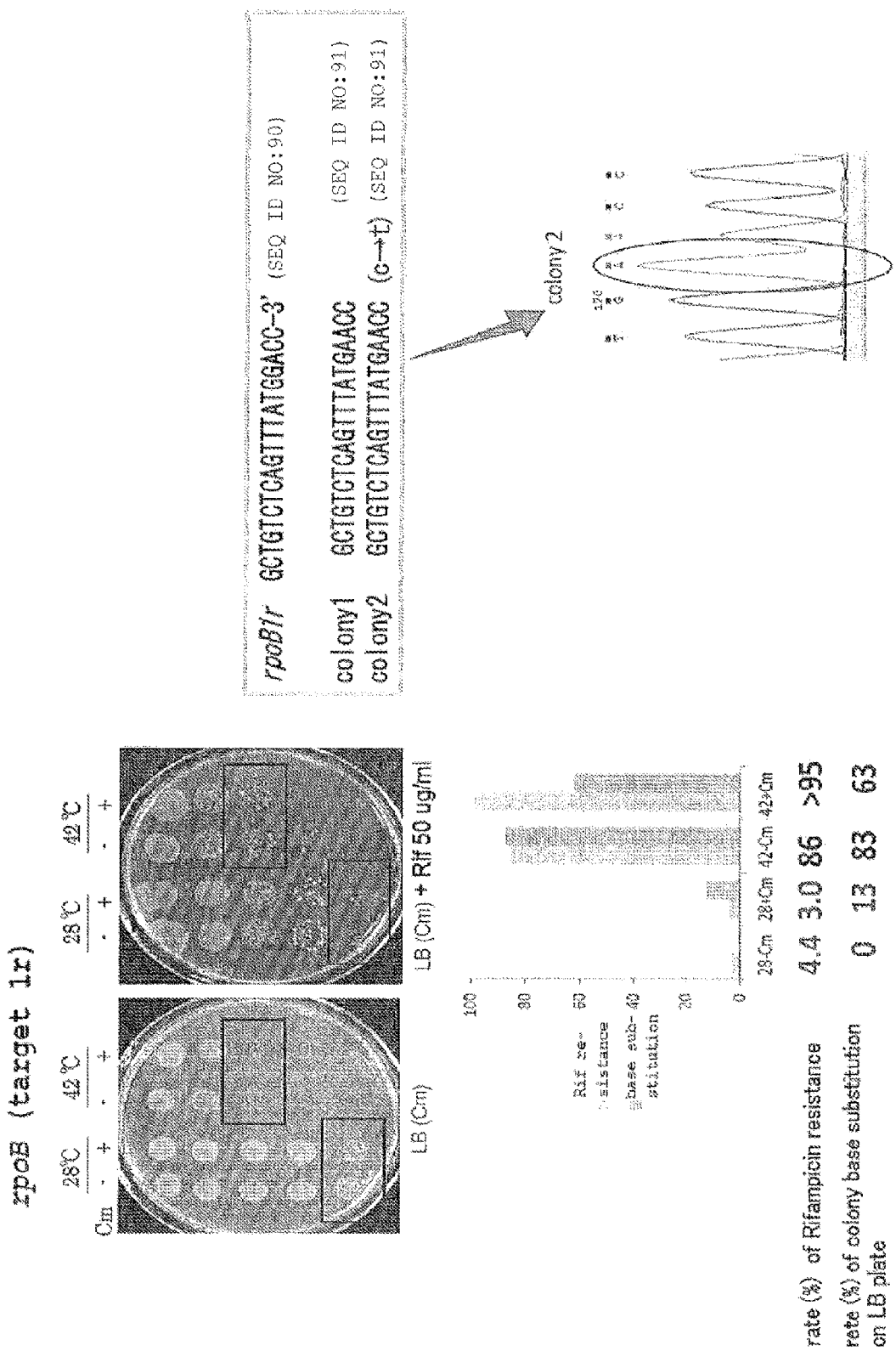
FIG. 15 shows the results of introduction of mutation into the rpoB gene in Example 11.

As a means for transiently expressing the nucleic acid-modifying enzyme complex of the present invention at a desired stage for a desired period, a method comprising producing a construct (expression vector) containing a nucleic acid encoding the nucleic acid-modifying enzyme complex (a DNA encoding a guide RNA-tracrRNA and a DNA encoding a mutant Cas and nucleic acid base substitution enzyme in the case of CRISPR-Cas system), in a manner that the expression period can be controlled, and introducing the construct into a host cell can be used. The "manner that the expression period can be controlled" is specifically, for example, a nucleic acid encoding the nucleic acid-modifying enzyme complex of the present invention placed under regulation of an inducible regulatory region. While the "inducible regulatory region" is not particularly limited, it is, for example, an operon of a temperature sensitive (ts) mutation repressor and an operator regulated thereby in microorganism cells of bacterium (e.g., *Escherichia coli*), yeast and the like. Examples of the ts mutation repressor include, but are not limited to, ts mutation of cI repressor from λphage. In the case of λphage cI repressor (ts), it is linked to an operator to suppress expression of gene in the downstream at not more than 30° C. (e.g., 28° C.). At a high temperature of not less than 37° C. (e.g., 42° C.), it is dissociated from the operator to allow for induction of gene expression (FIGS. 13 and 14). Therefore, the period when the expression of the target gene is suppressed can be minimized by culturing a host cell introduced with a nucleic acid encoding nucleic acid-modifying enzyme complex generally at not more than 30° C., raising the temperature to not less than 37° C. at an appropriate stage, performing culture for a given period to carry out a nucleic acid base conversion reaction and, after introduction of mutation into the target gene, rapidly lowering the temperature to not more than 30° C. Thus, even when an essential gene for the host cell is targeted, it can be efficiently edited while suppressing the side effects (FIG. 15).

When temperature sensitive mutation is utilized, for example, a temperature sensitive mutant of a protein necessary for autonomous replication of a vector is included in a vector containing a DNA encoding the nucleic acid-modifying enzyme complex of the present invention. As a result, autonomous replication becomes impossible rapidly after expression of the nucleic acid-modifying enzyme complex, and the vector naturally falls off during the cell division. Examples of the temperature sensitive mutant protein include, but are not limited to, a temperature sensitive mutant of Rep101 ori necessary for the replication of pSC101 ori. Rep101 ori (ts) acts on pSC101 ori to enable autonomous replication of plasmid at not more than 30° C. (e.g., 28° C.), but loses function at not less than 37° C. (e.g., 42° C.), and plasmid cannot replicate autonomously. Therefore, a combined use with cI repressor (ts) of the above-mentioned λphage simultaneously enables transient expression of the nucleic acid-modifying enzyme complex of the present invention, and removal of the plasmid.

On the other hand, when a higher eukaryotic cell such as animal cell, insect cell, plant cell and the like is used as a host cell, a DNA encoding the nucleic acid-modifying enzyme complex of the present invention is introduced into a host cell under regulation of an inducible promoter (e.g., metallothionein promoter (induced by heavy metal ion), heat shock protein promoter (induced by heat shock), Tet-ON/Tet-OFF system promoter (induced by addition or removal of tetracycline or a derivative thereof), steroid-responsive promoter (induced by steroid hormone or a derivative thereof) etc.), the induction substance is added to the medium (or removed from the medium) at an appropriate stage to induce expression of the nucleic acid-modifying enzyme complex, culture is performed for a given period to carry out a nucleic acid base conversion reaction and, introduction of mutation into the target gene, transient expression of the nucleic acid-modifying enzyme complex can be realized.

In Prokaryotic cells such as *Escherichia coli* and the like, inducible promoters can also be used. Examples of such inducible promoters include, but are not limited to, lac promoter (induced by IPTG), cspA promoter (induced by cold shock), araBAD promoter (induced by arabinose) and the like.

Alternatively, the above-mentioned inducible promoters can also be utilized as a vector removal mechanism when higher eukaryotic cells such as animal cell, insect cell, plant cell and the like are used as a host cell. That is, a vector is loaded with a replication origin that can function in a host cell, and a nucleic acid encoding a protein necessary for replication thereof (e.g., SV40 ori and large T antigen, oriP and EBNA-1 etc. for animal cells), and the expression of the nucleic acid encoding the protein is regulated by the above-mentioned inducible promoter. As a result, while the vector is autonomously replicatable in the presence of an induction substance, when the induction substance is removed, autonomous replication does not occur, and the vector naturally falls off during cell division (conversely, autonomous replication becomes impossible by the addition of tetracycline and doxycycline in the case of Tet-OFF system vector).

The present invention is explained in the following by referring to Examples, which are not to be construed as limitative.

EXAMPLES

In the below-mentioned Examples 1-6, experiments were performed as follows.

Cell Line, Culture, Transformation, and Expression Induction

Budding yeast *Saccharomyces cerevisiae* BY4741 strain (requiring leucine and uracil) was cultured in a standard YPDA medium or SD medium with a Dropout composition satisfying the auxotrophicity. The culture performed was standing culture in an agar plate or shaking culture in a liquid medium between 25° C. and 30° C. Transformation was performed by a lithium acetate method, and selection was made in SD medium matching appropriate auxotrophicity. For expression induction by galactose, after preculture overnight in an appropriate SD medium, culture in SR medium overnight with carbon source changed from 2% glucose to 2% raffinose, and further culture in SGal medium for 3 hr to about two nights with carbon source changed to 0.2-2% galactose were conducted for expression induction.

For the measurement of the number of surviving cells and Can1 mutation rate, a cell suspension was appropriately diluted, and applied on SD plate medium and SD-Arg+60 mg/l Canavanine plate medium or SD+300 mg/l Canavanine plate medium, and the number of colonies that emerge 3 days later was counted as the number of surviving cells. Using the number of surviving colonies in SD plate as the total number of cells, and the number of surviving colonies in Canavanine plate as the number of resistant mutant strain, the mutation rate was calculated and evaluated. The site of mutation introduction was identified by amplifying DNA fragments containing the target gene region of each strain by a colony PCR method, performing DNA sequencing, and performing an alignment analysis based on the sequence of Saccharomyces Genome Database (www.yeastgenome.org).

Nucleic Acid Operation

DNA was processed or constructed by any of PCR method, restriction enzyme treatment, ligation, Gibson Assembly method, and artificial chemical synthesis. For plasmid, as the yeast •*Escherichia coli* shuttle vector, pRS315 for leucine selection and pRS426 for uracil selection were used as the backbone. Plasmid was amplified by *Escherichia coli* line XL-10 gold or DH5α, and introduced into yeast by the lithium acetate method.

Construct

For inducible expression, budding yeast pGal1/10 (SEQ ID NO: 8), which is a bidirectional promoter inducible by galactose, was used. At the downstream of a promoter, a nuclear localization signal (ccc aag aag aag agg aag gtg; SEQ ID NO: 9(PKKKRV; encoding SEQ ID NO: 10)) was added to Cas9 gene ORF from *Streptococcus pyogenes* having a codon optimized for eukaryon expression (SEQ ID NO: 5) and ORF (SEQ ID NO: 1 or 3) of deaminase gene (PmCDA1 from Petromyzon marinus or hAID from human) was ligated via a linker sequence, and expressed as a fusion protein. As a linker sequence, GS linker (repeat of ggt gga gga ggt tct; SEQ ID NO: 11 (encoding GGGGS; SEQ ID NO: 12)), Flag tag (gac tat aag gac cacgac gga gac tac aag gat cat gat att gat tac aaa gac gat gac gat aag; SEQ ID NO: 13 (encoding DYKDHDGDYKDHDIDYKDDDDK; SEQ ID NO: 14)), Strep-tag (tgg agc cac ccg cag ttc gaa aaa; SEQ ID NO: 15 (encoding WSHPQFEK; SEQ ID NO: 16)), and other domains are selected and used in combination. Here, particularly, 2×GS, SH3 domain (SEQ ID NO: 17 and 18), and Flag tag were ligated and used. As a terminator, ADH1 terminator from budding yeast (SEQ ID NO: 19) and Top2 terminator (SEQ ID NO: 20) were ligated. In the domain integration method, Cas9 gene ORF was ligated to SH3 domain via 2×GS linker to give one protein, deaminase was added with SH3 ligand sequence (SEQ ID NOs: 21 and 22) as another protein, and they were ligated to Gal1/10 promoter on both sides. And they were simultaneously expressed. These were incorporated into pRS315 plasmid.

In Cas9, mutation to convert the 10th aspartic acid to alanine (D10A, corresponding DNA sequence mutation a29c) and mutation to convert the 840th histidine to alanine (H840A, corresponding DNA sequence mutation ca2518gc) were introduced to remove cleavage ability of either side of DNA strand.

gRNA as a chimeric structure with tracrRNA (from *Streptococcus pyogenes*; SEQ ID NO: 7) was disposed between SNR52 promoter (SEQ ID NO: 23) and Sup4 terminator (SEQ ID NO: 24), and incorporated into pRS426 plasmid. As gRNA target base sequence, CAN1 gene ORF, 187-206 (gatacgttctctatggagga; SEQ ID NO: 25) (target 1), 786-805 (ttggagaaacccaggtgcct; SEQ ID NO: 26) (target 3), 793-812 (aacccaggtgcctggggtcc; SEQ ID NO: 27) (target 4), 563-582 (ttggccaagtcattcaattt; SEQ ID NO: 28) (target 2) and complementary strand sequence of 767-786 (ataacggaatc-caactgggc; SEQ ID NO: 29) (target 5r) were used. For simultaneous expression of a plurality of targets, using a sequence from a promoter to a terminator as one set, and a plurality of the sets were incorporated into the same plasmid. They were introduced into cells along with Cas9-deaminase expression plasmid, intracellularly expressed, and a complex of gRNA-tracrRNA and Cas9-deaminase was formed.

Example 1: Modification of Genome Sequence by Linking DNA Sequence Recognition Ability of CRISPR-Cas to Deaminase PmCDA1

Figure 2:
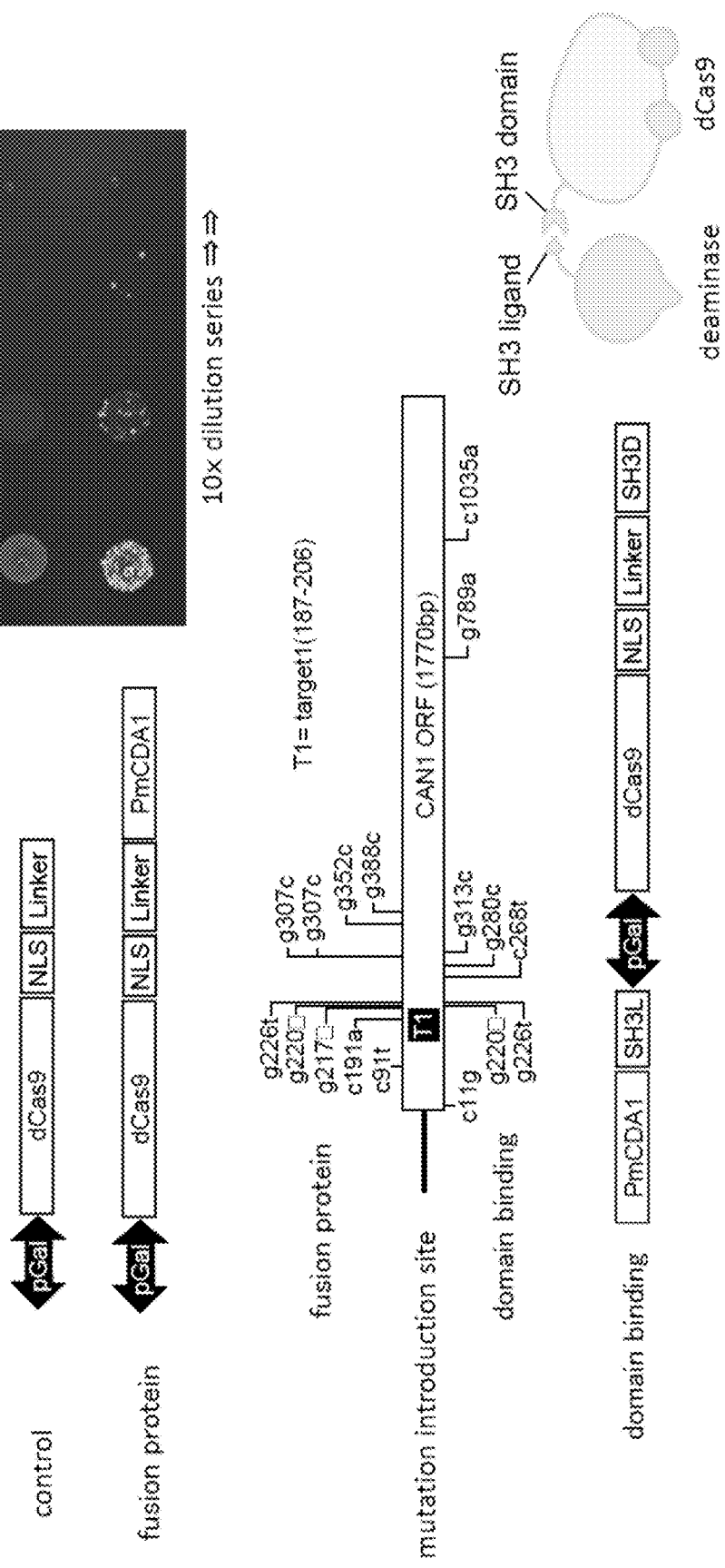
FIG. 2 shows the results of verification, by using a budding yeast, of the effect of the genetic modification method of the present invention comprising a combination of a CRISPR-Cas system and PmCDA1 deaminase from Petromyzon marinus.

To test the effect of genome sequence modification technique of the present invention by utilizing deaminase and CRISPR-Cas nucleic acid sequence recognition ability, introduction of mutation into CAN1 gene encoding canavanine transporter, whose gene deficit results in canavanine-resistance, was attempted. As gRNA, a sequence complementary to 187-206 (target 1) of CAN1 gene ORF was used, a chimeric RNA expression vector obtained by linking thereto tracrRNA from *Streptococcus pyogenes*, and a vector expressing a protein obtained by fusing dCas9 with impaired nuclease activity by introducing mutations (D10A and H840A) into Cas9 (SpCas9) from *Streptococcus pyogenes* with PmCDA1 from Petromyzon marinusas deaminase were constructed, introduced into the budding yeast by the lithium acetate method, and coexpressed. The results are shown in FIG. 2. When cultured on a canavanine-containing SD plate, only the cells subjected to introduction and expression of gRNA-tracrRNA and dCas9-PmCDA1 formed colony. The resistant colony was picked up and the sequence of CAN1 gene region was determined. As a result, it was confirmed that a mutation was introduced into the target nucleotide sequence (target 1) and the vicinity thereof.

Example 2: Drastic Reduction of Side Effects·Toxicity

In conventional Cas9 and other artificial nucleases (ZFN, TALEN), inhibition of growth and cell death assumedly caused by disordered cleavage of chromosome occur by targeting a sequence in the genome. The effect thereof is particularly fatal for many microorganisms and prokaryotes, and prevents applicability.

Therefore, to verify the safety and cell toxicity of the genome sequence modification technique of the present invention, a comparative test with conventional CRISPR-Cas9 was performed. Using sequences (targets 3, 4) in the CAN1 gene as gRNA target, the surviving cells were counted immediately after the start of expression induction by galactose and at 6 hr after the induction based on the colony forming ability on an SD plate. The results are shown in FIG. 3. In conventional Cas9, the growth was inhibited and cell death was induced, which decreased the number of surviving cells. In contrast, by the present technique (nCas9 D10A-PmCDA1), the cells could continue to grow, and the number of surviving cells drastically increased.

Example 3: Use of Different Linking Scheme

Whether mutation can be introduced into a targeted gene even when Cas9 and deaminase are not used as a fusion protein but when a nucleic acid-modifying enzyme complex is formed via a binding domain and a ligand thereof was examined. As Cas9, dCas9 used in Example 1 was used and human AID instead of PmCDA1 was used as deaminase. SH3 domain was fused with the former, and a binding ligand thereof was fused with the latter to produce various constructs shown in FIG. 4. In addition, sequences (target 4,5r) in the CAN1 gene were used as gRNA targets. These constructs were introduced into a budding yeast. As a result, even when dCas9 and deaminase were linked via the binding domain, mutation was efficiently introduced into the targeted site of the CAN1 gene (FIG. 4). The mutation introduction efficiency was remarkably improved by introducing a plurality of binding domains into dCas9. The main site of mutation introduction was 782nd (g782c) of ORF.

Figure 5:
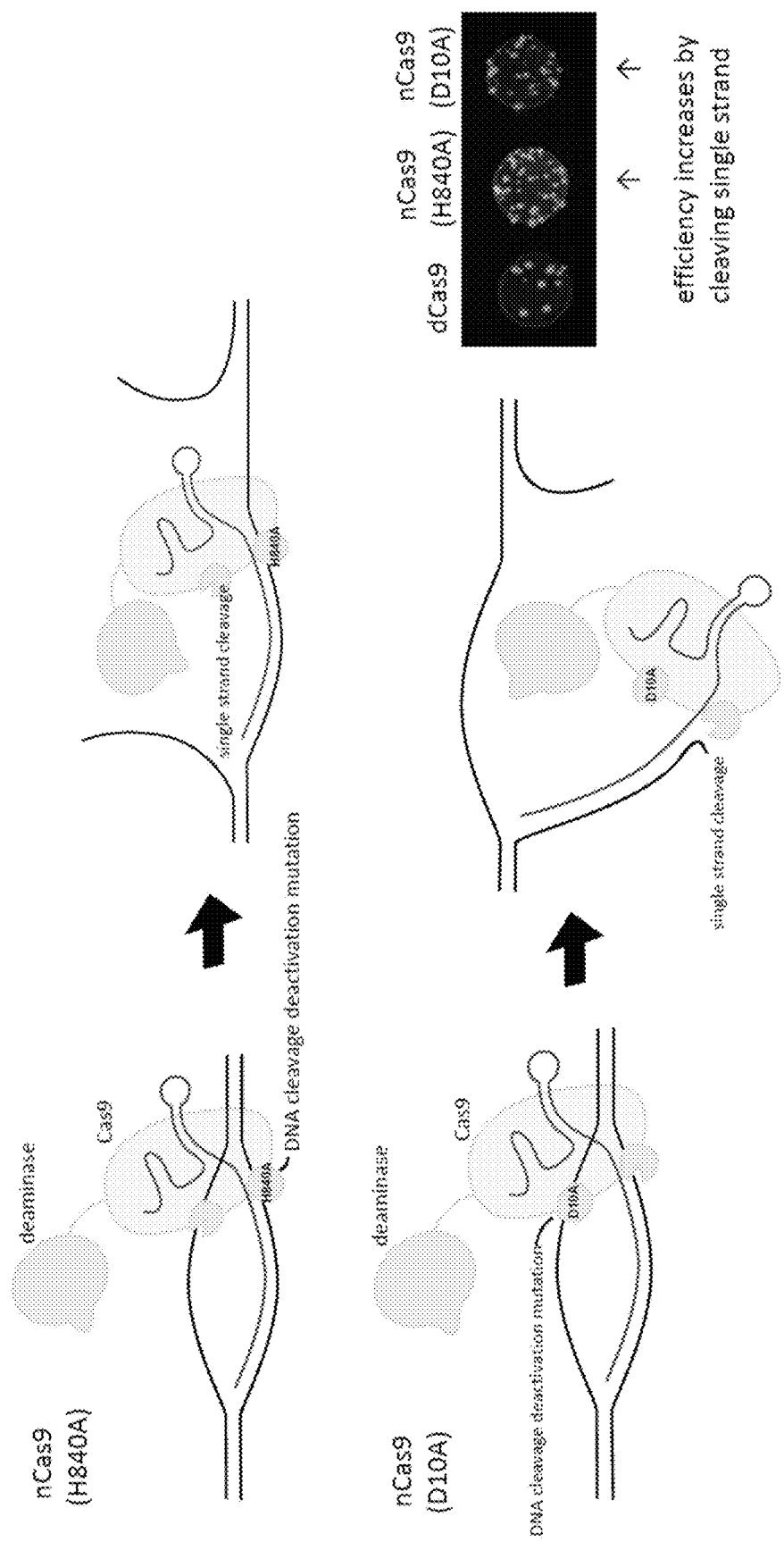
FIG. 5 shows that the mutation introduction efficiency is increased by the use of Cas9 that cleaves either DNA single strand.

Example 4: High Efficiency and Changes in Mutation Pattern by Use of Nickase In the same manner as in Example 1 except that D10A mutant nCas9 (D10A) that cleaves only a strand complementary to gRNA, or H840A mutant nCas9 (H840A) that cleaves only a strand opposite to a strand complementary to gRNA was used instead of dCas9, mutation was introduced into the CAN1 gene, and the sequence in the CAN1 gene region of the colony generated on a canavanine-containing SD plate was examined. It was found that the efficiency increases in the former (nCas9 (D10A)) as compared to dCas9 (FIG. 5), and the mutation gathers in the center of the target sequence (FIG. 6). Therefore, this method enables pinpoint introduction of mutation. On the other hand, it was found in the latter (nCas9 (H840A)) that a plurality of random mutations were introduced into a region of several hundred bases from the targeted nucleotide (FIG. 6) along with an increase in the efficiency as compared to dCas9 (FIG. 5).

Similar remarkable introduction of mutation could be confirmed even when the target nucleotide sequence was changed. In this genome editing system using CRISPR-Cas9 system and cytidine deaminase, it was confirmed as shown in Table 1 that cytosine present within the range of about 2-5 bp from the 5'-side of the target nucleotide sequence (20 bp) were preferentially deaminated. Therefore, by setting the target nucleotide sequence based on this regularity and further combining with nCas9 (D10A), precise genome editing of 1 nucleotide unit is possible. On the other hand, a plurality of mutations can be simultaneously inserted within the range of about several hundred bp in the vicinity of the target nucleotide sequence by using nCas9 (H840A). Furthermore, site specificity may possibly be further varied by changing the linking scheme of deaminase.

These results show that the kind of Cas9 protein can be changed properly according to the object.

TABLE 1

| position of CAN1 gene ORF | sequence (SEQ ID NO:) | site of main mutation introduction |
| --- | --- | --- |
| 187-206 (target 1) | Gatacgttctcta tggagga (25) | c191a, g226t |
| 563-582 (target 2) | Ttggccaagtcat tcaattt (28) | cc567at, c567del |
| 786-805 (target 3) and | Ttggagaaaccca ggtgcct (26) | cc795tt, cc796tt |
| 793-812 (target 4) | Aacccaggtgcct ggggtcc (27) | |
| 767-786 (complementary strand) (target 5r) | Ataacggaatcca actgggc (29) | g782c |

Example 5: Efficiency Increases Synergistically by Targeting a Plurality of DNA Sequences in Proximity Efficiency drastically increased by simultaneously using a plurality of targets in proximity rather than a single target (FIG. 7). In fact, 10-20% of cells had canavanine-resistant mutation (targets 3, 4). In the Figure, gRNA1 and gRNA2 target target 3 and target 4, respectively. As deaminase, PmCDA1 was used. The effect thereof was confirmed to occur not only when the sequences partly overlapped (targets 3, 4), but also when they were apart by about 600 bp (targets 1, 3). The effect was found both when the DNA sequences were in the same direction (targets 3, 4) and opposing (targets 4, 5) (FIG. 4).

Example 6: Genetic Modification not Requiring Selection Marker

As for the cells (Targets 3, 4) in which target 3 and target 4 were targeted in Example 5, 10 colonies were randomly selected from those grown on a non-selected (canavanine-free) plate (SD plate not containing Leu and Ura) and the sequences of the CAN1 gene region were determined. As a result, mutation was introduced into the targeted site of the CAN1 gene in all examined colonies (FIG. 8). That is, editing can be expected in almost all expressed cells by selecting a suitable target sequence according to the present invention. Therefore, insertion of a marker gene and selection, which are essential for the conventional gene manipulation, are not necessary. This dramatically facilitates and simplifies gene manipulation and extends the applicability to crop breeding and the like since a recombinant organism with foreign DNA is not produced.

In the following Examples, experiment techniques shared by Examples 1-6 were performed in the same manner as above.

Example 7: Simultaneous Editing of a Plurality of Sites (Different Gene)

In a general gene manipulation method, mutation of only one site is generally achieved by one operation due to various restrictions. Thus, whether a simultaneous mutation operation of a plurality of sites is possible using the method of the present invention was tested.

Using the ORF of positions 3 to 22 of Ade1 gene of budding yeast BY4741 strain as the first target nucleotide sequence (Ade1 target 5: GTCAATTACGAAGACTGAAC; SEQ ID NO: 30), and the ORF of positions 767-786 (complementary strand) of Can1 gene as the second target nucleotide sequence (Can1 target8 (786-767; ATAACG-GAATCCAACTGGGC; SEQ ID NO: 29), both DNAs encoding chimeric RNAs of two kinds of gRNAs each containing a nucleotide sequence complementary thereto and tracrRNA (SEQ ID NO: 7) were placed on the same plasmid (pRS426), and introduced into BY4741 strain together with plasmid nCas9 D10A-PmCDA1 containing a nucleic acid encoding a fusion protein of mutant Cas9 and PmCDA1, and expressed, and introduction of mutation into the both genes was verified. The cells were cultured in an SD drop-out medium (uracil and leucine deficient; SD-UL) as a base, which maintains plasmid. The cells were appropriately diluted, applied on SD-UL and canavaine addition medium and allowed to form a colony. After 2 days of culture at 28° C., colonies were observed, and the incidence of red colony due to Ade1 mutation, and the survival rate in a canavanine medium were respectively counted. The results are shown in Table 2.

TABLE 2

| medium | incidence of red colony | survival rate in Canavanine medium (Can) | red colony and Can survival rate |
|---|---|---|---|
| SD-UL | 0.54 ± 0.04 | | |
| +canavanine | 0.64 ± 0.14 | 0.51 ± 0.15 | 0.31 ± 0.04 |

As a phenotype, the proportion of introduction of mutation into both Ade1 gene and Can1 gene was high and about 31%.

Then, a colony on an SD-UL medium was subjected to PCR amplification followed by sequencing. Regions containing ORF of each of Ade1 and Can1 were amplified, and sequence information of about 500 b sequences surrounding the target sequence was obtained. To be specific, 5 red colonies and 5 white colonies were analyzed to find conversion of the 5th C of Ade1 gene ORF to G in all red colonies and the 5th C to T in all white colonies (FIG. 9). While the mutation rate of the target is 100%, as the mutation rate in light of the object of gene destruction, the desired mutation rate is 50% since the 5th C needs to be changed to G to be a stop codon. Similarly, as for the Can1 gene, mutation was confirmed in the 782nd G of ORF in all clones (FIG. 9); however, since only the mutation to C affords canavanine-resistance, the desired mutation rate is 70%. Desired mutations in both genes were simultaneously obtained in 40% clones (4 clones out of 10 clones) by investigation, and practically high efficiency was obtained.

Example 8: Editing of Polyploid Genome

Many organisms have diploid or polyploid genome. In the conventional mutation introduction methods, mutation is, in principle, introduced into only one homologous chromosome to produce a heterologous geno-type. Therefore, desired feature is not obtained unless it is a dominant mutation, and making it homologous requires labor and time. Thus, whether the technique of the present invention can introduce mutation into all target alleles on the homologous chromosome in the genome was tested.

That is, simultaneous editing of Ade1 and Can1 genes was performed in budding yeast YPH501 strain as a diploid strain. The phenotype of these gene mutations (red colony and canavanine-resistant) is a recessive phenotype, and therefore, these phenotypes do not appear unless both mutations of homologous gene (homologous mutation) are introduced.

Using the ORF of positions 1173-1154 (complementary strand) of Ade1 gene (Ade1 target 1: GTCAATAG-GATCCCCTTTT; SEQ ID NO: 31) or of positions 3-22 (Ade1 target 5: GTCAATTACGAAGACTGAAC; SEQ ID NO: 30) as the first target nucleotide sequence, and the ORF of positions 767-786 (complementary strand) of Can1 gene as the second target nucleotide sequence (Can1 target8: ATAACGGAATCCAACTGGGC; SEQ ID NO: 29), both DNAs encoding chimeric RNAs of two kinds of gRNAs each containing a nucleotide sequence complementary thereto and tracrRNA (SEQ ID NO: 7) were placed on the same plasmid (pRS426), and introduced into BY4741 strain together with plasmid nCas9 D10A-PmCDA1 containing a nucleic acid encoding a fusion protein of mutant Cas9 and PmCDA1, and expressed, and introduction of mutation into each gene was verified.

As a result of colony count, it was found that each characteristic of phenotype could be obtained at a high probability (40%-70%) (FIG. 10A).

To confirm mutation, Ade1 target region of each of white colony and red colony was sequenced to confirm overlapping of sequence signals indicating heterologous mutation in the target site of white colony (FIG. 10B, upper panel, G and T signals overlap at Phenotype was confirmed to be absent in colony with heterologous mutation. On the other hand, homologous mutation free of overlapping signal was confirmed in red colony (FIG. 10B, lower panel, T signal at ↓).

Example 9: Genome Editing in *Escherichia coli*

In this Example, it is demonstrated that this technique effectively functions in *Escherichia coli*, which is a representative bacterium model organism. Particularly, conventional nuclease type genome editing technique is fatal for bacteria, and the application is difficult. Thus, the superiority of this technique is emphasized. In combination with yeast, which is an eukaryote model cell, it is shown that this technique is widely applicable to any species irrespective of prokaryon and eukaryon.

Amino acid mutation of D10A and H840A were introduced (dCas9) into *Streptococcus pyogenes* Cas9 gene containing bidirectional promoter region, and a construct to be expressed as a fusion protein with PmCDA1 via a linker sequence was constructed, and chimeric gRNAs encoding a sequence complementary to each of the target nucleotide sequences was simultaneously included in a plasmid (full-length nucleotide sequence is shown in SEQ ID NO: 32, in which sequence, a sequence complementary to each of the target sequences is introduced into the site of $n_{20}$) (FIG. 11A).

First, the ORF of positions 426-445 (T CAA TGG GCT AAC TAC GTT C; SEQ ID NO: 33) of *Escherichia coli* galK gene was introduced as a target nucleotide sequence into a plasmid, various *Escherichia coli* strains (XL10-gold, DH5a, MG1655, BW25113) were transformed with the plasmid by calcium method or electroporation method, SOC medium was added, recovery culture was performed overnight, plasmid carrying cells were selected from ampicillin-containing LB medium, and colony was formed. Introduction of mutation was verified by direct-sequence from colony PCR. The results are shown in FIG. 11B.

Independent colony (1-3) was selected randomly, and sequence was analyzed. As a result, the 427-position C of ORF was converted to T (clones 2, 3) at a probability of not less than 60%, and the occurrence of gene destruction generating a stop codon (TAA) was confirmed.

Then, with a complementary sequence (5'-GGTCCAT-AAACTGAGACAGC-3'; SEQ ID NO: 34) of 1530-1549 base region of rpoB gene ORF, which is an essential gene, as a target, particular point mutation was introduced by a method similar to the above-mentioned method to try to impart rifampicin-resistant function to *Escherichia coli*. The sequences of colonies selected in a nonselective medium (none), a 25 µg/ml rifampicin (Rif25) and 50 µg/ml rifampicin (Rif50)-containing medium were analyzed. As a result, it was confirmed that conversion of the 1546-position G of ORF to A introduced amino acid mutation from Asp(GAC) to Asn(AAC), and rifampicin-resistance was imparted (FIG. 11C, upper panel). A 10-fold dilution series of the cell suspension after transformation treatment was spotted on a nonselective medium (none), a 25 µg/ml rifampicin (Rif25) and 50 µg/ml rifampicin (Rif50)-containing medium and cultured. As a result, it is estimated that rifampicin-resistant strain was obtained at about 10% frequency (FIG. 11C, lower panel).

As shown above, by this technique, a new function can be added by particular point mutation, rather than simple gene destruction. This technique is superior since essential gene is directly edited.

Example 10: Adjustment of Editing Base Site by GRNA Length

Conventionally, the gRNA length relative to a target nucleotide sequence was 20 b as basic, and cytosine (or guanine in opposite strand) in a site of 2-5 b from the 5'-terminus thereof (15-19 b upstream of PAM sequence) is used as a mutation target. Whether expression of different gRNA length can shift the site of the base to be the target was examined (FIG. 12A).

Experimental Example performed on *Escherichia coli* is shown in FIG. 12B. A site containing many cytosines on *Escherichia coli* genome was searched for, and the experiment was performed using gsiA gene, which is a putative ABC-transporter. Substituted cytosine was examined while changing the length of the target to 24 bp, 22 bp, 20 bp, 18 bp to find that the 898th, 899th cytosine was substituted by thymine in the case of 20 bp (standard length). When the target site is longer than 20 bp, the 896th and 897th cytosines were also substituted, and when the target site was shorter, the 900th and 901st cytosines were also substituted. In fact, the target site could be shifted by changing the length of the gRNA.

Example 11: Development of Temperature Dependent Genome Editing Plasmid

A plasmid that induces expression of the nucleic acid-modifying enzyme complex of the present invention under high temperature conditions was designed. While optimizing efficiency by limitatively controlling the expression state, reduction of side effects (growth inhibition of host, unstable mutation introduction efficiency, mutation of site different from target and the like) was aimed. Simultaneously, a simultaneous and easy removal of plasmid after editing was intended by combining a mechanism for ceasing the replication of plasmid at a high temperature. The detail of the experiment is shown below.

With temperature sensitive plasmid pSC101-Rep101 system (sequence of pSC101 ori is shown in SEQ ID NO: 35, and sequence of temperature sensitive Rep101 is shown in SEQ ID NO: 36) as a backbone, temperature sensitive λ repressor (c1857) system was used for expression induction. For genome editing, G113E mutation imparting RecA resistance was introduced into λ repressor, to ensure normal function even under SOS response (SEQ ID NO: 37). dCas9-PmCDA1 (SEQ ID NO: 38) was ligated to Right Operator (SEQ ID NO: 39), and gRNA (SEQ ID NO: 40) was ligated to the downstream of Left Operator (SEQ ID NO: 41) to regulate the expression (full-length nucleotide sequence of the constructed expression vector is shown in SEQ ID NO: 42). During culture at not more than 30° C., transcription of gRNA and expression of dCas9-PmCDA1 are suppressed, and the cells can grow normally. When cultured at not less than 37° C., transcription of gRNA and expression of dCas9-PmCDA1 are induced, and replication of plasmid is suppressed simultaneously. Therefore, a nucleic acid-modifying enzyme complex necessary for genome editing is transiently supplied, and plasmid can be removed easily after editing (FIG. 13).

Specific protocol of the base substitution is shown in FIG. 14.

The culture temperature for plasmid construction is set at around 28° C., and an *Escherichia coli* colony retaining the desired plasmid is first established. Then, the colony is directly used, or after plasmid extraction when the strain is changed, transformation with the target strain is performed again, and the obtained colony is used. Liquid culture at 28° C. is performed overnight. Thereafter, the colony is diluted with the medium, induction culture is performed at 42° C. for 1 hr to overnight, the cell suspension is appropriately diluted and spread or spotted on a plate to acquire a single colony.

As a verification experiment, point mutation introduction into essential gene rpoB was performed. When rpoB, which is one of the RNA polymerase-constituting factors, is deleted or its function is lost, the *Escherichia coli* will not survive. On the other hand, it is known that resistance to antibiotic rifampicin (Rif) is acquired when point mutation is entered at a particular site. Therefore, aiming at such introduction of point mutation, a target site is selected and assay was performed.

The results are shown in FIG. 15. In the upper left panel, the left shows an LB (chloramphenicol addition) plate, and the right shows a rifampicin-added LB (chloramphenicol addition) plate, and samples with or without chloramphenicol were prepared and cultured at 28° C. or 42° C. When cultured at 28° C., the rate of Rif resistance is low; however, when cultured at 42° C., rifampicin resistance was obtained with extremely high efficiency. When the colonies (non-selection) obtained on LB were sequenced by 8 colonies, the 1546th guanine (G) was substituted by adenine (A) in not less than 60% of the strain cultured at 42° C. (lower and upper left panels). It is clear that the base is also completely substituted in actual sequence spectrum (lower right panel).

Similarly, base substitution of galK, which is one of the factors involved in the galactose metabolism, was performed. Since metabolism of 2-deoxy-galactose (2DOG), which is an analogue of galactose, by galK is fatal to *Escherichia coli*, this was used as a selection method. Target site was set such that missense mutation is induced in target 8, and that stop codon is entered in target 12 (FIG. 16 lower right).

The results are shown in FIG. 16. In the upper left and lower left panels, the left shows an LB (chloramphenicol addition) plate, and the right shows a 2-DOG-added LB (chloramphenicol addition) plate, and samples with or without chloramphenicol were prepared and cultured at 28° C. or 42° C. In target 8, colony was produced only slightly on a 2-DOG addition plate (upper left panel), 3 colonies on LB (red frame) were sequenced to determine that the 61st cytosine (C) was substituted by thymine (T) in all colonies (upper right). This mutation is assumed to be insufficient to lose function of galK. On the other hand, in target 12, colony was obtained on 2-DOG addition plate by culture at 28° C.

and 42° C. (lower left panel). 3 colonies on LB were sequenced to determine that the 271st cytosine was substituted by thymine in all colonies (lower right). It was shown that mutation can be also introduced stably and highly efficiently in such different targets.

The contents disclosed in any publication cited herein, including patents and patent applications, are hereby incorporated in their entireties by reference, to the extent that they have been disclosed herein.

This application is based on patent application Nos. 2014-43348 and 2014-201859 filed in Japan (filing dates: Mar. 5, 2014 and Sep. 30, 2014, respectively), the contents of which are incorporated in full herein.

INDUSTRIAL APPLICABILITY

The present invention makes it possible to safely introduce site specific mutation into any species without insertion of a foreign DNA or double-stranded DNA breaks. It is also possible to set a wide range of mutation introduction from a pin point of one base to several hundred bases, and the technique can also be applied to topical evolution induction by introduction of random mutation into a particular restricted region, which has been almost impossible heretofore, and is extremely useful.

The invention claimed is:

1. A nucleic acid-modifying enzyme complex of a nucleic acid sequence-recognizing module that specifically binds to a target nucleotide sequence in a double stranded DNA with a nucleic acid base converting enzyme linked thereto, wherein the nucleic acid sequence-recognizing module is a CRISPR-Cas system comprising a Cas9 protein, wherein both DNA cleavage abilities of the Cas9 protein are inactivated, wherein the complex is capable of converting one or more nucleotides in the targeted site to other one or more nucleotides or deleting one or more nucleotides in a targeted site, or inserting one or more nucleotides into the targeted site, without cleaving both of the strands of the double stranded DNA in the targeted site, wherein the complex is formed via an interaction between (i) one or more protein binding domains that are fused to the nucleic acid sequence-recognizing module and (ii) one or more binding partners of said one or more protein binding domains, said binding partner being fused to the nucleic acid base converting enzyme, wherein the one or more protein binding domains is/are SH3 domain(s) and the one or more binding partners is/are SH3 ligand(s).

2. The nucleic acid-modifying enzyme complex according to claim 1, wherein the nucleic acid base converting enzyme is PmCDA1 or human AID.

3. The nucleic acid-modifying enzyme complex according to claim 2, wherein the nucleic acid base converting enzyme is PmCDA1.

4. The nucleic acid-modifying enzyme complex according to claim 1, wherein the Cas9 protein is encoded by a nucleic acid sequence comprising a sequence set forth in SEQ ID NO: 5, wherein the nucleic acid base converting enzyme is PmCDA1, and wherein aspartate at position 10 of the Cas9 protein encoded by SEQ ID NO: 5 is converted to alanine, and histidine at position 840 of the Cas9 protein encoded by SEQ ID NO: 5 is converted to alanine.

* * * * *